US012758647B2

(12) United States Patent
Smith et al.

(10) Patent No.: US 12,758,647 B2
(45) Date of Patent: Oct. 13, 2026

(54) ANTI-CSPG4 BINDING AGENTS, ENCODING NUCLEIC ACIDS THEREOF, CONJUGATES THEREOF AND METHODS OF USE THEREOF TO TREAT A CSPG4+ CANCER

(71) Applicant: Ardeagen Corporation, Woodinville, WA (US)

(72) Inventors: Maria Leia Smith, Seattle, WA (US); May Kung Sutherland, Bothell, WA (US)

(73) Assignee: Ardeagen Corporation, Woodinville, WA (US)

( * ) Notice: Subject to any disclaimer, the term of this patent is extended or adjusted under 35 U.S.C. 154(b) by 631 days.

(21) Appl. No.: 18/247,628

(22) PCT Filed: Oct. 15, 2021

(86) PCT No.: PCT/US2021/055311

§ 371 (c)(1),
(2) Date: Mar. 31, 2023

(87) PCT Pub. No.: WO2022/082066

PCT Pub. Date: Apr. 21, 2022

(65) Prior Publication Data

US 2025/0213715 A1 Jul. 3, 2025

Related U.S. Application Data

(60) Provisional application No. 63/093,255, filed on Oct. 18, 2020.

(51) Int. Cl.

| | |
|---|---|
| ***A61K 47/68*** | (2017.01) |
| ***A61K 39/395*** | (2006.01) |
| ***A61P 35/00*** | (2006.01) |

(52) U.S. Cl.

CPC .... *A61K 47/6865* (2017.08); *A61K 39/39558* (2013.01); *A61K 47/68031* (2023.08); *A61K 47/68037* (2023.08); *A61K 47/6851* (2017.08); *A61K 47/6857* (2017.08); *A61K 47/6889* (2017.08); *A61P 35/00* (2018.01)

(58) Field of Classification Search

CPC .......... A61K 47/6865; A61K 39/39558; A61K 47/68031; A61K 47/68037; A61K 47/6851; A61K 47/6857; A61K 47/6889; A61K 2039/505; A61P 35/00; C07K 2317/24; C07K 2317/56; C07K 2317/565; C07K 2317/73; C07K 2317/77; C07K 2317/92; C07K 16/3053

See application file for complete search history.

(56) References Cited

U.S. PATENT DOCUMENTS

| | | | | |
|---|---|---|---|---|
| 4,256,746 | A | 3/1981 | Miyashita et al. | |
| 4,294,757 | A | 10/1981 | Asai | |
| 4,307,016 | A | 12/1981 | Asai et al. | |
| 4,313,946 | A | 2/1982 | Powell et al. | |
| 4,315,929 | A | 2/1982 | Freedman et al. | |
| 4,322,348 | A | 3/1982 | Asai et al. | |
| 4,331,598 | A | 5/1982 | Hasegawa et al. | |
| 4,361,650 | A | 11/1982 | Asai et al. | |
| 4,362,663 | A | 12/1982 | Kida et al. | |
| 4,364,866 | A | 12/1982 | Asai et al. | |
| 4,371,533 | A | 2/1983 | Akimoto et al. | |
| 4,424,219 | A | 1/1984 | Hashimoto et al. | |
| 4,450,254 | A | 5/1984 | Isley et al. | |
| 4,880,935 | A | 11/1989 | Thorpe | |
| 5,122,368 | A | 6/1992 | Greenfield et al. | |
| 5,126,262 | A | 6/1992 | Matsui et al. | |
| 5,362,852 | A | 11/1994 | Geoghegan | |
| 5,622,929 | A | 4/1997 | Willner et al. | |
| 5,824,805 | A | 10/1998 | King et al. | |
| 6,214,345 | B1 | 4/2001 | Firestone et al. | |
| 6,884,869 | B2 | 4/2005 | Senter et al. | |
| 7,498,298 | B2 | 3/2009 | Doronina et al. | |
| 7,585,491 | B2 | 9/2009 | Govindan | |
| 7,591,944 | B2 | 9/2009 | Carnell et al. | |
| 7,603,962 | B2 | 10/2009 | Hama et al. | |
| 7,999,083 | B2 | 8/2011 | Govindan et al. | |
| 8,080,250 | B1 | 12/2011 | Govindan et al. | |
| 8,992,932 | B2 | 3/2015 | Lerchen et al. | |
| 9,078,931 | B2 | 7/2015 | Satpayev et al. | |
| 9,211,319 | B2 | 12/2015 | Sievers et al. | |
| 9,296,811 | B2 | 3/2016 | Ferrone et al. | |
| 9,345,785 | B2 | 5/2016 | Law et al. | |
| 9,375,489 | B2 * | 6/2016 | Govindan | A61K 47/6863 |
| 9,463,252 | B2 | 10/2016 | Senter et al. | |
| 9,504,756 | B2 | 11/2016 | Lyon et al. | |
| 9,808,537 | B2 | 11/2017 | Masuda et al. | |

(Continued)

FOREIGN PATENT DOCUMENTS

| | | | |
|---|---|---|---|
| WO | WO 2004001095 | A1 | 12/2003 |
| WO | WO 2004010957 | A2 | 2/2004 |

(Continued)

OTHER PUBLICATIONS

Topalian SL, et al. (Apr. 13, 2015) Cancer Cell. 27:450-61.*

(Continued)

*Primary Examiner* — Robert S Landsman

(74) *Attorney, Agent, or Firm* — Seed Intellectual Property Law Group LLP

(57) ABSTRACT

The present disclosure provides anti-CSPG4 antibodies, antigen binding portions thereof and CSPG4 conjugates thereof for use in the treatment of cancer.

41 Claims, 12 Drawing Sheets

Specification includes a Sequence Listing.

(56) References Cited

U.S. PATENT DOCUMENTS

| | | | |
|---|---|---|---|
| 2005/0238649 A1 | 10/2005 | Doronina et al. |
| 2006/0074008 A1 | 4/2006 | Senter et al. |
| 2009/0010945 A1 | 1/2009 | Alley et al. |
| 2010/0158909 A1 | 6/2010 | McDonagh et al. |
| 2013/0078251 A1 | 3/2013 | Freytag et al. |
| 2014/0242083 A1 | 8/2014 | Hofer et al. |
| 2015/0297748 A1 | 10/2015 | Masuda et al. |
| 2016/0032007 A1 | 2/2016 | Bigner et al. |
| 2017/0369588 A1 | 12/2017 | Perris et al. |
| 2018/0072811 A1 | 3/2018 | Ferrone et al. |

FOREIGN PATENT DOCUMENTS

| | | |
|---|---|---|
| WO | WO 2005037992 A2 | 4/2005 |
| WO | WO 2005081711 A2 | 9/2005 |
| WO | WO 2006034488 A2 | 3/2006 |
| WO | WO 2007008603 A1 | 1/2007 |
| WO | WO 2010033866 A2 | 3/2010 |
| WO | WO 2010141566 A1 | 12/2010 |
| WO | WO 2011156328 A1 | 12/2011 |
| WO | WO 2013026832 A1 | 2/2013 |
| WO | WO 2013026839 A1 | 2/2013 |
| WO | WO 2014065661 A1 | 5/2014 |
| WO | WO 2014072482 A1 | 5/2014 |
| WO | WO 2014131715 A1 | 9/2014 |
| WO | WO 2015057066 A1 | 4/2015 |
| WO | WO 2015057699 A2 | 4/2015 |
| WO | WO 2015095755 A1 | 6/2015 |
| WO | WO 2015123679 A1 | 8/2015 |
| WO | WO 2016022027 A1 | 2/2016 |
| WO | WO 2016040684 A1 | 3/2016 |
| WO | WO 2016040856 A2 | 3/2016 |
| WO | WO 2017096311 A1 | 6/2017 |
| WO | WO 2017147542 A2 | 8/2017 |
| WO | WO 2018031690 A1 | 2/2018 |
| WO | WO 2020123425 A2 | 6/2020 |

OTHER PUBLICATIONS

Alley et al., "Antibody-drug conjugates: targeted drug delivery for cancer," Current Opinion in Chemical Biology 14:529-537, Aug. 2010 [Published online Jul. 17, 2010]. (9 pages).

Carter et al., "Antibody-Drug Conjugates for Cancer Therapy," The Cancer Journal 14(3):154-169, May/Jun. 2008. (16 pages).

Chari et al., "Immunoconjugates Containing Novel Maytansinoids: Promising Anticancer Drugs," *Cancer Research* 52:127-131, Jan. 1992. (7 pages).

Dubowchik et al., "Receptor-mediated and enzyme-dependent targeting of cytotoxic anticancer drugs," Pharmacology & Therapeutics 83(2):67-123, Aug. 1999. (57 pages).

Geoghegan et al., "Site-Directed Conjugation of Nonpeptide Groups to Peptides and Proteins via Periodate Oxidation of a 2-Amino Alcohol. Application to Modification at N-Terminal Serine," Bioconjugate Chem. 3(2):138-146, Mar.-Apr. 1992. (9 pages).

International Search Report and Written Opinion, dated Feb. 2, 2022, for International Patent Application No. PCT/US2021/055311. (17 pages).

Johnson et al., "Anti-Tumor Activity of CC49-Doxorubicin Immunoconjugates," *Anticancer Research* 15(4):1387-1393, Jul.-Aug. 1995. (7 pages).

Lau et al., "Conjugation of Doxorubicin to Monoclonal Anti-carcinoembryonic Antigen Antibody via Novel Thiol-directed Cross-linking Reagents," Bioorganic & Medicinal Chemistry 3(10):1299-1304, Oct. 1995. (6 pages).

Lau et al., "Novel Doxorubicin-Monoclonal Anti-carcinoembryonic Antigen Antibody Immunoconjugate Activity in vitro," Bioorganic & Medicinal Chemistry 3(10):1305-1312, Oct. 1995. (8 pages).

Mittleman et al., "Identification of Monoclonal Anti-HMW-MAA Antobody Linear peptide Epitope by Proteomic Database Mining," J Invest Dermatol 123:670-675, Oct. 2004. (6 pages).

Musto et al., "Differential sensing of sugars by colorimetric arrays," *Current Opinion in Chemical Biology* 14:1-9, Dec. 2010. (9 pages).

Neville et al., "In vivo T-cell ablation by a holo-immunotoxin directed at human CD3," *Proc. Natl. Acad. Sci. USA* 89:2585-2589, Apr. 1992. (5 pages).

Neville et al., "Enhancement of Immunotoxin Efficacy by Acid-cleavable Crosslinking Agents Utilizing Diphtheria Toxin and Toxin Mutants*," The Journal of Biological Chemistry 264(25):14653-14661, Sep. 5, 1989. (9 pages).

Thorpe et al., "New Coupling Agents for the Synthesis of Immunotoxins Containing a Hindered Disulfide Bond with Improved Stability in vivo," *Cancer Research 47*:5924-5931, Nov. 1987. (8 pages).

* cited by examiner

| Test Agent Description | Conjugation/Enrichment/ Purification | DAR4 (%) | Drug load | Binding to hCSPG4 (EC50, ng/ml) |
|---|---|---|---|---|
| ARD107 mAb | unconjugated | N/A | 0 | 21 |
| ARD107-vcMMAE | Stochastic conjugation | 45 | 4.2 | 23 |
| ARD107-vcMMAE [DAR4] | Conjugation enriched for 4-load | 71.5 | 4.0 | 20 |
| ARD107-vcMMAE [HIC] | Stochastic/HIC Purified for 4-load | 92 | 4.0 | 17 |
| ARD107-Gly-vcMMAE | Conjugation enriched for 4-load | 70 | 3.9 | 17 |

FIG. 6

| | Chimeric | H1L2 | H3L2 | H3L3 |
|---|---|---|---|---|
| EC50, nM | 0.41 | 0.45 | 0.33 | 0.13 |

| | Chimeric | H1L2 | H3L2 | H3L3 |
|---|---|---|---|---|
| EC50, nM | 0.49 | 0.53 | 0.46 | 0.12 |

SEQUENCE LISTING

```
<160> NUMBER OF SEQ ID NOS: 48

<210> SEQ ID NO 1
<211> LENGTH: 112
<212> TYPE: PRT
<213> ORGANISM: Artificial Sequence
<220> FEATURE:
<223> OTHER INFORMATION: Synthetic sequence ARD107 VH

<400> SEQUENCE: 1

Glu Val Gln Leu Gln Glu Ser Gly Pro Gly Leu Val Lys Pro Ser Gln
1               5                   10                  15

Ser Leu Ser Leu Thr Cys Ser Val Thr Gly Tyr Ser Ile Thr Ser Gly
            20                  25                  30

Tyr Tyr Trp Asn Trp Ile Arg Gln Phe Pro Gly Asn Lys Leu Glu Trp
        35                  40                  45
```

```
Met Gly Tyr Ile Thr Tyr Asp Gly Ser Asn Asn Tyr Asn Pro Ser Leu
    50                  55                  60

Lys Asn Arg Ile Ser Ile Thr Arg Asp Thr Ser Lys Asn Gln Phe Phe
65                  70                  75                  80

Leu Lys Leu Asn Ser Val Thr Thr Glu Asp Thr Ala Thr Tyr Tyr Cys
                85                  90                  95

Ala Asp Phe Asp Tyr Trp Gly Gln Gly Thr Thr Leu Thr Val Ser Ser
            100                 105                 110


<210> SEQ ID NO 2
<211> LENGTH: 107
<212> TYPE: PRT
<213> ORGANISM: Artificial Sequence
<220> FEATURE:
<223> OTHER INFORMATION: Synthetic sequence ARD107 VL

<400> SEQUENCE: 2

Asp Ile Val Leu Thr Gln Ser Pro Ser Ser Leu Ser Ala Ser Leu Gly
1               5                   10                  15

Asp Arg Val Thr Ile Ser Cys Ser Ala Ser Gln Gly Ile Arg Asn Tyr
            20                  25                  30

Leu Asn Trp Tyr Gln Gln Arg Pro Asp Gly Thr Val Lys Leu Leu Ile
        35                  40                  45

Tyr Tyr Thr Ser Ser Leu His Ser Gly Val Pro Ser Arg Phe Ser Gly
    50                  55                  60

Ser Gly Ser Gly Thr Asp Tyr Ser Leu Thr Ile Ser Asn Leu Glu Pro
65                  70                  75                  80

Glu Asp Ile Ala Thr Tyr Tyr Cys Gln Gln Tyr Ser Lys Leu Pro Trp
                85                  90                  95

Thr Phe Gly Gly Gly Thr Lys Leu Glu Ile Lys
            100                 105


<210> SEQ ID NO 3
<211> LENGTH: 442
<212> TYPE: PRT
<213> ORGANISM: Artificial Sequence
<220> FEATURE:
<223> OTHER INFORMATION: Synthetic sequence ARD107 VH-IgG1

<400> SEQUENCE: 3

Glu Val Gln Leu Gln Glu Ser Gly Pro Gly Leu Val Lys Pro Ser Gln
1               5                   10                  15

Ser Leu Ser Leu Thr Cys Ser Val Thr Gly Tyr Ser Ile Thr Ser Gly
            20                  25                  30

Tyr Tyr Trp Asn Trp Ile Arg Gln Phe Pro Gly Asn Lys Leu Glu Trp
        35                  40                  45

Met Gly Tyr Ile Thr Tyr Asp Gly Ser Asn Asn Tyr Asn Pro Ser Leu
    50                  55                  60

Lys Asn Arg Ile Ser Ile Thr Arg Asp Thr Ser Lys Asn Gln Phe Phe
65                  70                  75                  80

Leu Lys Leu Asn Ser Val Thr Thr Glu Asp Thr Ala Thr Tyr Tyr Cys
                85                  90                  95

Ala Asp Phe Asp Tyr Trp Gly Gln Gly Thr Thr Leu Thr Val Ser Ser
            100                 105                 110

Ala Ser Thr Lys Gly Pro Ser Val Phe Pro Leu Ala Pro Ser Ser Lys
        115                 120                 125

Ser Thr Ser Gly Gly Thr Ala Ala Leu Gly Cys Leu Val Lys Asp Tyr
```

```
    130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175

Leu Ser Ser Val Val Thr Val Pro Ser Ser Ser Leu Gly Thr Gln Thr
            180                 185                 190

Tyr Ile Cys Asn Val Asn His Lys Pro Ser Asn Thr Lys Val Asp Lys
        195                 200                 205

Lys Val Glu Pro Lys Ser Cys Asp Lys Thr His Thr Cys Pro Pro Cys
    210                 215                 220

Pro Ala Pro Glu Leu Leu Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser His Glu Asp Pro Glu Val Lys Phe Asn Trp
            260                 265                 270

Tyr Val Asp Gly Val Glu Val His Asn Ala Lys Thr Lys Pro Arg Glu
        275                 280                 285

Glu Gln Tyr Asn Ser Thr Tyr Arg Val Val Ser Val Leu Thr Val Leu
    290                 295                 300

His Gln Asp Trp Leu Asn Gly Lys Glu Tyr Lys Cys Lys Val Ser Asn
305                 310                 315                 320

Lys Ala Leu Pro Ala Pro Ile Glu Lys Thr Ile Ser Lys Ala Lys Gly
                325                 330                 335

Gln Pro Arg Glu Pro Gln Val Tyr Thr Leu Pro Pro Ser Arg Asp Glu
            340                 345                 350

Leu Thr Lys Asn Gln Val Ser Leu Thr Cys Leu Val Lys Gly Phe Tyr
        355                 360                 365

Pro Ser Asp Ile Ala Val Glu Trp Glu Ser Asn Gly Gln Pro Glu Asn
    370                 375                 380

Asn Tyr Lys Thr Thr Pro Pro Val Leu Asp Ser Asp Gly Ser Phe Phe
385                 390                 395                 400

Leu Tyr Ser Lys Leu Thr Val Asp Lys Ser Arg Trp Gln Gln Gly Asn
                405                 410                 415

Val Phe Ser Cys Ser Val Met His Glu Ala Leu His Asn His Tyr Thr
            420                 425                 430

Gln Lys Ser Leu Ser Leu Ser Pro Gly Lys
        435                 440


<210> SEQ ID NO 4
<211> LENGTH: 214
<212> TYPE: PRT
<213> ORGANISM: Artificial Sequence
<220> FEATURE:
<223> OTHER INFORMATION: Synthetic sequence ARD107 VL-Igkappa

<400> SEQUENCE: 4

Asp Ile Val Leu Thr Gln Ser Pro Ser Ser Leu Ser Ala Ser Leu Gly
1               5                   10                  15

Asp Arg Val Thr Ile Ser Cys Ser Ala Ser Gln Gly Ile Arg Asn Tyr
            20                  25                  30

Leu Asn Trp Tyr Gln Gln Arg Pro Asp Gly Thr Val Lys Leu Leu Ile
        35                  40                  45

Tyr Tyr Thr Ser Ser Leu His Ser Gly Val Pro Ser Arg Phe Ser Gly
```

```
    50                  55                  60

Ser Gly Ser Gly Thr Asp Tyr Ser Leu Thr Ile Ser Asn Leu Glu Pro
65                  70                  75                  80

Glu Asp Ile Ala Thr Tyr Tyr Cys Gln Gln Tyr Ser Lys Leu Pro Trp
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 5
<211> LENGTH: 19
<212> TYPE: PRT
<213> ORGANISM: Artificial Sequence
<220> FEATURE:
<223> OTHER INFORMATION: VH Signal Sequence

<400> SEQUENCE: 5

Met Glu Phe Gly Leu Ser Trp Leu Phe Leu Val Ala Ile Leu Lys Gly
1               5                   10                  15

Val Gln Cys


<210> SEQ ID NO 6
<211> LENGTH: 22
<212> TYPE: PRT
<213> ORGANISM: Artificial Sequence
<220> FEATURE:
<223> OTHER INFORMATION: VL Signal Sequence

<400> SEQUENCE: 6

Met Asp Met Arg Val Pro Ala Gln Leu Leu Gly Leu Leu Leu Leu Trp
1               5                   10                  15

Phe Pro Gly Ser Arg Cys
            20


<210> SEQ ID NO 7
<211> LENGTH: 461
<212> TYPE: PRT
<213> ORGANISM: Artificial Sequence
<220> FEATURE:
<223> OTHER INFORMATION: ARD107 VH-IgG1 with signal sequence

<400> SEQUENCE: 7

Met Glu Phe Gly Leu Ser Trp Leu Phe Leu Val Ala Ile Leu Lys Gly
1               5                   10                  15

Val Gln Cys Glu Val Gln Leu Gln Glu Ser Gly Pro Gly Leu Val Lys
            20                  25                  30
```

-continued

```
Pro Ser Gln Ser Leu Ser Leu Thr Cys Ser Val Thr Gly Tyr Ser Ile
        35                  40                  45

Thr Ser Gly Tyr Tyr Trp Asn Trp Ile Arg Gln Phe Pro Gly Asn Lys
    50                  55                  60

Leu Glu Trp Met Gly Tyr Ile Thr Tyr Asp Gly Ser Asn Asn Tyr Asn
65                  70                  75                  80

Pro Ser Leu Lys Asn Arg Ile Ser Ile Thr Arg Asp Thr Ser Lys Asn
                85                  90                  95

Gln Phe Phe Leu Lys Leu Asn Ser Val Thr Thr Glu Asp Thr Ala Thr
            100                 105                 110

Tyr Tyr Cys Ala Asp Phe Asp Tyr Trp Gly Gln Gly Thr Thr Leu Thr
        115                 120                 125

Val Ser Ser Ala Ser Thr Lys Gly Pro Ser Val Phe Pro Leu Ala Pro
    130                 135                 140

Ser Ser Lys Ser Thr Ser Gly Gly Thr Ala Ala Leu Gly Cys Leu Val
145                 150                 155                 160

Lys Asp Tyr Phe Pro Glu Pro Val Thr Val Ser Trp Asn Ser Gly Ala
                165                 170                 175

Leu Thr Ser Gly Val His Thr Phe Pro Ala Val Leu Gln Ser Ser Gly
            180                 185                 190

Leu Tyr Ser Leu Ser Ser Val Val Thr Val Pro Ser Ser Ser Leu Gly
        195                 200                 205

Thr Gln Thr Tyr Ile Cys Asn Val Asn His Lys Pro Ser Asn Thr Lys
    210                 215                 220

Val Asp Lys Lys Val Glu Pro Lys Ser Cys Asp Lys Thr His Thr Cys
225                 230                 235                 240

Pro Pro Cys Pro Ala Pro Glu Leu Leu Gly Gly Pro Ser Val Phe Leu
                245                 250                 255

Phe Pro Pro Lys Pro Lys Asp Thr Leu Met Ile Ser Arg Thr Pro Glu
            260                 265                 270

Val Thr Cys Val Val Val Asp Val Ser His Glu Asp Pro Glu Val Lys
        275                 280                 285

Phe Asn Trp Tyr Val Asp Gly Val Glu Val His Asn Ala Lys Thr Lys
    290                 295                 300

Pro Arg Glu Glu Gln Tyr Asn Ser Thr Tyr Arg Val Val Ser Val Leu
305                 310                 315                 320

Thr Val Leu His Gln Asp Trp Leu Asn Gly Lys Glu Tyr Lys Cys Lys
                325                 330                 335

Val Ser Asn Lys Ala Leu Pro Ala Pro Ile Glu Lys Thr Ile Ser Lys
            340                 345                 350

Ala Lys Gly Gln Pro Arg Glu Pro Gln Val Tyr Thr Leu Pro Pro Ser
        355                 360                 365

Arg Asp Glu Leu Thr Lys Asn Gln Val Ser Leu Thr Cys Leu Val Lys
    370                 375                 380

Gly Phe Tyr Pro Ser Asp Ile Ala Val Glu Trp Glu Ser Asn Gly Gln
385                 390                 395                 400

Pro Glu Asn Asn Tyr Lys Thr Thr Pro Pro Val Leu Asp Ser Asp Gly
                405                 410                 415

Ser Phe Phe Leu Tyr Ser Lys Leu Thr Val Asp Lys Ser Arg Trp Gln
            420                 425                 430

Gln Gly Asn Val Phe Ser Cys Ser Val Met His Glu Ala Leu His Asn
        435                 440                 445

His Tyr Thr Gln Lys Ser Leu Ser Leu Ser Pro Gly Lys
```

```
    450                 455                 460


<210> SEQ ID NO 8
<211> LENGTH: 236
<212> TYPE: PRT
<213> ORGANISM: Artificial Sequence
<220> FEATURE:
<223> OTHER INFORMATION: Synthetic sequence ARD107 VL-Igkappa with
      signal sequence

<400> SEQUENCE: 8

Met Asp Met Arg Val Pro Ala Gln Leu Leu Gly Leu Leu Leu Leu Trp
1               5                   10                  15

Phe Pro Gly Ser Arg Cys Asp Ile Val Leu Thr Gln Ser Pro Ser Ser
            20                  25                  30

Leu Ser Ala Ser Leu Gly Asp Arg Val Thr Ile Ser Cys Ser Ala Ser
        35                  40                  45

Gln Gly Ile Arg Asn Tyr Leu Asn Trp Tyr Gln Gln Arg Pro Asp Gly
    50                  55                  60

Thr Val Lys Leu Leu Ile Tyr Tyr Thr Ser Ser Leu His Ser Gly Val
65                  70                  75                  80

Pro Ser Arg Phe Ser Gly Ser Gly Ser Gly Thr Asp Tyr Ser Leu Thr
                85                  90                  95

Ile Ser Asn Leu Glu Pro Glu Asp Ile Ala Thr Tyr Tyr Cys Gln Gln
            100                 105                 110

Tyr Ser Lys Leu Pro Trp Thr Phe Gly Gly Gly Thr Lys Leu Glu Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235


<210> SEQ ID NO 9
<211> LENGTH: 2322
<212> TYPE: PRT
<213> ORGANISM: Homo sapiens
<220> FEATURE:
<223> OTHER INFORMATION: CSPG4 [NP_001888.2]

<400> SEQUENCE: 9

Met Gln Ser Gly Pro Arg Pro Pro Leu Pro Ala Pro Gly Leu Ala Leu
1               5                   10                  15

Ala Leu Thr Leu Thr Met Leu Ala Arg Leu Ala Ser Ala Ala Ser Phe
            20                  25                  30

Phe Gly Glu Asn His Leu Glu Val Pro Val Ala Thr Ala Leu Thr Asp
        35                  40                  45

Ile Asp Leu Gln Leu Gln Phe Ser Thr Ser Gln Pro Glu Ala Leu Leu
    50                  55                  60
```

-continued

```
Leu Leu Ala Ala Gly Pro Ala Asp His Leu Leu Leu Gln Leu Tyr Ser
65                  70                  75                  80

Gly Arg Leu Gln Val Arg Leu Val Leu Gly Gln Glu Glu Leu Arg Leu
                85                  90                  95

Gln Thr Pro Ala Glu Thr Leu Leu Ser Asp Ser Ile Pro His Thr Val
            100                 105                 110

Val Leu Thr Val Val Glu Gly Trp Ala Thr Leu Ser Val Asp Gly Phe
        115                 120                 125

Leu Asn Ala Ser Ser Ala Val Pro Gly Ala Pro Leu Glu Val Pro Tyr
    130                 135                 140

Gly Leu Phe Val Gly Gly Thr Gly Thr Leu Gly Leu Pro Tyr Leu Arg
145                 150                 155                 160

Gly Thr Ser Arg Pro Leu Arg Gly Cys Leu His Ala Ala Thr Leu Asn
                165                 170                 175

Gly Arg Ser Leu Leu Arg Pro Leu Thr Pro Asp Val His Glu Gly Cys
            180                 185                 190

Ala Glu Glu Phe Ser Ala Ser Asp Asp Val Ala Leu Gly Phe Ser Gly
        195                 200                 205

Pro His Ser Leu Ala Ala Phe Pro Ala Trp Gly Thr Gln Asp Glu Gly
    210                 215                 220

Thr Leu Glu Phe Thr Leu Thr Thr Gln Ser Arg Gln Ala Pro Leu Ala
225                 230                 235                 240

Phe Gln Ala Gly Gly Arg Arg Gly Asp Phe Ile Tyr Val Asp Ile Phe
                245                 250                 255

Glu Gly His Leu Arg Ala Val Val Glu Lys Gly Gln Gly Thr Val Leu
            260                 265                 270

Leu His Asn Ser Val Pro Val Ala Asp Gly Gln Pro His Glu Val Ser
        275                 280                 285

Val His Ile Asn Ala His Arg Leu Glu Ile Ser Val Asp Gln Tyr Pro
    290                 295                 300

Thr His Thr Ser Asn Arg Gly Val Leu Ser Tyr Leu Glu Pro Arg Gly
305                 310                 315                 320

Ser Leu Leu Leu Gly Gly Leu Asp Ala Glu Ala Ser Arg His Leu Gln
                325                 330                 335

Glu His Arg Leu Gly Leu Thr Pro Glu Ala Thr Asn Ala Ser Leu Leu
            340                 345                 350

Gly Cys Met Glu Asp Leu Ser Val Asn Gly Gln Arg Arg Gly Leu Arg
        355                 360                 365

Glu Ala Leu Leu Thr Arg Asn Met Ala Ala Gly Cys Arg Leu Glu Glu
    370                 375                 380

Glu Glu Tyr Glu Asp Asp Ala Tyr Gly His Tyr Glu Ala Phe Ser Thr
385                 390                 395                 400

Leu Ala Pro Glu Ala Trp Pro Ala Met Glu Leu Pro Glu Pro Cys Val
                405                 410                 415

Pro Glu Pro Gly Leu Pro Pro Val Phe Ala Asn Phe Thr Gln Leu Leu
            420                 425                 430

Thr Ile Ser Pro Leu Val Val Ala Glu Gly Gly Thr Ala Trp Leu Glu
        435                 440                 445

Trp Arg His Val Gln Pro Thr Leu Asp Leu Met Glu Ala Glu Leu Arg
    450                 455                 460

Lys Ser Gln Val Leu Phe Ser Val Thr Arg Gly Ala Arg His Gly Glu
465                 470                 475                 480
```

-continued

```
Leu Glu Leu Asp Ile Pro Gly Ala Gln Ala Arg Lys Met Phe Thr Leu
                485                 490                 495

Leu Asp Val Val Asn Arg Lys Ala Arg Phe Ile His Asp Gly Ser Glu
            500                 505                 510

Asp Thr Ser Asp Gln Leu Val Leu Glu Val Ser Val Thr Ala Arg Val
        515                 520                 525

Pro Met Pro Ser Cys Leu Arg Arg Gly Gln Thr Tyr Leu Leu Pro Ile
    530                 535                 540

Gln Val Asn Pro Val Asn Asp Pro Pro His Ile Ile Phe Pro His Gly
545                 550                 555                 560

Ser Leu Met Val Ile Leu Glu His Thr Gln Lys Pro Leu Gly Pro Glu
                565                 570                 575

Val Phe Gln Ala Tyr Asp Pro Asp Ser Ala Cys Glu Gly Leu Thr Phe
            580                 585                 590

Gln Val Leu Gly Thr Ser Ser Gly Leu Pro Val Glu Arg Arg Asp Gln
        595                 600                 605

Pro Gly Glu Pro Ala Thr Glu Phe Ser Cys Arg Glu Leu Glu Ala Gly
    610                 615                 620

Ser Leu Val Tyr Val His Arg Gly Gly Pro Ala Gln Asp Leu Thr Phe
625                 630                 635                 640

Arg Val Ser Asp Gly Leu Gln Ala Ser Pro Pro Ala Thr Leu Lys Val
                645                 650                 655

Val Ala Ile Arg Pro Ala Ile Gln Ile His Arg Ser Thr Gly Leu Arg
            660                 665                 670

Leu Ala Gln Gly Ser Ala Met Pro Ile Leu Pro Ala Asn Leu Ser Val
        675                 680                 685

Glu Thr Asn Ala Val Gly Gln Asp Val Ser Val Leu Phe Arg Val Thr
    690                 695                 700

Gly Ala Leu Gln Phe Gly Glu Leu Gln Lys Gln Gly Ala Gly Gly Val
705                 710                 715                 720

Glu Gly Ala Glu Trp Trp Ala Thr Gln Ala Phe His Gln Arg Asp Val
                725                 730                 735

Glu Gln Gly Arg Val Arg Tyr Leu Ser Thr Asp Pro Gln His His Ala
            740                 745                 750

Tyr Asp Thr Val Glu Asn Leu Ala Leu Glu Val Gln Val Gly Gln Glu
        755                 760                 765

Ile Leu Ser Asn Leu Ser Phe Pro Val Thr Ile Gln Arg Ala Thr Val
    770                 775                 780

Trp Met Leu Arg Leu Glu Pro Leu His Thr Gln Asn Thr Gln Gln Glu
785                 790                 795                 800

Thr Leu Thr Thr Ala His Leu Glu Ala Thr Leu Glu Glu Ala Gly Pro
                805                 810                 815

Ser Pro Pro Thr Phe His Tyr Glu Val Val Gln Ala Pro Arg Lys Gly
            820                 825                 830

Asn Leu Gln Leu Gln Gly Thr Arg Leu Ser Asp Gly Gln Gly Phe Thr
        835                 840                 845

Gln Asp Asp Ile Gln Ala Gly Arg Val Thr Tyr Gly Ala Thr Ala Arg
    850                 855                 860

Ala Ser Glu Ala Val Glu Asp Thr Phe Arg Phe Arg Val Thr Ala Pro
865                 870                 875                 880

Pro Tyr Phe Ser Pro Leu Tyr Thr Phe Pro Ile His Ile Gly Gly Asp
                885                 890                 895

Pro Asp Ala Pro Val Leu Thr Asn Val Leu Leu Val Val Pro Glu Gly
```

-continued

```
            900                 905                 910

Gly Glu Gly Val Leu Ser Ala Asp His Leu Phe Val Lys Ser Leu Asn
        915                 920                 925

Ser Ala Ser Tyr Leu Tyr Glu Val Met Glu Arg Pro Arg His Gly Arg
    930                 935                 940

Leu Ala Trp Arg Gly Thr Gln Asp Lys Thr Thr Met Val Thr Ser Phe
945                 950                 955                 960

Thr Asn Glu Asp Leu Leu Arg Gly Arg Leu Val Tyr Gln His Asp Asp
                965                 970                 975

Ser Glu Thr Thr Glu Asp Asp Ile Pro Phe Val Ala Thr Arg Gln Gly
            980                 985                 990

Glu Ser Ser Gly Asp Met Ala Trp  Glu Glu Val Arg Gly  Val Phe Arg
        995                 1000                1005

Val Ala  Ile Gln Pro Val Asn  Asp His Ala Pro Val  Gln Thr Ile
    1010                 1015                 1020

Ser Arg  Ile Phe His Val Ala  Arg Gly Gly Arg Arg  Leu Leu Thr
    1025                 1030                 1035

Thr Asp  Asp Val Ala Phe Ser  Asp Ala Asp Ser Gly  Phe Ala Asp
    1040                 1045                 1050

Ala Gln  Leu Val Leu Thr Arg  Lys Asp Leu Leu Phe  Gly Ser Ile
    1055                 1060                 1065

Val Ala  Val Asp Glu Pro Thr  Arg Pro Ile Tyr Arg  Phe Thr Gln
    1070                 1075                 1080

Glu Asp  Leu Arg Lys Arg Arg  Val Leu Phe Val His  Ser Gly Ala
    1085                 1090                 1095

Asp Arg  Gly Trp Ile Gln Leu  Gln Val Ser Asp Gly  Gln His Gln
    1100                 1105                 1110

Ala Thr  Ala Leu Leu Glu Val  Gln Ala Ser Glu Pro  Tyr Leu Arg
    1115                 1120                 1125

Val Ala  Asn Gly Ser Ser Leu  Val Val Pro Gln Gly  Gly Gln Gly
    1130                 1135                 1140

Thr Ile  Asp Thr Ala Val Leu  His Leu Asp Thr Asn  Leu Asp Ile
    1145                 1150                 1155

Arg Ser  Gly Asp Glu Val His  Tyr His Val Thr Ala  Gly Pro Arg
    1160                 1165                 1170

Trp Gly  Gln Leu Val Arg Ala  Gly Gln Pro Ala Thr  Ala Phe Ser
    1175                 1180                 1185

Gln Gln  Asp Leu Leu Asp Gly  Ala Val Leu Tyr Ser  His Asn Gly
    1190                 1195                 1200

Ser Leu  Ser Pro Arg Asp Thr  Met Ala Phe Ser Val  Glu Ala Gly
    1205                 1210                 1215

Pro Val  His Thr Asp Ala Thr  Leu Gln Val Thr Ile  Ala Leu Glu
    1220                 1225                 1230

Gly Pro  Leu Ala Pro Leu Lys  Leu Val Arg His Lys  Lys Ile Tyr
    1235                 1240                 1245

Val Phe  Gln Gly Glu Ala Ala  Glu Ile Arg Arg Asp  Gln Leu Glu
    1250                 1255                 1260

Ala Ala  Gln Glu Ala Val Pro  Pro Ala Asp Ile Val  Phe Ser Val
    1265                 1270                 1275

Lys Ser  Pro Pro Ser Ala Gly  Tyr Leu Val Met Val  Ser Arg Gly
    1280                 1285                 1290

Ala Leu  Ala Asp Glu Pro Pro  Ser Leu Asp Pro Val  Gln Ser Phe
    1295                 1300                 1305
```

-continued

Ser Gln Glu Ala Val Asp Thr Gly Arg Val Leu Tyr Leu His Ser
1310 1315 1320

Arg Pro Glu Ala Trp Ser Asp Ala Phe Ser Leu Asp Val Ala Ser
1325 1330 1335

Gly Leu Gly Ala Pro Leu Glu Gly Val Leu Val Glu Leu Glu Val
1340 1345 1350

Leu Pro Ala Ala Ile Pro Leu Glu Ala Gln Asn Phe Ser Val Pro
1355 1360 1365

Glu Gly Gly Ser Leu Thr Leu Ala Pro Pro Leu Leu Arg Val Ser
1370 1375 1380

Gly Pro Tyr Phe Pro Thr Leu Leu Gly Leu Ser Leu Gln Val Leu
1385 1390 1395

Glu Pro Pro Gln His Gly Ala Leu Gln Lys Glu Asp Gly Pro Gln
1400 1405 1410

Ala Arg Thr Leu Ser Ala Phe Ser Trp Arg Met Val Glu Glu Gln
1415 1420 1425

Leu Ile Arg Tyr Val His Asp Gly Ser Glu Thr Leu Thr Asp Ser
1430 1435 1440

Phe Val Leu Met Ala Asn Ala Ser Glu Met Asp Arg Gln Ser His
1445 1450 1455

Pro Val Ala Phe Thr Val Thr Val Leu Pro Val Asn Asp Gln Pro
1460 1465 1470

Pro Ile Leu Thr Thr Asn Thr Gly Leu Gln Met Trp Glu Gly Ala
1475 1480 1485

Thr Ala Pro Ile Pro Ala Glu Ala Leu Arg Ser Thr Asp Gly Asp
1490 1495 1500

Ser Gly Ser Glu Asp Leu Val Tyr Thr Ile Glu Gln Pro Ser Asn
1505 1510 1515

Gly Arg Val Val Leu Arg Gly Ala Pro Gly Thr Glu Val Arg Ser
1520 1525 1530

Phe Thr Gln Ala Gln Leu Asp Gly Gly Leu Val Leu Phe Ser His
1535 1540 1545

Arg Gly Thr Leu Asp Gly Gly Phe Arg Phe Arg Leu Ser Asp Gly
1550 1555 1560

Glu His Thr Ser Pro Gly His Phe Phe Arg Val Thr Ala Gln Lys
1565 1570 1575

Gln Val Leu Leu Ser Leu Lys Gly Ser Gln Thr Leu Thr Val Cys
1580 1585 1590

Pro Gly Ser Val Gln Pro Leu Ser Ser Gln Thr Leu Arg Ala Ser
1595 1600 1605

Ser Ser Ala Gly Thr Asp Pro Gln Leu Leu Leu Tyr Arg Val Val
1610 1615 1620

Arg Gly Pro Gln Leu Gly Arg Leu Phe His Ala Gln Gln Asp Ser
1625 1630 1635

Thr Gly Glu Ala Leu Val Asn Phe Thr Gln Ala Glu Val Tyr Ala
1640 1645 1650

Gly Asn Ile Leu Tyr Glu His Glu Met Pro Pro Glu Pro Phe Trp
1655 1660 1665

Glu Ala His Asp Thr Leu Glu Leu Gln Leu Ser Ser Pro Pro Ala
1670 1675 1680

Arg Asp Val Ala Ala Thr Leu Ala Val Ala Val Ser Phe Glu Ala
1685 1690 1695

-continued

```
Ala Cys  Pro Gln Arg Pro Ser  His Leu Trp Lys Asn  Lys Gly Leu
    1700                 1705                 1710

Trp Val  Pro Glu Gly Gln Arg  Ala Arg Ile Thr Val  Ala Ala Leu
    1715                 1720                 1725

Asp Ala  Ser Asn Leu Leu Ala  Ser Val Pro Ser Pro  Gln Arg Ser
    1730                 1735                 1740

Glu His  Asp Val Leu Phe Gln  Val Thr Gln Phe Pro  Ser Arg Gly
    1745                 1750                 1755

Gln Leu  Leu Val Ser Glu Glu  Pro Leu His Ala Gly  Gln Pro His
    1760                 1765                 1770

Phe Leu  Gln Ser Gln Leu Ala  Ala Gly Gln Leu Val  Tyr Ala His
    1775                 1780                 1785

Gly Gly  Gly Gly Thr Gln Gln  Asp Gly Phe His Phe  Arg Ala His
    1790                 1795                 1800

Leu Gln  Gly Pro Ala Gly Ala  Ser Val Ala Gly Pro  Gln Thr Ser
    1805                 1810                 1815

Glu Ala  Phe Ala Ile Thr Val  Arg Asp Val Asn Glu  Arg Pro Pro
    1820                 1825                 1830

Gln Pro  Gln Ala Ser Val Pro  Leu Arg Leu Thr Arg  Gly Ser Arg
    1835                 1840                 1845

Ala Pro  Ile Ser Arg Ala Gln  Leu Ser Val Val Asp  Pro Asp Ser
    1850                 1855                 1860

Ala Pro  Gly Glu Ile Glu Tyr  Glu Val Gln Arg Ala  Pro His Asn
    1865                 1870                 1875

Gly Phe  Leu Ser Leu Val Gly  Gly Gly Leu Gly Pro  Val Thr Arg
    1880                 1885                 1890

Phe Thr  Gln Ala Asp Val Asp  Ser Gly Arg Leu Ala  Phe Val Ala
    1895                 1900                 1905

Asn Gly  Ser Ser Val Ala Gly  Ile Phe Gln Leu Ser  Met Ser Asp
    1910                 1915                 1920

Gly Ala  Ser Pro Pro Leu Pro  Met Ser Leu Ala Val  Asp Ile Leu
    1925                 1930                 1935

Pro Ser  Ala Ile Glu Val Gln  Leu Arg Ala Pro Leu  Glu Val Pro
    1940                 1945                 1950

Gln Ala  Leu Gly Arg Ser Ser  Leu Ser Gln Gln Gln  Leu Arg Val
    1955                 1960                 1965

Val Ser  Asp Arg Glu Glu Pro  Glu Ala Ala Tyr Arg  Leu Ile Gln
    1970                 1975                 1980

Gly Pro  Gln Tyr Gly His Leu  Leu Val Gly Gly Arg  Pro Thr Ser
    1985                 1990                 1995

Ala Phe  Ser Gln Phe Gln Ile  Asp Gln Gly Glu Val  Val Phe Ala
    2000                 2005                 2010

Phe Thr  Asn Phe Ser Ser Ser  His Asp His Phe Arg  Val Leu Ala
    2015                 2020                 2025

Leu Ala  Arg Gly Val Asn Ala  Ser Ala Val Val Asn  Val Thr Val
    2030                 2035                 2040

Arg Ala  Leu Leu His Val Trp  Ala Gly Gly Pro Trp  Pro Gln Gly
    2045                 2050                 2055

Ala Thr  Leu Arg Leu Asp Pro  Thr Val Leu Asp Ala  Gly Glu Leu
    2060                 2065                 2070

Ala Asn  Arg Thr Gly Ser Val  Pro Arg Phe Arg Leu  Leu Glu Gly
    2075                 2080                 2085

Pro Arg  His Gly Arg Val Val  Arg Val Pro Arg Ala  Arg Thr Glu
```

```
    2090                2095                2100

Pro Gly  Gly Ser Gln Leu Val  Glu Gln Phe Thr Gln  Gln Asp Leu
    2105                2110                2115

Glu Asp  Gly Arg Leu Gly Leu  Glu Val Gly Arg Pro  Glu Gly Arg
    2120                2125                2130

Ala Pro  Gly Pro Ala Gly Asp  Ser Leu Thr Leu Glu  Leu Trp Ala
    2135                2140                2145

Gln Gly  Val Pro Pro Ala Val  Ala Ser Leu Asp Phe  Ala Thr Glu
    2150                2155                2160

Pro Tyr  Asn Ala Ala Arg Pro  Tyr Ser Val Ala Leu  Leu Ser Val
    2165                2170                2175

Pro Glu  Ala Ala Arg Thr Glu  Ala Gly Lys Pro Glu  Ser Ser Thr
    2180                2185                2190

Pro Thr  Gly Glu Pro Gly Pro  Met Ala Ser Ser Pro  Glu Pro Ala
    2195                2200                2205

Val Ala  Lys Gly Gly Phe Leu  Ser Phe Leu Glu Ala  Asn Met Phe
    2210                2215                2220

Ser Val  Ile Ile Pro Met Cys  Leu Val Leu Leu Leu  Leu Ala Leu
    2225                2230                2235

Ile Leu  Pro Leu Leu Phe Tyr  Leu Arg Lys Arg Asn  Lys Thr Gly
    2240                2245                2250

Lys His  Asp Val Gln Val Leu  Thr Ala Lys Pro Arg  Asn Gly Leu
    2255                2260                2265

Ala Gly  Asp Thr Glu Thr Phe  Arg Lys Val Glu Pro  Gly Gln Ala
    2270                2275                2280

Ile Pro  Leu Thr Ala Val Pro  Gly Gln Gly Pro Pro  Pro Gly Gly
    2285                2290                2295

Gln Pro  Asp Pro Glu Leu Leu  Gln Phe Cys Arg Thr  Pro Asn Pro
    2300                2305                2310

Ala Leu  Lys Asn Gly Gln Tyr Trp Val
    2315                2320


<210> SEQ ID NO 10
<211> LENGTH: 2222
<212> TYPE: PRT
<213> ORGANISM: Homo sapiens
<220> FEATURE:
<223> OTHER INFORMATION: CSPG4 [UniProtKB Q6UVK1]

<400> SEQUENCE: 10

Met Gln Ser Gly Pro Arg Pro Pro Leu Pro Ala Pro Gly Leu Ala Leu
1               5                   10                  15

Ala Leu Thr Leu Thr Met Leu Ala Arg Leu Ala Ser Ala Ala Ser Phe
            20                  25                  30

Phe Gly Glu Asn His Leu Glu Val Pro Val Ala Thr Ala Leu Thr Asp
        35                  40                  45

Ile Asp Leu Gln Leu Gln Phe Ser Thr Ser Gln Pro Glu Ala Leu Leu
    50                  55                  60

Leu Leu Ala Ala Gly Pro Ala Asp His Leu Leu Leu Gln Leu Tyr Ser
65                  70                  75                  80

Gly Arg Leu Gln Val Arg Leu Val Leu Gly Gln Glu Glu Leu Arg Leu
                85                  90                  95

Gln Thr Pro Ala Glu Thr Leu Leu Ser Asp Ser Ile Pro His Thr Val
            100                 105                 110

Val Leu Thr Val Val Glu Gly Trp Ala Thr Leu Ser Val Asp Gly Phe
```

-continued

```
        115                 120                 125
Leu Asn Ala Ser Ser Ala Val Pro Gly Ala Pro Leu Glu Val Pro Tyr
    130                 135                 140
Gly Leu Phe Val Gly Gly Thr Gly Thr Leu Gly Leu Pro Tyr Leu Arg
145                 150                 155                 160
Gly Thr Ser Arg Pro Leu Arg Gly Cys Leu His Ala Ala Thr Leu Asn
                165                 170                 175
Gly Arg Ser Leu Leu Arg Pro Leu Thr Pro Asp Val His Glu Gly Cys
            180                 185                 190
Ala Glu Glu Phe Ser Ala Ser Asp Asp Val Ala Leu Gly Phe Ser Gly
        195                 200                 205
Pro His Ser Leu Ala Ala Phe Pro Ala Trp Gly Thr Gln Asp Glu Gly
    210                 215                 220
Thr Leu Glu Phe Thr Leu Thr Thr Gln Ser Arg Gln Ala Pro Leu Ala
225                 230                 235                 240
Phe Gln Ala Gly Gly Arg Arg Gly Asp Phe Ile Tyr Val Asp Ile Phe
                245                 250                 255
Glu Gly His Leu Arg Ala Val Val Glu Lys Gly Gln Gly Thr Val Leu
            260                 265                 270
Leu His Asn Ser Val Pro Val Ala Asp Gly Gln Pro His Glu Val Ser
        275                 280                 285
Val His Ile Asn Ala His Arg Leu Glu Ile Ser Val Asp Gln Tyr Pro
    290                 295                 300
Thr His Thr Ser Asn Arg Gly Val Leu Ser Tyr Leu Glu Pro Arg Gly
305                 310                 315                 320
Ser Leu Leu Leu Gly Gly Leu Asp Ala Glu Ala Ser Arg His Leu Gln
                325                 330                 335
Glu His Arg Leu Gly Leu Thr Pro Glu Ala Thr Asn Ala Ser Leu Leu
            340                 345                 350
Gly Cys Met Glu Asp Leu Ser Val Asn Gly Gln Arg Arg Gly Leu Arg
        355                 360                 365
Glu Ala Leu Leu Thr Arg Asn Met Ala Ala Gly Cys Arg Leu Glu Glu
    370                 375                 380
Glu Glu Tyr Glu Asp Asp Ala Tyr Gly His Tyr Glu Ala Phe Ser Thr
385                 390                 395                 400
Leu Ala Pro Glu Ala Trp Pro Ala Met Glu Leu Pro Glu Pro Cys Val
                405                 410                 415
Pro Glu Pro Gly Leu Pro Pro Val Phe Ala Asn Phe Thr Gln Leu Leu
            420                 425                 430
Thr Ile Ser Pro Leu Val Val Ala Glu Gly Gly Thr Ala Trp Leu Glu
        435                 440                 445
Trp Arg His Val Gln Pro Thr Leu Asp Leu Met Glu Ala Glu Leu Arg
    450                 455                 460
Lys Ser Gln Val Leu Phe Ser Val Thr Arg Gly Ala Arg His Gly Glu
465                 470                 475                 480
Leu Glu Leu Asp Ile Pro Gly Ala Gln Ala Arg Lys Met Phe Thr Leu
                485                 490                 495
Leu Asp Val Val Asn Arg Lys Ala Arg Phe Ile His Asp Gly Ser Glu
            500                 505                 510
Asp Thr Ser Asp Gln Leu Val Leu Glu Val Ser Val Thr Ala Arg Val
        515                 520                 525
Pro Met Pro Ser Cys Leu Arg Arg Gly Gln Thr Tyr Leu Leu Pro Ile
    530                 535                 540
```

-continued

```
Gln Val Asn Pro Val Asn Asp Pro Pro His Ile Ile Phe Pro His Gly
545                 550                 555                 560

Ser Leu Met Val Ile Leu Glu His Thr Gln Lys Pro Leu Gly Pro Glu
                565                 570                 575

Val Phe Gln Ala Tyr Asp Pro Asp Ser Ala Cys Glu Gly Leu Thr Phe
            580                 585                 590

Gln Val Leu Gly Thr Ser Ser Gly Leu Pro Val Glu Arg Arg Asp Gln
        595                 600                 605

Pro Gly Glu Pro Ala Thr Glu Phe Ser Cys Arg Glu Leu Glu Ala Gly
    610                 615                 620

Ser Leu Val Tyr Val His Arg Gly Gly Pro Ala Gln Asp Leu Thr Phe
625                 630                 635                 640

Arg Val Ser Asp Gly Leu Gln Ala Ser Pro Pro Ala Thr Leu Lys Val
                645                 650                 655

Val Ala Ile Arg Pro Ala Ile Gln Ile His Arg Ser Thr Gly Leu Arg
            660                 665                 670

Leu Ala Gln Gly Ser Ala Met Pro Ile Leu Pro Ala Asn Leu Ser Val
        675                 680                 685

Glu Thr Asn Ala Val Gly Gln Asp Val Ser Val Leu Phe Arg Val Thr
    690                 695                 700

Gly Ala Leu Gln Phe Gly Glu Leu Gln Lys Gln Gly Ala Gly Gly Val
705                 710                 715                 720

Glu Gly Ala Glu Trp Trp Ala Thr Gln Ala Phe His Gln Arg Asp Val
                725                 730                 735

Glu Gln Gly Arg Val Arg Tyr Leu Ser Thr Asp Pro Gln His His Ala
            740                 745                 750

Tyr Asp Thr Val Glu Asn Leu Ala Leu Glu Val Gln Val Gly Gln Glu
        755                 760                 765

Ile Leu Ser Asn Leu Ser Phe Pro Val Thr Ile Gln Arg Ala Thr Val
    770                 775                 780

Trp Met Leu Arg Leu Glu Pro Leu His Thr Gln Asn Thr Gln Gln Glu
785                 790                 795                 800

Thr Leu Thr Thr Ala His Leu Glu Ala Thr Leu Glu Glu Ala Gly Pro
                805                 810                 815

Ser Pro Pro Thr Phe His Tyr Glu Val Val Gln Ala Pro Arg Lys Gly
            820                 825                 830

Asn Leu Gln Leu Gln Gly Thr Arg Leu Ser Asp Gly Gln Gly Phe Thr
        835                 840                 845

Gln Asp Asp Ile Gln Ala Gly Arg Val Thr Tyr Gly Ala Thr Ala Arg
    850                 855                 860

Ala Ser Glu Ala Val Glu Asp Thr Phe Arg Phe Arg Val Thr Ala Pro
865                 870                 875                 880

Pro Tyr Phe Ser Pro Leu Tyr Thr Phe Pro Ile His Ile Gly Gly Asp
                885                 890                 895

Pro Asp Ala Pro Val Leu Thr Asn Val Leu Leu Val Val Pro Glu Gly
            900                 905                 910

Gly Glu Gly Val Leu Ser Ala Asp His Leu Phe Val Lys Ser Leu Asn
        915                 920                 925

Ser Ala Ser Tyr Leu Tyr Glu Val Met Glu Arg Pro Arg His Gly Arg
    930                 935                 940

Leu Ala Trp Arg Gly Thr Gln Asp Lys Thr Thr Met Val Thr Ser Phe
945                 950                 955                 960
```

-continued

```
Thr Asn Glu Asp Leu Leu Arg Gly Arg Leu Val Tyr Gln His Asp Asp
                965                 970                 975

Ser Glu Thr Thr Glu Asp Asp Ile Pro Phe Val Ala Thr Arg Gln Gly
            980                 985                 990

Glu Ser Ser Gly Asp Met Ala Trp  Glu Glu Val Arg Gly  Val Phe Arg
        995                 1000                 1005

Val Ala  Ile Gln Pro Val Asn  Asp His Ala Pro Val  Gln Thr Ile
    1010                 1015                 1020

Ser Arg  Ile Phe His Val Ala  Arg Gly Gly Arg Arg  Leu Leu Thr
    1025                 1030                 1035

Thr Asp  Asp Val Ala Phe Ser  Asp Ala Asp Ser Gly  Phe Ala Asp
    1040                 1045                 1050

Ala Gln  Leu Val Leu Thr Arg  Lys Asp Leu Leu Phe  Gly Ser Ile
    1055                 1060                 1065

Val Ala  Val Asp Glu Pro Thr  Arg Pro Ile Tyr Arg  Phe Thr Gln
    1070                 1075                 1080

Glu Asp  Leu Arg Lys Arg Arg  Val Leu Phe Val His  Ser Gly Ala
    1085                 1090                 1095

Asp Arg  Gly Trp Ile Gln Leu  Gln Val Ser Asp Gly  Gln His Gln
    1100                 1105                 1110

Ala Thr  Ala Leu Leu Glu Val  Gln Ala Ser Glu Pro  Tyr Leu Arg
    1115                 1120                 1125

Val Ala  Asn Gly Ser Ser Leu  Val Val Pro Gln Gly  Gly Gln Gly
    1130                 1135                 1140

Thr Ile  Asp Thr Ala Val Leu  His Leu Asp Thr Asn  Leu Asp Ile
    1145                 1150                 1155

Arg Ser  Gly Asp Glu Val His  Tyr His Val Thr Ala  Gly Pro Arg
    1160                 1165                 1170

Trp Gly  Gln Leu Val Arg Ala  Gly Gln Pro Ala Thr  Ala Phe Ser
    1175                 1180                 1185

Gln Gln  Asp Leu Leu Asp Gly  Ala Val Leu Tyr Ser  His Asn Gly
    1190                 1195                 1200

Ser Leu  Ser Pro Arg Asp Thr  Met Ala Phe Ser Val  Glu Ala Gly
    1205                 1210                 1215

Pro Val  His Thr Asp Ala Thr  Leu Gln Val Thr Ile  Ala Leu Glu
    1220                 1225                 1230

Gly Pro  Leu Ala Pro Leu Lys  Leu Val Arg His Lys  Lys Ile Tyr
    1235                 1240                 1245

Val Phe  Gln Gly Glu Ala Ala  Glu Ile Arg Arg Asp  Gln Leu Glu
    1250                 1255                 1260

Ala Ala  Gln Glu Ala Val Pro  Pro Ala Asp Ile Val  Phe Ser Val
    1265                 1270                 1275

Lys Ser  Pro Pro Ser Ala Gly  Tyr Leu Val Met Val  Ser Arg Gly
    1280                 1285                 1290

Ala Leu  Ala Asp Glu Pro Pro  Ser Leu Asp Pro Val  Gln Ser Phe
    1295                 1300                 1305

Ser Gln  Glu Ala Val Asp Thr  Gly Arg Val Leu Tyr  Leu His Ser
    1310                 1315                 1320

Arg Pro  Glu Ala Trp Ser Asp  Ala Phe Ser Leu Asp  Val Ala Ser
    1325                 1330                 1335

Gly Leu  Gly Ala Pro Leu Glu  Gly Val Leu Val Glu  Leu Glu Val
    1340                 1345                 1350

Leu Pro  Ala Ala Ile Pro Leu  Glu Ala Gln Asn Phe  Ser Val Pro
```

-continued

```
    1355                1360                1365

Glu Gly Gly Ser Leu Thr Leu Ala Pro Pro Leu Leu Arg Val Ser
    1370                1375                1380

Gly Pro Tyr Phe Pro Thr Leu Leu Gly Leu Ser Leu Gln Val Leu
    1385                1390                1395

Glu Pro Pro Gln His Gly Ala Leu Gln Lys Glu Asp Gly Pro Gln
    1400                1405                1410

Ala Arg Thr Leu Ser Ala Phe Ser Trp Arg Met Val Glu Glu Gln
    1415                1420                1425

Leu Ile Arg Tyr Val His Asp Gly Ser Glu Thr Leu Thr Asp Ser
    1430                1435                1440

Phe Val Leu Met Ala Asn Ala Ser Glu Met Asp Arg Gln Ser His
    1445                1450                1455

Pro Val Ala Phe Thr Val Thr Val Leu Pro Val Asn Asp Gln Pro
    1460                1465                1470

Pro Ile Leu Thr Thr Asn Thr Gly Leu Gln Met Trp Glu Gly Ala
    1475                1480                1485

Thr Ala Pro Ile Pro Ala Glu Ala Leu Arg Ser Thr Asp Gly Asp
    1490                1495                1500

Ser Gly Ser Glu Asp Leu Val Tyr Thr Ile Glu Gln Pro Ser Asn
    1505                1510                1515

Gly Arg Val Val Leu Arg Gly Ala Pro Gly Thr Glu Val Arg Ser
    1520                1525                1530

Phe Thr Gln Ala Gln Leu Asp Gly Gly Leu Val Leu Phe Ser His
    1535                1540                1545

Arg Gly Thr Leu Asp Gly Gly Phe Arg Phe Arg Leu Ser Asp Gly
    1550                1555                1560

Glu His Thr Ser Pro Gly His Phe Phe Arg Val Thr Ala Gln Lys
    1565                1570                1575

Gln Val Leu Leu Ser Leu Lys Gly Ser Gln Thr Leu Thr Val Cys
    1580                1585                1590

Pro Gly Ser Val Gln Pro Leu Ser Ser Gln Thr Leu Arg Ala Ser
    1595                1600                1605

Ser Ser Ala Gly Thr Asp Pro Gln Leu Leu Leu Tyr Arg Val Val
    1610                1615                1620

Arg Gly Pro Gln Leu Gly Arg Leu Phe His Ala Gln Gln Asp Ser
    1625                1630                1635

Thr Gly Glu Ala Leu Val Asn Phe Thr Gln Ala Glu Val Tyr Ala
    1640                1645                1650

Gly Asn Ile Leu Tyr Glu His Glu Met Pro Pro Glu Pro Phe Trp
    1655                1660                1665

Glu Ala His Asp Thr Leu Glu Leu Gln Leu Ser Ser Pro Pro Ala
    1670                1675                1680

Arg Asp Val Ala Ala Thr Leu Ala Val Ala Val Ser Phe Glu Ala
    1685                1690                1695

Ala Cys Pro Gln Arg Pro Ser His Leu Trp Lys Asn Lys Gly Leu
    1700                1705                1710

Trp Val Pro Glu Gly Gln Arg Ala Arg Ile Thr Val Ala Ala Leu
    1715                1720                1725

Asp Ala Ser Asn Leu Leu Ala Ser Val Pro Ser Pro Gln Arg Ser
    1730                1735                1740

Glu His Asp Val Leu Phe Gln Val Thr Gln Phe Pro Ser Arg Gly
    1745                1750                1755
```

-continued

```
Gln Leu  Leu Val Ser Glu Glu  Pro Leu His Ala Gly  Gln Pro His
    1760                 1765                 1770

Phe Leu  Gln Ser Gln Leu Ala  Ala Gly Gln Leu Val  Tyr Ala His
    1775                 1780                 1785

Gly Gly  Gly Gly Thr Gln Gln  Asp Gly Phe His Phe  Arg Ala His
    1790                 1795                 1800

Leu Gln  Gly Pro Ala Gly Ala  Ser Val Ala Gly Pro  Gln Thr Ser
    1805                 1810                 1815

Glu Ala  Phe Ala Ile Thr Val  Arg Asp Val Asn Glu  Arg Pro Pro
    1820                 1825                 1830

Gln Pro  Gln Ala Ser Val Pro  Leu Arg Leu Thr Arg  Gly Ser Arg
    1835                 1840                 1845

Ala Pro  Glu Val Pro Gln Ala  Leu Gly Arg Ser Ser  Leu Ser Gln
    1850                 1855                 1860

Gln Gln  Leu Arg Val Val Ser  Asp Arg Glu Glu Pro  Glu Ala Ala
    1865                 1870                 1875

Tyr Arg  Leu Ile Gln Gly Pro  Gln Tyr Gly His Leu  Leu Val Gly
    1880                 1885                 1890

Gly Arg  Pro Thr Ser Ala Phe  Ser Gln Phe Gln Ile  Asp Gln Gly
    1895                 1900                 1905

Glu Val  Val Phe Ala Phe Thr  Asn Phe Ser Ser Ser  His Asp His
    1910                 1915                 1920

Phe Arg  Val Leu Ala Leu Ala  Arg Gly Val Asn Ala  Ser Ala Val
    1925                 1930                 1935

Val Asn  Val Thr Val Arg Ala  Leu Leu His Val Trp  Ala Gly Gly
    1940                 1945                 1950

Pro Trp  Pro Gln Gly Ala Thr  Leu Arg Leu Asp Pro  Thr Val Leu
    1955                 1960                 1965

Asp Ala  Gly Glu Leu Ala Asn  Arg Thr Gly Ser Val  Pro Arg Phe
    1970                 1975                 1980

Arg Leu  Leu Glu Gly Pro Arg  His Gly Arg Val Val  Arg Val Pro
    1985                 1990                 1995

Arg Ala  Arg Thr Glu Pro Gly  Gly Ser Gln Leu Val  Glu Gln Phe
    2000                 2005                 2010

Thr Gln  Gln Asp Leu Glu Asp  Gly Arg Leu Gly Leu  Glu Val Gly
    2015                 2020                 2025

Arg Pro  Glu Gly Arg Ala Pro  Gly Pro Ala Gly Asp  Ser Leu Thr
    2030                 2035                 2040

Leu Glu  Leu Trp Ala Gln Gly  Val Pro Pro Ala Val  Ala Ser Leu
    2045                 2050                 2055

Asp Phe  Ala Thr Glu Pro Tyr  Asn Ala Ala Arg Pro  Tyr Ser Val
    2060                 2065                 2070

Ala Leu  Leu Ser Val Pro Glu  Ala Ala Arg Thr Glu  Ala Gly Lys
    2075                 2080                 2085

Pro Glu  Ser Ser Thr Pro Thr  Gly Glu Pro Gly Pro  Met Ala Ser
    2090                 2095                 2100

Ser Pro  Glu Pro Ala Val Ala  Lys Gly Gly Phe Leu  Ser Phe Leu
    2105                 2110                 2115

Glu Ala  Asn Met Phe Ser Val  Ile Ile Pro Met Cys  Leu Val Leu
    2120                 2125                 2130

Leu Leu  Leu Ala Leu Ile Leu  Pro Leu Leu Phe Tyr  Leu Arg Lys
    2135                 2140                 2145
```

-continued

```
Arg Asn  Lys Thr Gly Lys His  Asp Val Gln Val Leu  Thr Ala Lys
    2150                 2155                 2160

Pro Arg  Asn Gly Leu Ala Gly  Asp Thr Glu Thr Phe  Arg Lys Val
    2165                 2170                 2175

Glu Pro  Gly Gln Ala Ile Pro  Leu Thr Ala Val Pro  Gly Gln Gly
    2180                 2185                 2190

Pro Pro  Pro Gly Gly Gln Pro  Asp Pro Glu Leu Leu  Gln Phe Cys
    2195                 2200                 2205

Arg Thr  Pro Asn Pro Ala Leu  Lys Asn Gly Gln Tyr  Trp Val
    2210                 2215                 2220
```

<210> SEQ ID NO 11
<211> LENGTH: 11
<212> TYPE: PRT
<213> ORGANISM: Artificial Sequence
<220> FEATURE:
<223> OTHER INFORMATION: Synthetic sequence ARD107 VH CDR1

<400> SEQUENCE: 11

```
Gly Tyr Ser Ile Thr Ser Gly Tyr Tyr Trp Asn
1               5                   10
```

<210> SEQ ID NO 12
<211> LENGTH: 16
<212> TYPE: PRT
<213> ORGANISM: Artificial Sequence
<220> FEATURE:
<223> OTHER INFORMATION: Synthetic sequence ARD107 VH CDR2

<400> SEQUENCE: 12

```
Tyr Ile Thr Tyr Asp Gly Ser Asn Asn Tyr Asn Pro Ser Leu Lys Asn
1               5                   10                  15
```

<210> SEQ ID NO 13
<211> LENGTH: 3
<212> TYPE: PRT
<213> ORGANISM: Artificial Sequence
<220> FEATURE:
<223> OTHER INFORMATION: Synthetic sequence ARD107 VH CDR3

<400> SEQUENCE: 13

```
Phe Asp Tyr
1
```

<210> SEQ ID NO 14
<211> LENGTH: 11
<212> TYPE: PRT
<213> ORGANISM: Artificial Sequence
<220> FEATURE:
<223> OTHER INFORMATION: Synthetic sequence ARD107 VL CDR1

<400> SEQUENCE: 14

```
Ser Ala Ser Gln Gly Ile Arg Asn Tyr Leu Asn
1               5                   10
```

<210> SEQ ID NO 15
<211> LENGTH: 7
<212> TYPE: PRT
<213> ORGANISM: Artificial Sequence
<220> FEATURE:
<223> OTHER INFORMATION: Synthetic sequence ARD107 VL CDR2

<400> SEQUENCE: 15

```
Tyr Thr Ser Ser Leu His Ser
1               5
```

<210> SEQ ID NO 16
<211> LENGTH: 9
<212> TYPE: PRT
<213> ORGANISM: Artificial Sequence
<220> FEATURE:
<223> OTHER INFORMATION: Synthetic sequence ARD107 VL CDR3

<400> SEQUENCE: 16

Gln Gln Tyr Ser Lys Leu Pro Trp Thr
1               5

<210> SEQ ID NO 17
<211> LENGTH: 25
<212> TYPE: PRT
<213> ORGANISM: Artificial Sequence
<220> FEATURE:
<223> OTHER INFORMATION: Synthetic sequence linker
<220> FEATURE:
<221> NAME/KEY: VARIANT
<222> LOCATION: (6)...(25)
<223> OTHER INFORMATION: amino acids 6-25, 11-25, 16-25,
      or 21-25 may be present or absent

<400> SEQUENCE: 17

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 18
<211> LENGTH: 6
<212> TYPE: PRT
<213> ORGANISM: Artificial Sequence
<220> FEATURE:
<223> OTHER INFORMATION: Synthetic sequence hexahistidinyl tag

<400> SEQUENCE: 18

His His His His His His
1               5

<210> SEQ ID NO 19
<211> LENGTH: 1329
<212> TYPE: DNA
<213> ORGANISM: Artificial Sequence
<220> FEATURE:
<223> OTHER INFORMATION: Synthetic sequence ARD107 Coding Sequence for
      VH and IgG1

<400> SEQUENCE: 19
gaggtccagc tgcaggagtc aggacctggc ctcgtgaaac cttctcagtc tctgtctctc     60
acctgctctg tcactggcta ctccatcacc agtggttatt actggaactg gatccggcag    120
tttccaggaa acaagctgga atggatgggc tacataacct acgacggtag caataactac    180
aacccatctc tcaaaaatcg aatctccatc actcgtgaca catctaagaa ccagtttttc    240
ctgaagttga attctgtgac tactgaggac acagctacat attactgtgc ggactttgac    300
tactggggcc aaggcaccac tctcacagtc tcctcagcta gcaccaaggg cccatcggtc    360
ttccccctgg caccctcctc caagagcacc tctgggggca cagcggccct gggctgcctg    420
gtcaaggact acttccccga accggtgacg gtgtcgtgga actcaggcgc cctgaccagc    480
ggcgtgcaca ccttcccggc tgtcctacag tcctcaggac tctactccct cagcagcgtg    540
gtgaccgtgc cctccagcag cttgggcacc cagacctaca tctgcaacgt gaatcacaag    600

-continued cccagcaaca ccaaggtgga caagaaagtt gagcccaaat cttgtgacaa aactcacaca 660
tgcccaccgt gcccagcacc tgaactcctg gggggaccgt cagtcttcct cttcccccca 720
aaacccaagg acaccctcat gatctcccgg acccctgagg tcacatgcgt ggtggtggac 780
gtgagccacg aagaccctga ggtcaagttc aactggtacg tggacggcgt ggaggtgcat 840
aatgccaaga caaagccgcg ggaggagcag tacaacagca cgtaccgtgt ggtcagcgtc 900
ctcaccgtcc tgcaccagga ctggctgaat ggcaaggagt acaagtgcaa ggtctccaac 960
aaagccctcc cagcccccat cgagaaaacc atctccaaag ccaaagggca gccccgagaa 1020
ccacaggtgt acaccctgcc cccatcccgg gatgagctga ccaagaacca ggtcagcctg 1080
acctgcctgg tcaaaggctt ctatcccagc gacatcgccg tggagtggga gagcaatggg 1140
cagccggaga acaactacaa gaccacgcct cccgtgctgg actccgacgg ctccttcttc 1200
ctctacagca agctcaccgt ggacaagagc aggtggcagc aggggaacgt cttctcatgc 1260
tccgtgatgc atgaggctct gcacaaccac tacacgcaga agagcctctc cctgtctccg 1320
ggtaaatga 1329

<210> SEQ ID NO 20
<211> LENGTH: 645
<212> TYPE: DNA
<213> ORGANISM: Artificial Sequence
<220> FEATURE:
<223> OTHER INFORMATION: Synthetic sequence Coding Sequence for ARD107
VL and Igkappa

<400> SEQUENCE: 20
gatattgtgc tcacacagtc tccatcctcc ctgtctgcct ctctgggaga cagagtcacc 60
atcagttgca gtgcaagtca gggcattaga aattatttaa actggtatca gcagagacca 120
gatggaactg ttaaactcct gatctattac acatcaagtt tacactcagg agtcccatca 180
aggttcagtg gcagtgggtc tgggacagat tattctctca ccatcagcaa cctggaacct 240
gaagatattg ccacttacta ttgtcagcag tatagtaagc ttccttggac gttcggtgga 300
ggcaccaagc tggaaatcaa acgtacggtg gctgcaccat ctgtcttcat cttcccgcca 360
tctgatgagc agttgaaatc tggaactgcc tctgttgtgt gcctgctgaa taacttctat 420
cccagagagg ccaaagtaca gtggaaggtg gataacgccc tccaatcggg taactcccag 480
gagagtgtca cagagcagga cagcaaggac agcacctaca gcctcagcag caccctgacg 540
ctgagcaaag cagactacga gaaacacaaa gtctacgcct gcgaagtcac ccatcagggc 600
ctgagctcgc ccgtcacaaa gagcttcaac aggggagagt gttag 645

<210> SEQ ID NO 21
<211> LENGTH: 336
<212> TYPE: DNA
<213> ORGANISM: Artificial Sequence
<220> FEATURE:
<223> OTHER INFORMATION: Synthetic sequence ARD107 VH Coding Region

<400> SEQUENCE: 21
gaggtccagc tgcaggagtc aggacctggc ctcgtgaaac cttctcagtc tctgtctctc 60
acctgctctg tcactggcta ctccatcacc agtggttatt actggaactg gatccggcag 120
tttccaggaa acaagctgga atggatgggc tacataacct acgacggtag caataactac 180
aacccatctc tcaaaaatcg aatctccatc actcgtgaca catctaagaa ccagtttttc 240
ctgaagttga attctgtgac tactgaggac acagctacat attactgtgc ggactttgac 300

-continued

```
tactggggcc aaggcaccac tctcacagtc tcctca                          336


<210> SEQ ID NO 22
<211> LENGTH: 321
<212> TYPE: DNA
<213> ORGANISM: Artificial Sequence
<220> FEATURE:
<223> OTHER INFORMATION: Synthetic sequence ARD107 VL Coding Region

<400> SEQUENCE: 22

gatattgtgc tcacacagtc tccatcctcc ctgtctgcct ctctgggaga cagagtcacc     60

atcagttgca gtgcaagtca gggcattaga aattatttaa actggtatca gcagagacca    120

gatggaactg ttaaactcct gatctattac acatcaagtt tacactcagg agtcccatca    180

aggttcagtg gcagtgggtc tgggacagat tattctctca ccatcagcaa cctggaacct    240

gaagatattg ccacttacta ttgtcagcag tatagtaagc ttccttggac gttcggtgga    300

ggcaccaagc tggaaatcaa a                                              321


<210> SEQ ID NO 23
<211> LENGTH: 57
<212> TYPE: DNA
<213> ORGANISM: Artificial Sequence
<220> FEATURE:
<223> OTHER INFORMATION: Synthetic sequence VH signal sequence

<400> SEQUENCE: 23

atggagtttg ggctgagctg gctttttctt gtcgcgattc ttaagggtgt ccaatgc        57


<210> SEQ ID NO 24
<211> LENGTH: 66
<212> TYPE: DNA
<213> ORGANISM: Artificial Sequence
<220> FEATURE:
<223> OTHER INFORMATION: Synthetic sequence VL signal sequence

<400> SEQUENCE: 24

atggacatgc gcgtgcccgc ccagctgctg ggcctgctgc tgctgtggtt ccccggatcc     60

cgatgc                                                                66


<210> SEQ ID NO 25
<211> LENGTH: 112
<212> TYPE: PRT
<213> ORGANISM: Artificial Sequence
<220> FEATURE:
<223> OTHER INFORMATION: Synthetic sequence humanized ARD107 VH1

<400> SEQUENCE: 25

Glu Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Thr Ser Gly
            20                  25                  30

Tyr Tyr Trp Asn Trp Ile Arg Gln Phe Pro Gly Asn Lys Leu Glu Trp
        35                  40                  45

Met Gly Tyr Ile Thr Tyr Asp Gly Ser Asn Asn Tyr Asn Pro Ser Leu
    50                  55                  60

Lys Asn Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Asp Phe Asp Tyr Trp Gly Gln Gly Thr Thr Val Thr Val Ser Ser
```

100 105 110

<210> SEQ ID NO 26
<211> LENGTH: 112
<212> TYPE: PRT
<213> ORGANISM: Artificial Sequence
<220> FEATURE:
<223> OTHER INFORMATION: Synthetic sequence humanized ARD107 VH2

<400> SEQUENCE: 26

Glu Val Gln Leu Gln Glu Ser Gly Pro Gly Leu Val Lys Pro Ser Gln
1 5 10 15

Thr Leu Ser Leu Thr Cys Thr Val Ser Gly Tyr Ser Ile Thr Ser Gly
20 25 30

Tyr Tyr Trp Asn Trp Ile Arg Gln Phe Pro Gly Asn Lys Leu Glu Trp
35 40 45

Met Gly Tyr Ile Thr Tyr Asp Gly Ser Asn Asn Tyr Asn Pro Ser Leu
50 55 60

Lys Asn Arg Val Thr Ile Ser Arg Asp Thr Ser Lys Asn Gln Phe Ser
65 70 75 80

Leu Lys Leu Ser Ser Val Thr Ala Glu Asp Thr Ala Val Tyr Tyr Cys
85 90 95

Ala Asp Phe Asp Tyr Trp Gly Gln Gly Thr Thr Leu Thr Val Ser Ser
100 105 110

<210> SEQ ID NO 27
<211> LENGTH: 112
<212> TYPE: PRT
<213> ORGANISM: Artificial Sequence
<220> FEATURE:
<223> OTHER INFORMATION: Synthetic sequence humanized ARD107 VH3

<400> SEQUENCE: 27

Glu Val Gln Leu Gln Glu Ser Gly Pro Gly Leu Val Lys Pro Ser Gln
1 5 10 15

Thr Leu Ser Leu Thr Cys Thr Val Ser Gly Tyr Ser Ile Thr Ser Gly
20 25 30

Tyr Tyr Trp Asn Trp Ile Arg Gln Phe Pro Gly Asn Lys Leu Glu Trp
35 40 45

Met Gly Tyr Ile Thr Tyr Asp Gly Ser Asn Asn Tyr Asn Pro Ser Leu
50 55 60

Lys Asn Arg Ile Thr Ile Ser Arg Asp Thr Ser Lys Asn Gln Phe Phe
65 70 75 80

Leu Lys Leu Ser Ser Val Thr Ala Ala Asp Thr Ala Val Tyr Tyr Cys
85 90 95

Ala Asp Phe Asp Tyr Trp Gly Gln Gly Thr Thr Val Thr Val Ser Ser
100 105 110

<210> SEQ ID NO 28
<211> LENGTH: 112
<212> TYPE: PRT
<213> ORGANISM: Artificial Sequence
<220> FEATURE:
<223> OTHER INFORMATION: Synthetic sequence humanized ARD107 VH4

<400> SEQUENCE: 28

Glu Val Gln Leu Gln Glu Ser Gly Pro Gly Leu Val Lys Pro Ser Gln
1 5 10 15

Thr Leu Ser Leu Thr Cys Thr Val Ser Gly Tyr Ser Ile Thr Ser Gly
20 25 30

-continued

```
Tyr Tyr Trp Asn Trp Ile Arg Gln Phe Pro Gly Asn Lys Leu Glu Trp
        35                  40                  45

Met Gly Tyr Ile Thr Tyr Asp Gly Ser Asn Asn Tyr Asn Pro Ser Leu
    50                  55                  60

Lys Asn Arg Ile Thr Ile Ser Arg Asp Thr Ser Lys Asn Gln Phe Phe
65                  70                  75                  80

Leu Lys Leu Ser Ser Val Thr Ala Glu Asp Thr Ala Val Tyr Tyr Cys
                85                  90                  95

Ala Asp Phe Asp Tyr Trp Gly Gln Gly Thr Thr Leu Thr Val Ser Ser
            100                 105                 110


<210> SEQ ID NO 29
<211> LENGTH: 107
<212> TYPE: PRT
<213> ORGANISM: Artificial Sequence
<220> FEATURE:
<223> OTHER INFORMATION: Synthetic sequence humanized ARD107 VL1

<400> SEQUENCE: 29

Asp Ile Gln Leu Thr Gln Ser Pro Ser Ser Leu Ser Ala Ser Val Gly
1               5                   10                  15

Asp Arg Val Thr Ile Thr Cys Ser Ala Ser Gln Gly Ile Arg Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Lys Leu Pro Trp
                85                  90                  95

Thr Phe Gly Gly Gly Thr Lys Leu Glu Ile Lys
            100                 105


<210> SEQ ID NO 30
<211> LENGTH: 107
<212> TYPE: PRT
<213> ORGANISM: Artificial Sequence
<220> FEATURE:
<223> OTHER INFORMATION: Synthetic sequence humanized ARD107 VL2

<400> SEQUENCE: 30

Asp Ile Gln Leu Thr Gln Ser Pro Ser Ser Leu Ser Ala Ser Val Gly
1               5                   10                  15

Asp Arg Val Thr Ile Thr Cys Ser Ala Ser Gln Gly Ile Arg Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Ser Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Tyr Ser Lys Leu Pro Trp
                85                  90                  95

Thr Phe Gly Gly Gly Thr Lys Leu Glu Ile Lys
            100                 105
```

<210> SEQ ID NO 31
<211> LENGTH: 107
<212> TYPE: PRT
<213> ORGANISM: Artificial Sequence
<220> FEATURE:
<223> OTHER INFORMATION: Synthetic sequence humanized ARD107 VL3

<400> SEQUENCE: 31

```
Asp Ile Gln Leu Thr Gln Ser Pro Ser Ser Leu Ser Ala Ser Val Gly
1               5                   10                  15

Asp Arg Val Thr Ile Thr Cys Ser Ala Ser Gln Gly Ile Arg Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Thr Tyr Tyr Cys Gln Gln Tyr Ser Lys Leu Pro Trp
                85                  90                  95

Thr Phe Gly Gly Gly Thr Lys Leu Glu Ile Lys
            100                 105
```

<210> SEQ ID NO 32
<211> LENGTH: 107
<212> TYPE: PRT
<213> ORGANISM: Artificial Sequence
<220> FEATURE:
<223> OTHER INFORMATION: Synthetic sequence humanized ARD107 VL4

<400> SEQUENCE: 32

```
Asp Ile Val Leu Thr Gln Ser Pro Ser Ser Leu Ser Ala Ser Val Gly
1               5                   10                  15

Asp Arg Val Thr Ile Thr Cys Ser Ala Ser Gln Gly Ile Arg Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Ser Leu His Ser Gly Val Pro Ser Arg Phe Ser Gly
    50                  55                  60

Ser Gly Ser Gly Thr Asp Tyr Thr Leu Thr Ile Ser Ser Leu Glu Pro
65                  70                  75                  80

Glu Asp Ile Ala Thr Tyr Tyr Cys Gln Gln Tyr Ser Lys Leu Pro Trp
                85                  90                  95

Thr Phe Gly Gly Gly Thr Lys Leu Glu Ile Lys
            100                 105
```

<210> SEQ ID NO 33
<211> LENGTH: 442
<212> TYPE: PRT
<213> ORGANISM: Artificial Sequence
<220> FEATURE:
<223> OTHER INFORMATION: Synthetic sequence humanized ARD107 H1 heavy
      chain

<400> SEQUENCE: 33

```
Glu Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Thr Ser Gly
            20                  25                  30

Tyr Tyr Trp Asn Trp Ile Arg Gln Phe Pro Gly Asn Lys Leu Glu Trp
```

```
        35                  40                  45

Met Gly Tyr Ile Thr Tyr Asp Gly Ser Asn Asn Tyr Asn Pro Ser Leu
    50                  55                  60

Lys Asn Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Asp Phe Asp Tyr Trp Gly Gln Gly Thr Thr Val Thr Val Ser Ser
            100                 105                 110

Ala Ser Thr Lys Gly Pro Ser Val Phe Pro Leu Ala Pro Ser Ser Lys
        115                 120                 125

Ser Thr Ser Gly Gly Thr Ala Ala Leu Gly Cys Leu Val Lys Asp Tyr
    130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175

Leu Ser Ser Val Val Thr Val Pro Ser Ser Ser Leu Gly Thr Gln Thr
            180                 185                 190

Tyr Ile Cys Asn Val Asn His Lys Pro Ser Asn Thr Lys Val Asp Lys
        195                 200                 205

Lys Val Glu Pro Lys Ser Cys Asp Lys Thr His Thr Cys Pro Pro Cys
    210                 215                 220

Pro Ala Pro Glu Leu Leu Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser His Glu Asp Pro Glu Val Lys Phe Asn Trp
            260                 265                 270

Tyr Val Asp Gly Val Glu Val His Asn Ala Lys Thr Lys Pro Arg Glu
        275                 280                 285

Glu Gln Tyr Asn Ser Thr Tyr Arg Val Val Ser Val Leu Thr Val Leu
    290                 295                 300

His Gln Asp Trp Leu Asn Gly Lys Glu Tyr Lys Cys Lys Val Ser Asn
305                 310                 315                 320

Lys Ala Leu Pro Ala Pro Ile Glu Lys Thr Ile Ser Lys Ala Lys Gly
                325                 330                 335

Gln Pro Arg Glu Pro Gln Val Tyr Thr Leu Pro Pro Ser Arg Asp Glu
            340                 345                 350

Leu Thr Lys Asn Gln Val Ser Leu Thr Cys Leu Val Lys Gly Phe Tyr
        355                 360                 365

Pro Ser Asp Ile Ala Val Glu Trp Glu Ser Asn Gly Gln Pro Glu Asn
    370                 375                 380

Asn Tyr Lys Thr Thr Pro Pro Val Leu Asp Ser Asp Gly Ser Phe Phe
385                 390                 395                 400

Leu Tyr Ser Lys Leu Thr Val Asp Lys Ser Arg Trp Gln Gln Gly Asn
                405                 410                 415

Val Phe Ser Cys Ser Val Met His Glu Ala Leu His Asn His Tyr Thr
            420                 425                 430

Gln Lys Ser Leu Ser Leu Ser Pro Gly Lys
        435                 440
```

<210> SEQ ID NO 34

<211> LENGTH: 442
<212> TYPE: PRT
<213> ORGANISM: Artificial Sequence
<220> FEATURE:
<223> OTHER INFORMATION: Synthetic sequence humanized ARD107 H2 heavy chain

<400> SEQUENCE: 34

```
Glu Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Thr Ser Gly
            20                  25                  30

Tyr Tyr Trp Asn Trp Ile Arg Gln Phe Pro Gly Asn Lys Leu Glu Trp
        35                  40                  45

Met Gly Tyr Ile Thr Tyr Asp Gly Ser Asn Asn Tyr Asn Pro Ser Leu
    50                  55                  60

Lys Asn Arg Val Thr Ile Ser Arg Asp Thr Ser Lys Asn Gln Phe Ser
65                  70                  75                  80

Leu Lys Leu Ser Ser Val Thr Ala Glu Asp Thr Ala Val Tyr Tyr Cys
                85                  90                  95

Ala Asp Phe Asp Tyr Trp Gly Gln Gly Thr Thr Leu Thr Val Ser Ser
            100                 105                 110

Ala Ser Thr Lys Gly Pro Ser Val Phe Pro Leu Ala Pro Ser Ser Lys
        115                 120                 125

Ser Thr Ser Gly Gly Thr Ala Ala Leu Gly Cys Leu Val Lys Asp Tyr
    130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175

Leu Ser Ser Val Val Thr Val Pro Ser Ser Ser Leu Gly Thr Gln Thr
            180                 185                 190

Tyr Ile Cys Asn Val Asn His Lys Pro Ser Asn Thr Lys Val Asp Lys
        195                 200                 205

Lys Val Glu Pro Lys Ser Cys Asp Lys Thr His Thr Cys Pro Pro Cys
    210                 215                 220

Pro Ala Pro Glu Leu Leu Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser His Glu Asp Pro Glu Val Lys Phe Asn Trp
            260                 265                 270

Tyr Val Asp Gly Val Glu Val His Asn Ala Lys Thr Lys Pro Arg Glu
        275                 280                 285

Glu Gln Tyr Asn Ser Thr Tyr Arg Val Val Ser Val Leu Thr Val Leu
    290                 295                 300

His Gln Asp Trp Leu Asn Gly Lys Glu Tyr Lys Cys Lys Val Ser Asn
305                 310                 315                 320

Lys Ala Leu Pro Ala Pro Ile Glu Lys Thr Ile Ser Lys Ala Lys Gly
                325                 330                 335

Gln Pro Arg Glu Pro Gln Val Tyr Thr Leu Pro Pro Ser Arg Asp Glu
            340                 345                 350

Leu Thr Lys Asn Gln Val Ser Leu Thr Cys Leu Val Lys Gly Phe Tyr
        355                 360                 365

Pro Ser Asp Ile Ala Val Glu Trp Glu Ser Asn Gly Gln Pro Glu Asn
```

-continued

```
    370                 375                 380

Asn Tyr Lys Thr Thr Pro Pro Val Leu Asp Ser Asp Gly Ser Phe Phe
385                 390                 395                 400

Leu Tyr Ser Lys Leu Thr Val Asp Lys Ser Arg Trp Gln Gln Gly Asn
                405                 410                 415

Val Phe Ser Cys Ser Val Met His Glu Ala Leu His Asn His Tyr Thr
            420                 425                 430

Gln Lys Ser Leu Ser Leu Ser Pro Gly Lys
        435                 440


<210> SEQ ID NO 35
<211> LENGTH: 442
<212> TYPE: PRT
<213> ORGANISM: Artificial Sequence
<220> FEATURE:
<223> OTHER INFORMATION: Synthetic sequence humanized ARD107 H3 heavy
      chain

<400> SEQUENCE: 35

Glu Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Thr Ser Gly
            20                  25                  30

Tyr Tyr Trp Asn Trp Ile Arg Gln Phe Pro Gly Asn Lys Leu Glu Trp
        35                  40                  45

Met Gly Tyr Ile Thr Tyr Asp Gly Ser Asn Asn Tyr Asn Pro Ser Leu
    50                  55                  60

Lys Asn Arg Ile Thr Ile Ser Arg Asp Thr Ser Lys Asn Gln Phe Phe
65                  70                  75                  80

Leu Lys Leu Ser Ser Val Thr Ala Ala Asp Thr Ala Val Tyr Tyr Cys
                85                  90                  95

Ala Asp Phe Asp Tyr Trp Gly Gln Gly Thr Thr Val Thr Val Ser Ser
            100                 105                 110

Ala Ser Thr Lys Gly Pro Ser Val Phe Pro Leu Ala Pro Ser Ser Lys
        115                 120                 125

Ser Thr Ser Gly Gly Thr Ala Ala Leu Gly Cys Leu Val Lys Asp Tyr
    130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175

Leu Ser Ser Val Val Thr Val Pro Ser Ser Ser Leu Gly Thr Gln Thr
            180                 185                 190

Tyr Ile Cys Asn Val Asn His Lys Pro Ser Asn Thr Lys Val Asp Lys
        195                 200                 205

Lys Val Glu Pro Lys Ser Cys Asp Lys Thr His Thr Cys Pro Pro Cys
    210                 215                 220

Pro Ala Pro Glu Leu Leu Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser His Glu Asp Pro Glu Val Lys Phe Asn Trp
            260                 265                 270

Tyr Val Asp Gly Val Glu Val His Asn Ala Lys Thr Lys Pro Arg Glu
        275                 280                 285
```

-continued

```
Glu Gln Tyr Asn Ser Thr Tyr Arg Val Val Ser Val Leu Thr Val Leu
    290                 295                 300

His Gln Asp Trp Leu Asn Gly Lys Glu Tyr Lys Cys Lys Val Ser Asn
305                 310                 315                 320

Lys Ala Leu Pro Ala Pro Ile Glu Lys Thr Ile Ser Lys Ala Lys Gly
                325                 330                 335

Gln Pro Arg Glu Pro Gln Val Tyr Thr Leu Pro Pro Ser Arg Asp Glu
            340                 345                 350

Leu Thr Lys Asn Gln Val Ser Leu Thr Cys Leu Val Lys Gly Phe Tyr
        355                 360                 365

Pro Ser Asp Ile Ala Val Glu Trp Glu Ser Asn Gly Gln Pro Glu Asn
    370                 375                 380

Asn Tyr Lys Thr Thr Pro Pro Val Leu Asp Ser Asp Gly Ser Phe Phe
385                 390                 395                 400

Leu Tyr Ser Lys Leu Thr Val Asp Lys Ser Arg Trp Gln Gln Gly Asn
                405                 410                 415

Val Phe Ser Cys Ser Val Met His Glu Ala Leu His Asn His Tyr Thr
            420                 425                 430

Gln Lys Ser Leu Ser Leu Ser Pro Gly Lys
        435                 440


<210> SEQ ID NO 36
<211> LENGTH: 442
<212> TYPE: PRT
<213> ORGANISM: Artificial Sequence
<220> FEATURE:
<223> OTHER INFORMATION: Synthetic sequence humanized ARD107 H4 heavy
      chain

<400> SEQUENCE: 36

Glu Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Thr Ser Gly
            20                  25                  30

Tyr Tyr Trp Asn Trp Ile Arg Gln Phe Pro Gly Asn Lys Leu Glu Trp
        35                  40                  45

Met Gly Tyr Ile Thr Tyr Asp Gly Ser Asn Asn Tyr Asn Pro Ser Leu
    50                  55                  60

Lys Asn Arg Ile Thr Ile Ser Arg Asp Thr Ser Lys Asn Gln Phe Phe
65                  70                  75                  80

Leu Lys Leu Ser Ser Val Thr Ala Glu Asp Thr Ala Val Tyr Tyr Cys
                85                  90                  95

Ala Asp Phe Asp Tyr Trp Gly Gln Gly Thr Thr Leu Thr Val Ser Ser
            100                 105                 110

Ala Ser Thr Lys Gly Pro Ser Val Phe Pro Leu Ala Pro Ser Ser Lys
        115                 120                 125

Ser Thr Ser Gly Gly Thr Ala Ala Leu Gly Cys Leu Val Lys Asp Tyr
    130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175

Leu Ser Ser Val Val Thr Val Pro Ser Ser Ser Leu Gly Thr Gln Thr
            180                 185                 190

Tyr Ile Cys Asn Val Asn His Lys Pro Ser Asn Thr Lys Val Asp Lys
        195                 200                 205
```

```
Lys Val Glu Pro Lys Ser Cys Asp Lys Thr His Thr Cys Pro Pro Cys
    210                 215                 220

Pro Ala Pro Glu Leu Leu Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser His Glu Asp Pro Glu Val Lys Phe Asn Trp
            260                 265                 270

Tyr Val Asp Gly Val Glu Val His Asn Ala Lys Thr Lys Pro Arg Glu
        275                 280                 285

Glu Gln Tyr Asn Ser Thr Tyr Arg Val Val Ser Val Leu Thr Val Leu
    290                 295                 300

His Gln Asp Trp Leu Asn Gly Lys Glu Tyr Lys Cys Lys Val Ser Asn
305                 310                 315                 320

Lys Ala Leu Pro Ala Pro Ile Glu Lys Thr Ile Ser Lys Ala Lys Gly
                325                 330                 335

Gln Pro Arg Glu Pro Gln Val Tyr Thr Leu Pro Pro Ser Arg Asp Glu
            340                 345                 350

Leu Thr Lys Asn Gln Val Ser Leu Thr Cys Leu Val Lys Gly Phe Tyr
        355                 360                 365

Pro Ser Asp Ile Ala Val Glu Trp Glu Ser Asn Gly Gln Pro Glu Asn
    370                 375                 380

Asn Tyr Lys Thr Thr Pro Pro Val Leu Asp Ser Asp Gly Ser Phe Phe
385                 390                 395                 400

Leu Tyr Ser Lys Leu Thr Val Asp Lys Ser Arg Trp Gln Gln Gly Asn
                405                 410                 415

Val Phe Ser Cys Ser Val Met His Glu Ala Leu His Asn His Tyr Thr
            420                 425                 430

Gln Lys Ser Leu Ser Leu Ser Pro Gly Lys
        435                 440


<210> SEQ ID NO 37
<211> LENGTH: 214
<212> TYPE: PRT
<213> ORGANISM: Artificial Sequence
<220> FEATURE:
<223> OTHER INFORMATION: Synthetic sequence humanized ARD107 L1 light
      chain

<400> SEQUENCE: 37

Asp Ile Gln Leu Thr Gln Ser Pro Ser Ser Leu Ser Ala Ser Val Gly
1               5                   10                  15

Asp Arg Val Thr Ile Thr Cys Ser Ala Ser Gln Gly Ile Arg Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Lys Leu Pro Trp
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
```

```
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 38
<211> LENGTH: 214
<212> TYPE: PRT
<213> ORGANISM: Artificial Sequence
<220> FEATURE:
<223> OTHER INFORMATION: Synthetic sequence humanized ARD107 L2 light
      chain

<400> SEQUENCE: 38

Asp Ile Gln Leu Thr Gln Ser Pro Ser Ser Leu Ser Ala Ser Val Gly
1               5                   10                  15

Asp Arg Val Thr Ile Thr Cys Ser Ala Ser Gln Gly Ile Arg Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Ser Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Tyr Ser Lys Leu Pro Trp
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 39
<211> LENGTH: 214
<212> TYPE: PRT
<213> ORGANISM: Artificial Sequence
<220> FEATURE:
```

<223> OTHER INFORMATION: Synthetic sequence humanized ARD107 L3 light chain

<400> SEQUENCE: 39

Asp Ile Gln Leu Thr Gln Ser Pro Ser Ser Leu Ser Ala Ser Val Gly
1               5                   10                  15

Asp Arg Val Thr Ile Thr Cys Ser Ala Ser Gln Gly Ile Arg Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Thr Tyr Tyr Cys Gln Gln Tyr Ser Lys Leu Pro Trp
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 40
<211> LENGTH: 214
<212> TYPE: PRT
<213> ORGANISM: Artificial Sequence
<220> FEATURE:
<223> OTHER INFORMATION: Synthetic sequence humanized ARD107 L4 light chain

<400> SEQUENCE: 40

Asp Ile Val Leu Thr Gln Ser Pro Ser Ser Leu Ser Ala Ser Val Gly
1               5                   10                  15

Asp Arg Val Thr Ile Thr Cys Ser Ala Ser Gln Gly Ile Arg Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Ser Leu His Ser Gly Val Pro Ser Arg Phe Ser Gly
    50                  55                  60

Ser Gly Ser Gly Thr Asp Tyr Thr Leu Thr Ile Ser Ser Leu Glu Pro
65                  70                  75                  80

Glu Asp Ile Ala Thr Tyr Tyr Cys Gln Gln Tyr Ser Lys Leu Pro Trp
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 41
<211> LENGTH: 336
<212> TYPE: DNA
<213> ORGANISM: Artificial Sequence
<220> FEATURE:
<223> OTHER INFORMATION: Synthetic sequence humanized ARD107 VH1

<400> SEQUENCE: 41
gaggtccagc tgcaggagtc aggacctggc ctcgtgaaac cttctcagac cctgtctctc 60
acctgcaccg tctctggcta ctccatcacc agtggttatt actggaactg gatccggcag 120
tttccaggaa acaagctgga atggatgggc tacataacct acgacggtag caataactac 180
aacccatctc tcaaaaatcg agtgaccatc agccgtgaca catctaagaa ccagtttagc 240
ctgaagttga gctctgtgac tgcggcggac acagctgtgt attactgtgc ggactttgac 300
tactggggcc aaggcaccac tgtgacagtc tcctca 336

<210> SEQ ID NO 42
<211> LENGTH: 336
<212> TYPE: DNA
<213> ORGANISM: Artificial Sequence
<220> FEATURE:
<223> OTHER INFORMATION: Synthetic sequence humanized ARD107 VH2

<400> SEQUENCE: 42
gaggtccagc tgcaggagtc aggacctggc ctcgtgaaac cttctcagac cctgtctctc 60
acctgcaccg tctctggcta ctccatcacc agtggttatt actggaactg gatccggcag 120
tttccaggaa acaagctgga atggatgggc tacataacct acgacggtag caataactac 180
aacccatctc tcaaaaatcg agtgaccatc agccgtgaca catctaagaa ccagtttagc 240
ctgaagttga gctctgtgac tgcggaggac acagctgtgt attactgtgc ggactttgac 300
tactggggcc aaggcaccac tctcacagtc tcctca 336

<210> SEQ ID NO 43
<211> LENGTH: 336
<212> TYPE: DNA
<213> ORGANISM: Artificial Sequence
<220> FEATURE:
<223> OTHER INFORMATION: Synthetic sequence humanized ARD107 VH3

<400> SEQUENCE: 43
gaggtccagc tgcaggagtc aggacctggc ctcgtgaaac cttctcagac cctgtctctc 60
acctgcaccg tctctggcta ctccatcacc agtggttatt actggaactg gatccggcag 120

```
tttccaggaa acaagctgga atggatgggc tacataacct acgacggtag caataactac    180

aacccatctc tcaaaaatcg aatcaccatc agccgtgaca catctaagaa ccagtttttc    240

ctgaagttga gctctgtgac tgcggcggac acagctgtgt attactgtgc ggactttgac    300

tactggggcc aaggcaccac tgtgacagtc tcctca                              336


<210> SEQ ID NO 44
<211> LENGTH: 336
<212> TYPE: DNA
<213> ORGANISM: Artificial Sequence
<220> FEATURE:
<223> OTHER INFORMATION: Synthetic sequence humanized ARD107 VH4

<400> SEQUENCE: 44

gaggtccagc tgcaggagtc aggacctggc ctcgtgaaac cttctcagac cctgtctctc     60

acctgcaccg tctctggcta ctccatcacc agtggttatt actggaactg gatccggcag    120

tttccaggaa acaagctgga atggatgggc tacataacct acgacggtag caataactac    180

aacccatctc tcaaaaatcg aatcaccatc agccgtgaca catctaagaa ccagtttttc    240

ctgaagttga gctctgtgac tgcggaggac acagctgtgt attactgtgc ggactttgac    300

tactggggcc aaggcaccac tctcacagtc tcctca                              336


<210> SEQ ID NO 45
<211> LENGTH: 321
<212> TYPE: DNA
<213> ORGANISM: Artificial Sequence
<220> FEATURE:
<223> OTHER INFORMATION: Synthetic sequence humanized ARD107 VL1

<400> SEQUENCE: 45

gatattcagc tcacacagtc tccatcctcc ctgtctgcct ctgtgggaga cagagtcacc     60

atcacctgca gtgcaagtca gggcattaga aattatttaa actggtatca gcagaaacca    120

gatggaactg ttaaactcct gatctattac acatcaagtt tacactcagg agtcccatca    180

aggttcagtg gcagtgggtc tgggacagat tttaccctca ccatcagcag cctgcagcct    240

gaagattttg ccacttacta ttgtcagcag tatagtaagc ttccttggac gttcggtgga    300

ggcaccaagc tggaaatcaa a                                              321


<210> SEQ ID NO 46
<211> LENGTH: 321
<212> TYPE: DNA
<213> ORGANISM: Artificial Sequence
<220> FEATURE:
<223> OTHER INFORMATION: Synthetic sequence humanized ARD107 VL2

<400> SEQUENCE: 46

gatattcagc tcacacagtc tccatcctcc ctgtctgcct ctgtgggaga cagagtcacc     60

atcacctgca gtgcaagtca gggcattaga aattatttaa actggtatca gcagaaacca    120

gatggaactg ttaaactcct gatctattac acatcaagtt tacactcagg agtcccatca    180

aggttcagtg gcagtgggtc tgggacagat tataccctca ccatcagcag cctgcagcct    240

gaagattttg ccacttacta ttgtcagcag tatagtaagc ttccttggac gttcggtgga    300

ggcaccaagc tggaaatcaa a                                              321


<210> SEQ ID NO 47
<211> LENGTH: 321
<212> TYPE: DNA
<213> ORGANISM: Artificial Sequence
```

-continued

```
<220> FEATURE:
<223> OTHER INFORMATION: Synthetic sequence humanized ARD107 VL3

<400> SEQUENCE: 47

gatattcagc tcacacagtc tccatcctcc ctgtctgcct ctgtgggaga cagagtcacc      60

atcacctgca gtgcaagtca gggcattaga aattatttaa actggtatca gcagaaacca     120

gatggaactg ttaaactcct gatctattac acatcaagtt tacactcagg agtcccatca     180

aggttcagtg gcagtgggtc tgggacagat tttaccctca ccatcagcag cctggaacct     240

gaagattttg ccacttacta ttgtcagcag tatagtaagc ttccttggac gttcggtgga     300

ggcaccaagc tggaaatcaa a                                               321


<210> SEQ ID NO 48
<211> LENGTH: 321
<212> TYPE: DNA
<213> ORGANISM: Artificial Sequence
<220> FEATURE:
<223> OTHER INFORMATION: Synthetic sequence humanized ARD107 VL4

<400> SEQUENCE: 48

gatattgtgc tcacacagtc tccatcctcc ctgtctgcct ctgtgggaga cagagtcacc      60

atcacctgca gtgcaagtca gggcattaga aattatttaa actggtatca gcagaaacca     120

gatggaactg ttaaactcct gatctattac acatcaagtt tacactcagg agtcccatca     180

aggttcagtg gcagtgggtc tgggacagat tataccctca ccatcagcag cctggaacct     240

gaagatattg ccacttacta ttgtcagcag tatagtaagc ttccttggac gttcggtgga     300

ggcaccaagc tggaaatcaa a                                               321
```

ANTI-CSPG4 BINDING AGENTS, ENCODING NUCLEIC ACIDS THEREOF, CONJUGATES THEREOF AND METHODS OF USE THEREOF TO TREAT A CSPG4+ CANCER

REFERENCE TO AN ELECTRONIC SEQUENCE LISTING

The Sequence Listing associated with this application is provided in text format in lieu of a paper copy, and is hereby incorporated by reference into the specification. The name of the text file containing the Sequence Listing is 120301_401USPC_SEQUENCE_LISTING.txt. The text file is 98,539 bytes, was created on Mar. 30, 2023, and is being submitted electronically via EFS-Web.

BACKGROUND

Effective and tumor-targeted treatment for various types of cancer remain an important need for improvement of survival for patients. Worldwide in 2018, there were 2.1 million cases of invasive breast cancer with 620,000 deaths. In the same year, head and neck cancers and malignant melanoma accounted for 286,000 deaths and 61,000 deaths, accordingly. Currently, there are few therapeutic options for glioblastoma and pancreatic cancers. Chondroitin sulfate proteoglycan 4 or CSPG4, an oncofetal antigen that is also expressed on human malignant cells, is known to be highly expressed in these tumors, as well as in renal cell carcinoma, mesothelioma, bladder cancer, chondrosarcoma, osteosarcoma, and some forms of leukemia. With the limited expression of CSPG4 in normal adult tissues, targeting of CSPG4 using an antibody armed with a cytotoxic agent (antibody-drug conjugate) provides a way of selectively attacking the cancer cells and sparing normal tissues.

BRIEF SUMMARY

The present disclosure provides in part on ARD107 anti-CSPG4 binding antibodies, humanized variants thereof, antigen-binding portions thereof and related binding agents that specifically bind to CSPG4, as well as conjugates thereof, that exhibit improved therapeutic properties. CSPG4 is an important and advantageous therapeutic target for the treatment of certain cancers. The CSPG4-binding antibodies, antigen binding portions thereof and binding agents and conjugates thereof provide compositions and methods based on the use of such antibodies, antigen binding portions and related binding agents, and conjugates thereof, in the treatment of CSPG4+ cancers. Accordingly, the present disclosure provides methods, compositions, kits, and articles of manufacture related to ARD107 anti-CSPG4 antibodies, humanized variants thereof, antigen-binding portions, binding agents and conjugates.

In some embodiments, a conjugate is provided comprising: a binding agent comprising: (i) a heavy chain variable (VH) region having the amino acid sequence set forth in SEQ ID NO:1, and (ii) a light chain variable (VL) region having the amino acid sequence set forth in SEQ ID NO:2; (iii) a heavy chain variable (VH) region having the amino acid sequence set forth in SEQ ID NO:25, and (iv) a light chain variable (VL) region having the amino acid sequence set forth in SEQ ID NO:30; (v) a heavy chain variable (VH) region having the amino acid sequence set forth in SEQ ID NO:27, and (vi) a light chain variable (VL) region having the amino acid sequence set forth in SEQ ID NO:30; or (vii) a heavy chain variable (VH) region having the amino acid sequence set forth in SEQ ID NO:27, and (viii) a light chain variable (VL) region having the amino acid sequence set forth in SEQ ID NO:31, wherein the heavy and light chain framework regions are optionally modified with from 1 to 8 amino acid substitutions, deletions or insertions in the framework regions, wherein the binding agent specifically binds to human CSPG4; at least one linker attached to the binding agent; and at least one cytotoxic agent attached to each linker.

In some embodiments, the binding agent comprises: (i) a heavy chain variable region having the amino acid sequence set forth in SEQ ID NO:1, and (ii) a light chain variable region having the amino acid sequence set forth in SEQ ID NO:2.

In some embodiments, the binding agent comprises: (i) a heavy chain variable (VH) region having the amino acid sequence set forth in SEQ ID NO:25, and (ii) a light chain variable (VL) region having the amino acid sequence set forth in SEQ ID NO:30.

In some embodiments, the binding agent comprises: (i) a heavy chain variable (VH) region having the amino acid sequence set forth in SEQ ID NO:27, and (ii) a light chain variable (VL) region having the amino acid sequence set forth in SEQ ID NO:30.

In some embodiments, the binding agent comprises: (i) a heavy chain variable (VH) region having the amino acid sequence set forth in SEQ ID NO:27, and (ii) a light chain variable (VL) region having the amino acid sequence set forth in SEQ ID NO:31.

In some embodiments, a conjugate is provided comprising: a binding agent comprising a heavy chain variable (VH) region and a light chain variable (VL) region, wherein the VH region comprises a complementarity determining region HCDR1 sequence having the amino acid sequence set forth in SEQ ID NO:11, a HCDR2 having the amino acid sequence set forth in SEQ ID NO:12, and a HCDR3 having the amino acid sequence set forth in SEQ ID NO:13, each disposed within a heavy chain framework region; and wherein the VL region comprises a LCDR1 sequence having the amino acid sequence set forth in SEQ ID NO:14, a LCDR2 having the amino acid sequence set forth in SEQ ID NO:15, and a LCDR3 having the amino acid sequence set forth in SEQ ID NO:16, each disposed within a light chain framework region; at least one linker attached to the binding agent; and at least one cytotoxic agent attached to each linker.

In some embodiments, the framework regions are murine framework regions.

In some embodiments, the framework regions are human framework regions.

In some embodiments, the binding agent is an antibody or an antigen-binding portion thereof.

In some embodiments, the binding agent is a monoclonal antibody, a Fab, a Fab', an F(ab'), an Fv, a disulfide linked Fc, a scFv, a single domain antibody, a diabody, a bi-specific antibody, or a multi-specific antibody.

In some embodiments, the heavy chain variable region further comprises a heavy chain constant region.

In some embodiments, heavy chain constant region is of the human IgG isotype.

In some embodiments, the heavy chain constant region is an IgG1 constant region.

In some embodiments, the IgG1 heavy chain constant region has the amino acid sequence set forth in positions 113-442 of SEQ ID NO:3.

In some embodiments, the heavy chain constant region is an IgG4 constant region.

In some embodiments, the heavy chain variable and constant regions have the amino acid sequence set forth in SEQ ID NO: 3.

In some embodiments, the heavy chain variable and constant regions have the amino acid sequence set forth in SEQ ID NO: 33.

In some embodiments, the heavy chain variable and constant regions have the amino acid sequence set forth in SEQ ID NO: 35.

In some embodiments, the light chain variable region further comprises a light chain constant region.

In some embodiments, the light chain constant region is of the kappa isotype.

In some embodiments, the kappa light chain constant region has the amino acid sequence set forth in positions 108-214 of SEQ ID NO:4.

In some embodiments, the light chain variable and constant regions have the amino acid sequence set forth in SEQ ID NO:4.

In some embodiments, the light chain variable and constant regions have the amino acid sequence set forth in SEQ ID NO:38.

In some embodiments, the light chain variable and constant regions have the amino acid sequence set forth in SEQ ID NO:39.

In some embodiments, the binding agent comprises: (a) the heavy chain variable and constant regions having the amino acid sequence set forth SEQ ID NO:3, and the light chain variable and constant regions having the amino acid sequence set forth in SEQ ID NO:4; (b) the heavy chain variable and constant regions having the amino acid sequence set forth SEQ ID NO:33, and the light chain variable and constant regions having the amino acid sequence set forth in SEQ ID NO:38; (c) the heavy chain variable and constant regions having the amino acid sequence set forth SEQ ID NO:35, and the light chain variable and constant regions having the amino acid sequence set forth in SEQ ID NO:38; or (d) the heavy chain variable and constant regions having the amino acid sequence set forth SEQ ID NO:35, and the light chain variable and constant regions having the amino acid sequence set forth in SEQ ID NO:39.

In some embodiments, the linker is attached to the binding agent via an interchain disulfide residue, an engineered cysteine, a glycan or modified glycan, an N-terminal residue of the binding agent or a polyhistidine residue attached to the binding agent.

In some embodiments, the average drug loading of the conjugate is from about 1 to about 8, about 2, about 4, about 6, about 8, about 10, about 12, about 14, about 16, about 3 to about 5, about 6 to about 8 or about 8 to about 16.

In some embodiments, the binding agent is mono-specific.

In some embodiments, the binding agent is bivalent.

In some embodiments, the binding agent comprises a second binding domain and the binding agent is bispecific.

In some embodiments, the cytotoxic agent is selected from the group consisting of an auristatin, a camptothecin and a calicheamicin.

In some embodiments, the cytotoxic agent is an auristatin.

In some embodiments, the cytotoxic agent is monomethyl auristatin E (MMAE).

In some embodiments, the cytotoxic agent is a camptothecin.

In some embodiments, the cytotoxic agent is exatecan.

In some embodiments, the cytotoxic agent is a calicheamicin.

In some embodiments, the cytotoxic agent is SN-38.

In some embodiments, the linker is selected from the group consisting of mc-VC-PAB, CL2, CL2A, maleimide-acetyl-Gly-Val-Cit-PAB, and (Succinimid-3-yl-N)—(CH2)$_n$$^2$-C(═O)-Gly-Gly-Phe-Gly-NH—CH2=OCH2-(C═O)—.

In some embodiments, the linker is mc-VC-PAB.

In some embodiments, the linker is attached to at least one molecule of MMAE.

In some embodiments, the linker is CL2A.

In some embodiments, the linker is attached to at least one molecule of SN-38 (also known as 7-Ethyl-10-hydroxycamptothecin).

In some embodiments, the linker is CL2.

In some embodiments, the linker is attached to at least one molecule of SN-38.

In some embodiments, the linker is (Succinimid-3-yl-N)—(CH2)$_n$$^2$-C(═O)-Gly-Gly-Phe-Gly-NH—CH2=OCH2-(C═O)—.

In some embodiments, the linker is attached to at least one molecule of exatecan.

In some embodiments, a binding agent is provided comprising: (a) a heavy chain variable (VH) region having the amino acid sequence set forth in SEQ ID NO:25, and a light chain variable (VL) region having the amino acid sequence set forth in SEQ ID NO:30; (b) a heavy chain variable (VH) region having the amino acid sequence set forth in SEQ ID NO:27, and a light chain variable (VL) region having the amino acid sequence set forth in SEQ ID NO:30; or (c) a heavy chain variable (VH) region having the amino acid sequence set forth in SEQ ID NO:27, and a light chain variable (VL) region having the amino acid sequence set forth in SEQ ID NO:31; wherein the heavy and light chain framework regions are optionally modified with from 1 to 8 amino acid substitutions, deletions or insertions in the framework regions, and wherein the binding agent specifically binds to human CSPG4.

In some embodiments, the binding agent comprises (a) a heavy chain variable region having the amino acid sequence set forth in SEQ ID NO:25, and a light chain variable region having the amino acid sequence set forth in SEQ ID NO:30; (b) a heavy chain variable region having the amino acid sequence set forth in SEQ ID NO:27, and a light chain variable region having the amino acid sequence set forth in SEQ ID NO:30; or (c) a heavy chain variable region having the amino acid sequence set forth in SEQ ID NO:27, and a light chain variable region having the amino acid sequence set forth in SEQ ID NO:31.

In some embodiments, the framework regions are murine framework regions.

In some embodiments, the framework regions are human framework regions.

In some embodiments, the binding agent is an antibody or an antigen-binding portion thereof.

In some embodiments, the binding agent is a monoclonal antibody, a Fab, a Fab', an F(ab'), an Fv, a disulfide linked Fc, a scFv, a single domain antibody, a diabody, a bi-specific antibody, or a multi-specific antibody.

In some embodiments, the heavy chain variable region further comprises a heavy chain constant region.

In some embodiments, heavy chain constant region is of the human IgG isotype.

In some embodiments, the heavy chain constant region is an IgG1 constant region.

In some embodiments, the IgG1 heavy chain constant region has the amino acid sequence set forth in positions 113-442 of SEQ ID NO:3.

In some embodiments, the heavy chain constant region is an IgG4 constant region.

In some embodiments, the heavy chain variable and constant regions have the amino acid sequence set forth in SEQ ID NO: 33 or 35.

In some embodiments, the light chain variable region further comprises a light chain constant region.

In some embodiments, the light chain constant region is of the kappa isotype.

In some embodiments, the kappa light chain constant region has the amino acid sequence set forth in positions 108-214 of SEQ ID NO:4.

In some embodiments, the light chain variable and constant regions have the amino acid sequence set forth in SEQ ID NO:38 or 39.

In some embodiments, (a) the heavy chain variable and constant regions have the amino acid sequence set forth SEQ ID NO:33, and the light chain variable and constant regions have the amino acid sequence set forth in SEQ ID NO:38; (b) the heavy chain variable and constant regions have the amino acid sequence set forth SEQ ID NO:35, and the light chain variable and constant regions have the amino acid sequence set forth in SEQ ID NO:38; or (c) the heavy chain variable and constant regions have the amino acid sequence set forth SEQ ID NO:35, and the light chain variable and constant regions have the amino acid sequence set forth in SEQ ID NO:39.

In some embodiments, provide is a pharmaceutical composition comprising the conjugate or binding agent of any of the embodiments described herein and a pharmaceutically acceptable carrier.

In some embodiments, provided is a nucleic acid encoding the binding agent of any of embodiments described herein.

In some embodiments, provided is a vector comprising the nucleic acid of the preceding embodiment.

In some embodiments, provided is a cell line comprising the nucleic acid of any of the embodiments described herein.

In some embodiments, provided is a method of treating a CSPG4+ cancer, comprising administering to a subject in need thereof a therapeutically effective amount of the conjugate of any of embodiments of conjugates or binding agent of any of embodiments of binding agents described herein or the pharmaceutical composition of any of these conjugates or binding agents.

In some embodiments of the method, the CSPG4+ cancer is a carcinoma or a malignancy.

In some embodiments of the method the CSPG4+ cancer is selected from melanoma, head and neck cancer, breast cancer, mesothelioma, renal clear cell cancer, chondrosarcoma, urothelial (bladder) cancer, osteosarcoma, pancreatic cancer, and leukemia (B-ALL).

In some embodiments of the method, it further comprises administering an immunotherapy to the subject.

In some embodiments of the method, the immunotherapy comprises an immune checkpoint inhibitor.

In some embodiments of the method, the immune checkpoint inhibitor is selected from an antibody that specifically binds to human PD-1, human PD-L1, or human CTLA4.

In some embodiments of the method, the immune checkpoint inhibitor is pembrolizumab, nivolumab, cemiplimab or ipilimumab.

In some embodiments, the method further comprises administering chemotherapy to the subject.

In some embodiments of the method, the conjugate or binding agent is administered intravenously.

In some embodiments of the method, the conjugate or binding agent is administered in a dose of about 0.1 mg/kg to about 10 mg/kg or from about 0.1 mg/kg to about 12 mg/kg.

In some embodiments, provided is a method of improving treatment outcome in a subject receiving immunotherapy and/or chemotherapy for a CSPG4+ cancer, comprising: administering an effective amount of an immunotherapy or chemotherapy to the subject having cancer; and administering a therapeutically effective amount of the conjugate of any of embodiments of conjugates or the binding agent of any of embodiments of binding agents described herein or the pharmaceutical composition of any of the conjugates or binding agents described herein; wherein the treatment outcome of the subject is improved, as compared to administration of the immunotherapy or chemotherapy alone.

In some embodiments, the improved treatment outcome is an objective response selected from stable disease, a partial response or a complete response.

In some embodiments, the improved treatment outcome is reduced tumor burden.

In some embodiments, the improved treatment outcome is progression-free survival or disease-free survival.

In some embodiments, the immunotherapy is an immune checkpoint inhibitor.

In some embodiments, the immune checkpoint inhibitor comprises an antibody that specifically binds to human PD-1, human PD-L1, or CTLA4.

In some embodiments, the immune checkpoint inhibitor is pembrolizumab, nivolumab, cemiplimab or ipilimumab.

In some embodiments, the conjugate or binding agent is administered intravenously.

In some embodiments, the conjugate or binding agent is administered in a dose of about 0.1 mg/kg to about 10 mg/kg.

In some embodiments, provided is the use of a conjugate or binding agent described herein or a pharmaceutical composition of a conjugate or binding agent described herein for the treatment of CSPG4+ cancer in a subject.

In some embodiments, provided is the use of a conjugate or binding agent described herein or a pharmaceutical composition of any of the conjugates described herein for the treatment of CSPG4+ cancer in a subject receiving immunotherapy or chemotherapy.

These and other aspects of the present invention may be more fully understood by reference to the following detailed description, non-limiting examples of specific embodiments and the appended drawings.

BRIEF DESCRIPTION OF THE DRAWINGS

FIG. 6. Comparison of binding of different preparations of ARD107-vcMMAE to recombinant human CSPG4 protein.

DETAILED DESCRIPTION

Figure 1A:
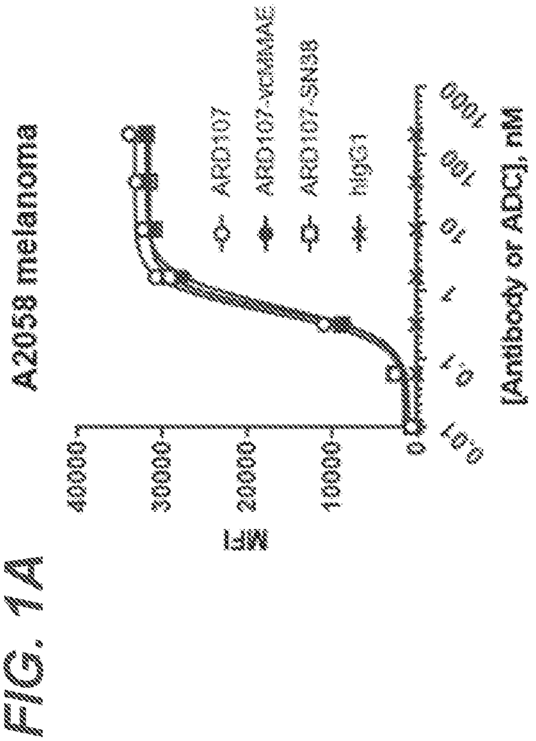
FIGS. 1A-1D. FACs binding of ARD107 antibody and corresponding ARD107 ADCs to CSPG4-positive cell lines.
Figure 1B:
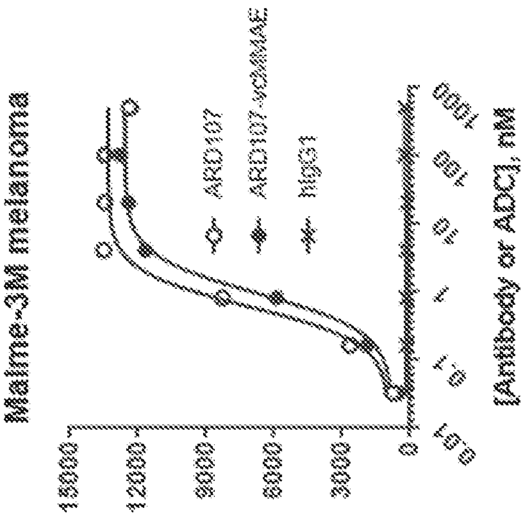
Figure 1C:
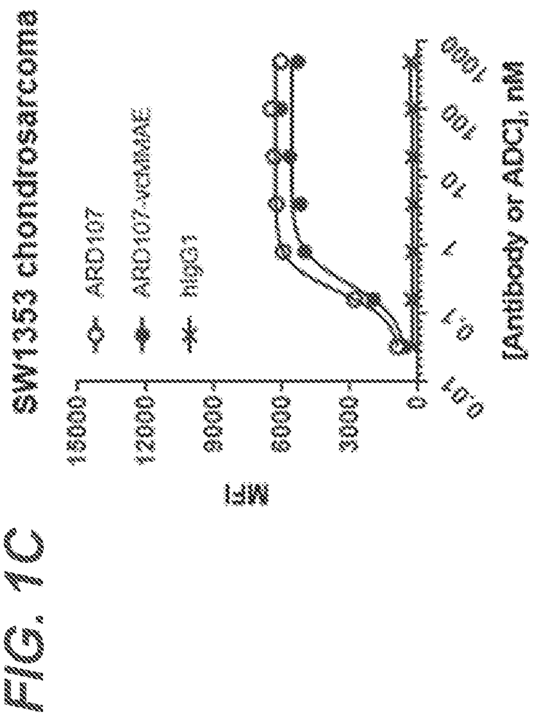
Figure 1D:
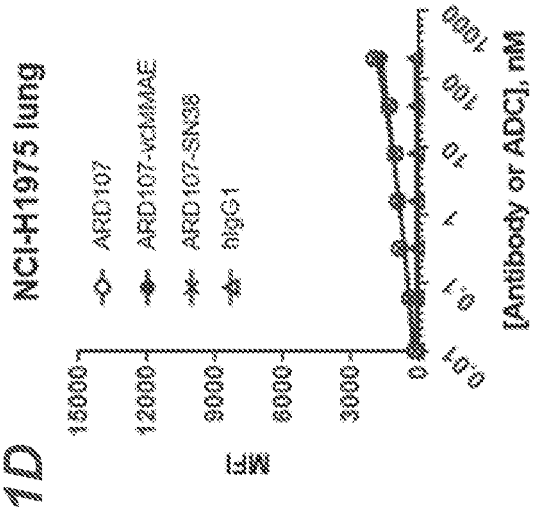

The disclosure provides anti-CSPG4 antibodies, cytotoxic agent conjugates comprising anti-CSPG4 antibodies, and pharmaceutical compositions that comprise such antibodies and conjugates. The antibodies, conjugates and pharmaceutical compositions of the disclosure are useful in treating a CSPG4+ cancer, alone or in combination with other cancer therapeutic agents.

For convenience, certain terms in the specification, examples and claims are defined here. Unless stated otherwise, or implicit from context, the following terms and phrases have the meanings provided below. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs.

As used herein and unless otherwise indicated, the terms "a" and "an" are taken to mean "one", "at least one" or "one or more". Unless otherwise required by context, singular terms used herein shall include pluralities and plural terms shall include the singular.

The use of the alternative (e.g., "or") should be understood to mean either one, both, or any combination thereof of the alternatives. As used throughout the disclosure, the terms "include" and "comprise" are used synonymously.

"Optional" or "optionally" means that the subsequently described element, component, event, or circumstance may or may not occur, and that the description includes instances in which the element, component, event, or circumstance occurs and instances in which they do not.

The phrase "at least one of" when followed by a list of items or elements refers to an open ended set of one or more of the elements in the list, which may, but does not necessarily, include more than one of the elements.

The term "about" as used throughout the disclosure in the context of a number refers to a range centered on that number and spanning 15% less than that number and 15% more than that number. The term "about" used in the context of a range refers to an extended range spanning 15% less than that the lowest number listed in the range and 15% more than the greatest number listed in the range.

Throughout the disclosure, any concentration range, percentage range, ratio range, or integer range is to be understood to include any value (including integers or fractions) or subrange within the recited range unless otherwise indicated.

Unless the context clearly requires otherwise, throughout the description and the claims, the words "comprise", "comprising", and the like are to be construed in an inclusive sense as opposed to an exclusive or exhaustive sense; that is to say, in the sense of "including, but not limited to".

The terms "decrease," "reduce," "reduced", "reduction", "decrease," and "inhibit" are all used herein generally to mean a decrease by a statistically significant amount relative to a reference.

The terms "increased", "increase" or "enhance" or "activate" are all used herein to generally mean an increase by a statically significant amount relative to a reference.

The terms "isolated" or "partially purified" as used herein refer in the case of a nucleic acid, polypeptide or protein, to a nucleic acid, polypeptide or protein separated from at least one other component (e.g., nucleic acid or polypeptide or protein) that is present with the nucleic acid, polypeptide or protein as found in its natural source and/or that would be present with the nucleic acid, polypeptide or protein when expressed by a cell, or secreted in the case of secreted polypeptides and proteins. A chemically synthesized nucleic acid, polypeptide or protein, or one synthesized using in vitro transcription/translation, is considered "isolated." The terms "purified" or "substantially purified" refer to an isolated nucleic acid, polypeptide or protein that is at least 95% by weight the subject nucleic acid, polypeptide or protein, including, for example, at least 96%, at least 97%, at least 98%, at least 99% or more.

As used herein, the terms "protein" and "polypeptide" are used interchangeably herein to designate a series of amino acid residues each connected to each other by peptide bonds between the alpha-amino and carboxyl groups of adjacent residues. The terms "protein" and "polypeptide" also refer to a polymer of protein amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to an encoded gene product and fragments thereof. Thus, exemplary polypeptides or proteins include gene products, naturally occurring proteins, homologs, orthologs, paralogs, fragments and other equivalents, variants, fragments, and analogs of the foregoing.

CSPG4, or chondroitin sulfate proteoglycan 4, is an oncofetal antigen that is expressed on human malignant cells. CSPG4 is also referred to as chondroitin sulfate proteoglycan 4 (melanoma associated); HMW MAA; MCSP; MCSPG; MEL CSPG; melanoma associated chondroitin sulfate proteoglycan; MSK16; NG2; chondroitin sulfate proteoglycan NG2; and melanoma chondroitin sulfate proteoglycan. CSPG4 polypeptides include, but are not limited to, those having the amino acid sequence set forth in NCBI Ref Seq. NP_001888.2 (SEQ ID NO:9) and UniProtKB Q6UVK1 (SEQ ID NO:10); these sequences are incorporated by reference herein.

As used herein, an "epitope" refers to the amino acids typically bound by an immunoglobulin VH/VL pair, such as the antibodies and binding agents described herein. An epitope can be formed on a polypeptide from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, and more usually, at least 5, about 9, or about 8-10 amino acids in a unique spatial conformation. An epitope defines the minimum binding site for an antibody or other binding agent, and thus represent the target of specificity of an antibody, antigen binding portion thereof or other immunoglobulin-based binding agent. In the case of a single domain antibody, an epitope represents the unit of structure bound by a variable domain in isolation.

As used herein, "specifically binds" refers to the ability of a binding agent (e.g., an antibody or antigen binding portion thereof) described herein to bind to a target, such as CSPG4, with a KD $10^{-5}$ M (10000 nM) or less, e.g., $10^{-6}$ M, $10^{-7}$ M, $10^{-8}$M, $10^{-9}$ M, $10^{-10}$ M, $10^{-11}$ M, $10^{-12}$ M, or less. Specific binding can be influenced by, for example, the affinity and avidity of the antibody or other binding agent and the concentration of target polypeptide. The person of ordinary skill in the art can determine appropriate conditions under which the antibodies and other binding agents described herein selectively bind to CSPG4 using any suitable methods, such as titration of a binding agent in a suitable cell binding assay. A binding agent specifically bound to CSPG4 is not displaced by a non-similar competitor. In certain embodiments, an anti-CSPG4 antibody or antigen-binding portion thereof is said to specifically bind to CSPG4 when it preferentially recognizes its target antigen, CSPG4, in a complex mixture of proteins and/or macromolecules.

In some embodiments, an anti-CSPG4 antibody or antigen-binding portion thereof or other binding agent as described herein specifically binds to a CSPG4 polypeptide with a dissociation constant (KD) of $10^{-5}$ M (10000 nM) or less, e.g., $10^{-6}$ M, $10^{-7}$ M, $10^{-8}$ M, $10^{-9}$ M, $10^{-10}$ M, $10^{-11}$ M, $10^{-12}$ M, or less. In some embodiments, an anti-CSPG4 antibody or antigen-binding portion thereof or other binding agent as described herein specifically binds to a CSPG4 polypeptide with a dissociation constant (KD) of from about $10^{-5}$ M to $10^{-6}$ M. In some embodiments, an anti-CSPG4 antibody or antigen-binding portion thereof or other binding agent as described herein specifically binds to a CSPG4 polypeptide with a dissociation constant (KD) of from about $10^{-6}$ M to $10^{-7}$ M. In some embodiments, an anti-CSPG4 antibody or antigen-binding portion thereof or other binding agent as described herein specifically binds to a CSPG4 polypeptide with a dissociation constant (KD) of from about $10^{-7}$ M to $10^{-8}$ M. In some embodiments, an anti-CSPG4 antibody or antigen-binding portion thereof or other binding agent as described herein specifically binds to a CSPG4 polypeptide with a dissociation constant (KD) of from about $10^{-8}$ M to $10^{-9}$ M. In some embodiments, an anti-CSPG4 antibody or antigen-binding portion thereof or other binding agent as described herein specifically binds to a CSPG4 polypeptide with a dissociation constant (KD) of from about $10^{-9}$ M to $10^{-10}$ M. In some embodiments, an anti-CSPG4 antibody or antigen-binding portion thereof or other binding agent as described herein specifically binds to a CSPG4 polypeptide with a dissociation constant (KD) of from about $10^{-10}$ M to $10^{-11}$ M. In some embodiments, an anti-CSPG4 antibody or antigen-binding portion thereof or other binding agent as described herein specifically binds to a CSPG4 polypeptide with a dissociation constant (KD) of from about $10^{-11}$ M to $10^{-12}$ M. In some embodiments, an anti-CSPG4 antibody or antigen-binding portion thereof or other binding agent as described herein specifically binds to a CSPG4 polypeptide with a dissociation constant (KD) of less than $10^{-12}$ M.

As used throughout the disclosure, "identical" or "identity" refer to the similarity between a DNA, RNA, nucleotide, amino acid, or protein sequence to another DNA, RNA, nucleotide, amino acid, or protein sequence. Identity can be expressed in terms of a percentage of sequence identity of a first sequence to a second sequence. Percent (%) sequence identity with respect to a reference DNA sequence can be the percentage of DNA nucleotides in a candidate sequence that are identical with the DNA nucleotides in the reference DNA sequence after aligning the sequences. Percent (%) sequence identity with respect to a reference amino acid sequence can be the percentage of amino acid residues in a candidate sequence that are identical with the amino acid residues in the reference amino acid sequence after aligning the sequences and introducing gaps, if necessary, to achieve the maximum percent sequence identity, and not considering any conservative substitutions as part of the sequence identity. As used throughout the disclosure, the percent sequence identity values is generated using the NCBI BLAST 2.0 software as defined by Altschul et al., "Gapped BLAST and PSI-BLAST: a new generation of protein database search programs," Nucleic Acids Res. 2007, 25, 3389-3402, with the parameters set to default values.

As used herein, the term "consisting essentially of" refers to those elements required for a given embodiment. The term permits the presence of elements that do not materially affect the basic and novel or functional characteristic(s) of that embodiment.

The term "consisting of" refers to compositions, methods, and respective components thereof as described herein, which are exclusive of any element not recited in that description of the embodiment.

Other than in the examples, or where otherwise indicated, all numbers expressing quantities of ingredients or reaction conditions used herein should be understood as modified in all instances by the term "about." The term "about" when used in connection with percentages can mean+/−1%.

The term "statistically significant" or "significantly" refers to statistical significance and generally means a two standard deviation (2SD) difference, above or below a reference value.

Other terms are defined herein within the description of the various aspects of the disclosure.

I. Antibodies

Provided herein are ARD107 antibodies and humanized variants thereof (also referred to herein collectively as anti-CSPG4 antibodies or CSPG4 binding antibodies) and antigen binding portions thereof that specifically bind to CSPG4. Also provided herein are conjugates of ARD107 antibodies, humanized variants thereof, and antigen binding portions and cytotoxic agents (also referred to as CSPG4 conjugates). In some embodiments, the CSPG4 conjugates reduce the number of CSPG4+ cancer cells in a subject.

In some embodiments, the CSPG4 antibody or antigen binding portion thereof comprises: (i) a heavy chain variable region having the amino acid sequence set forth in SEQ ID NO:1, and (ii) a light chain variable region having the amino acid sequence set forth in SEQ ID NO:2; (iii) a heavy chain variable region having the amino acid sequence set forth in SEQ ID NO:25, and (iv) a light chain variable region having the amino acid sequence set forth in SEQ ID NO:30; (v) a heavy chain variable region having the amino acid sequence set forth in SEQ ID NO:27, and (vi) a light chain variable region having the amino acid sequence set forth in SEQ ID NO:30; or (vii) a heavy chain variable region having the amino acid sequence set forth in SEQ ID NO:27, and (viii) a light chain variable region having the amino acid sequence set forth in SEQ ID NO:31.

In some embodiments, the CSPG4 binding antibody or antigen binding portion thereof comprises (i) a heavy chain variable region having the amino acid sequence set forth in SEQ ID NO:1 and (ii) a light chain variable region having the amino acid sequence set forth in SEQ ID NO:2; (iii) a heavy chain variable region having the amino acid sequence set forth in SEQ ID NO:25, and (iv) a light chain variable region having the amino acid sequence set forth in SEQ ID NO:30; (v) a heavy chain variable region having the amino acid sequence set forth in SEQ ID NO:27, and (vi) a light chain variable region having the amino acid sequence set forth in SEQ ID NO:30; or (vii) a heavy chain variable region having the amino acid sequence set forth in SEQ ID NO:27, and (viii) a light chain variable region having the amino acid sequence set forth in SEQ ID NO:31, wherein the heavy and light chain variable framework regions are optionally modified with from 1 to 8, 1 to 6, 1 to 4 or 1 to 2 conservative amino acid substitutions in the framework regions, and wherein the CDRs of the heavy or light chain variable regions are not modified.

In some embodiments, the CSPG4 antibody or antigen binding portion thereof comprises (i) a heavy chain variable region having the amino acid sequence set forth in SEQ ID NO:1 and (ii) a light chain variable region having the amino acid sequence set forth in SEQ ID NO:2; (iii) a heavy chain variable region having the amino acid sequence set forth in SEQ ID NO:25, and (iv) a light chain variable region having the amino acid sequence set forth in SEQ ID NO:30; (v) a heavy chain variable region having the amino acid sequence set forth in SEQ ID NO:27, and (vi) a light chain variable region having the amino acid sequence set forth in SEQ ID NO:30; or (vii) a heavy chain variable region having the amino acid sequence set forth in SEQ ID NO:27, and (viii) a light chain variable region having the amino acid sequence set forth in SEQ ID NO:31, wherein the heavy and light chain variable framework regions are optionally modified with from 1 to 8, 1 to 6, 1 to 4 or 1 to 2 amino acid substitutions, deletions or insertions in the framework regions, and wherein the CDRs of the heavy or light chain variable regions are not modified.

In some embodiments, provided herein is a binding agent comprising: (i) a heavy chain variable region having the amino acid sequence set forth in SEQ ID NO:1, and (ii) a light chain variable region having the amino acid sequence set forth in SEQ ID NO:2; (iii) a heavy chain variable region having the amino acid sequence set forth in SEQ ID NO:25, and (iv) a light chain variable region having the amino acid sequence set forth in SEQ ID NO:30; (v) a heavy chain variable region having the amino acid sequence set forth in SEQ ID NO:27, and (vi) a light chain variable region having the amino acid sequence set forth in SEQ ID NO:30; or (vii) a heavy chain variable region having the amino acid sequence set forth in SEQ ID NO:27, and (viii) a light chain variable region having the amino acid sequence set forth in SEQ ID NO:31, wherein the binding agent specifically binds to CSPG4. In some embodiments, provided herein is a binding agent comprising (i) a heavy chain variable region having the amino acid sequence set forth in SEQ ID NO:1 and (ii) a light chain variable region having the amino acid sequence set forth in SEQ ID NO:2; (iii) a heavy chain variable region having the amino acid sequence set forth in SEQ ID NO:25, and (iv) a light chain variable region having the amino acid sequence set forth in SEQ ID NO:30; (v) a heavy chain variable region having the amino acid sequence set forth in SEQ ID NO:27, and (vi) a light chain variable region having the amino acid sequence set forth in SEQ ID NO:30; or (vii) a heavy chain variable region having the amino acid sequence set forth in SEQ ID NO:27, and (viii) a light chain variable region having the amino acid sequence set forth in SEQ ID NO:31, wherein the heavy and light chain variable framework regions are optionally modified with from 1 to 8, 1 to 6, 1 to 4 or 1 to 2 conservative amino acid substitutions in the framework regions and wherein the CDRs of the heavy or light chain variable regions are not modified. In some embodiments, provided herein is a binding agent comprising (i) a heavy chain variable region having the amino acid sequence set forth in SEQ ID NO:1 and (ii) a light chain variable region having the amino acid sequence set forth in SEQ ID NO:2; (iii) a heavy chain variable region having the amino acid sequence set forth in SEQ ID NO:25, and (iv) a light chain variable region having the amino acid sequence set forth in SEQ ID NO:30; (v) a heavy chain variable region having the amino acid sequence set forth in SEQ ID NO:27, and (vi) a light chain variable region having the amino acid sequence set forth in SEQ ID NO:30; or (vii) a heavy chain variable region having the amino acid sequence set forth in SEQ ID NO:27, and (viii) a light chain variable region having the amino acid sequence set forth in SEQ ID NO:31, wherein the heavy and light chain variable framework regions are optionally modified with from 1 to 8, 1 to 6, 1 to 4 or 1 to 2 amino acid substitutions, deletions or insertions in the framework regions and wherein the CDRs of the heavy or light chain variable regions are not modified. As described herein, a binding agent includes an anti-CSPG4 antibody or antigen binding portion(s) thereof and can include other peptides or polypeptides covalently attached to the CSPG4 antibody or antigen binding portion thereof. In any of these embodiments, the binding agent specifically binds to CSPG4.

In some embodiments, the heavy and/or light chain CDRs of an antibody or antigen binding fragment thereof may be identified by using any one of the following methods: Kabat, Chothia, AbM, Contact, IMGT, and/or Aho.

In some embodiments, provided is a binding agent comprising a heavy chain variable (VH) region and a light chain variable (VL) region, wherein the VH region comprises a complementarity determining region heavy chain complementarity determining region 1 (HCDR1) having the amino acid sequence set forth in SEQ ID NO:11, a heavy chain complementarity determining region 2 (HCDR2) having the amino acid sequence set forth in SEQ ID NO:12 and a heavy chain complementarity determining region 3 (HCDR3) having the amino acid sequence set forth in SEQ ID NO:13, and the VL region comprises a light chain complementarity determining region 1 (LCDR1) having the amino acid sequence set forth in SEQ ID NO:14, a light chain complementarity determining region 2 (LCDR2) having the amino acid sequence set forth in SEQ ID NO:15, and a light chain complementarity determining region 3 (LCDR3) having the amino acid sequence set forth in SEQ ID NO:16, as determined by IMGT, and wherein each VH and VL comprises a humanized framework region and the binding agent specifically binds to CSPG4.

In some embodiments, the compositions and methods described herein relate to reduction of CSPG4+ cells in a subject (e.g., reducing the number of CSPG4+ cells in a cancer or tumor) by an anti-CSPG4 antibody, antigen binding portion thereof, other binding agent or conjugate thereof in vivo. In some embodiments. In some embodiments, the compositions and methods described herein relate to the treatment of CSPG4+ cancer in a subject by administering an anti-CSPG4 antibody, antigen binding portion thereof, other binding agent or conjugate thereof.

As used herein, the term "antibody" refers to immunoglobulin molecules and immunologically active portions of immunoglobulin molecules, i.e., molecules that contain an antigen binding site that specifically binds to an antigen. The term generally refers to antibodies comprised of two immunoglobulin heavy chain variable regions and two immunoglobulin light chain variable regions including full length antibodies (having heavy and light chain constant regions) and antigen-binding portions thereof, including, for example, an intact monoclonal antibody, a Fab, a Fab', a $F(ab')^2$, a Fv, a disulfide linked Fv, a scFv, a single domain antibody (dAb), a diabody, a multi-specific antibody, a dual specific antibody, a bispecific antibody, and single chain antibodies (see, e.g., Huston et al., Proc. Natl. Acad. Sci. U.S.A., 85, 5879-5883 (1988) and Bird et al., Science 242, 423-426 (1988), which are incorporated herein by reference). An antibody can include, for example, polyclonal, monoclonal, and genetically engineered antibodies, and antigen binding fragments thereof. An antibody can be, for example, murine, chimeric, humanized, heteroconjugate, bispecific, diabody, triabody, or tetrabody.

Each heavy chain is typically composed of a variable region (abbreviated as VH) and a constant region. The heavy chain constant region may include three domains CH1, CH2 and CH3 and optionally a fourth domain, CH4. Each light chain is typically composed of a variable region (abbreviated as VL) and a constant region. The light chain constant region is a CL domain. The VH and VL regions may be further divided into hypervariable regions referred to as complementarity-determining regions (CDRs) and interspersed with conserved regions referred to as framework regions (FR). Each VH and VL region thus consists of three CDRs and four FRs that are arranged from the N terminus to the C terminus in the following order: FR1, CDR1, FR2, CDR2, FR3, CDR3, and FR4. This structure is well known to those skilled in the art. CDR and FR sequences may be determined by several different numbering schemes, including Kabat, Chothia, AbM, Contact, IMGT, and/or Aho.

In some embodiments, an antigen binding portion comprises a light chain complementary determining region 1 (LCDR1), a light chain complementary determining region 2 (LCDR2), a light chain complementary determining region 3 (LCDR3), a heavy chain complementary determining region 1 (HCDR1), a heavy chain complementary determining region 2 (HCDR2), and a heavy chain complementary determining region 3 (HCDR3).

The amino acid sequences of the VH CDRs of the CSPG4 antibody are set forth in SEQ ID NO:1 at amino acids 26-36 (GYSITSGYYWN, HCDR1, SEQ ID NO:11), 51-65 (YITYDGSNNY, HCDR2, SEQ ID NO:12) and 109-111 (FDY, HCDR3, SEQ ID NO:13). The amino acid sequences of the VL CDRs of the CSPG4 antibody are set forth in SEQ ID NO:2 at amino acids 24-34 (SASQGIRNYLN, LCDR1, SEQ ID NO:14), 50-56 (YTSSLHS, LCDR2, SEQ ID NO:15) and 99-107 (QQYSKLPWT, LCDR3, SEQ ID NO:16). The phrase "wherein the CDRs of the heavy or light chain variable regions are not modified" refers to these VH and VL CDRs (SEQ ID NOs:11-16) as determined by IMGT, which do not have amino acid substitutions, deletions or insertions.

As used herein, an "antigen-binding portion" or "antigen-binding fragment" of an anti-CSPG4 antibody refers to a region of an antibody molecule that specifically binds to an antigen. In some embodiments, the antigen-binding portion refers to the portions of an anti-CSPG4 antibody as described herein having the VH and VL sequences of the CSPG4 antibody (set forth in SEQ ID NO:1 and SEQ ID NO:2, SEQ ID NO:25 and SEQ ID NO:30, SEQ ID NO:27 and SEQ ID NO:30, or SEQ ID NO:27 and SEQ ID NO:31, optionally modified as described herein). In accordance with the term "antigen-binding portion" of an antibody, examples of antigen binding portions include a Fab, a Fab', a $F(ab')^2$, a Fv, a disulfide linked Fv, a scFv, a single domain antibody (dAb), a diabody, heavy chain antibody (hcAb), VHH, VNAR, nanobody, and single chain antibodies. As used herein, the terms Fab, F(ab')2 and Fv refer to the following: (i) an Fab fragment, i.e. a monovalent fragment composed of the VL, VH, CL and CH1 domains; (ii) an F(ab')2 fragment, i.e. a bivalent fragment comprising two Fab fragments linked to one another in the hinge region via a disulfide bridge; and (iii) an Fv fragment composed of the VL and VH domains of an anti-CSPG4 antibody. Although the two domains of the Fv fragment, namely VL and VH, are encoded by separate coding regions, they may further be linked to one another using a synthetic linker, e.g. a poly-G4S amino acid sequence ('(G4S)n' disclosed as SEQ ID NO: 17, wherein n=1 to 5), making it possible to prepare them as a single protein chain in which the VL and VH regions combine in order to form monovalent molecules (known as single chain Fv (ScFv)). The term "antigen-binding portion" of an antibody is also intended to include such single chain antibodies. Other forms of single chain antibodies such as "diabodies" are likewise included here. Diabodies are bivalent, bispecific antibodies in which VH and VL domains are expressed on a single polypeptide chain, but using a linker connecting the VH and VL domains that is too short for the two domains to be able to combine on the same chain, thereby forcing the VH and VL domains to pair with complementary domains of a different chain (VL and VH, respectively), and to form two antigen-binding sites (see, for example, Holliger, R, et al. (1993) Proc. Natl. Acad. Sci. USA 90:64446448; Poljak, R. J, et al. (1994) Structure 2:1121-1123).

An immunoglobulin constant region refers to a heavy or light chain constant region. The constant region provide the general framework of the antibody and may not be involved directly in binding the antibody to an antigen, but can be involved in various effector functions, such as participation of the antibody in antibody-dependent cellular cytotoxicity (ADCC), ADCP (antibody-dependent cellular phagocytosis), CDC (complement-dependent cytotoxicity) and complement fixation, binding to Fc receptors (e.g., CD16, CD32, FcRn), greater in vivo half-life relative to a polypeptide lacking an Fc region, protein A binding, and perhaps even placental transfer (see Capon et al., *Nature* 337:525, 1989). As used throughout the disclosure, "Fc region" refers to the heavy chain constant region segment of the Fc fragment (the "fragment crystallizable" region or Fc region) from an antibody, which can in include one or more constant domains, such as CH2, CH3, CH4, or any combination thereof. In some embodiments, an Fc region includes the CH2 and CH3 domains of an IgG, IgA, or IgD antibody, or the CH3 and CH4 domains of an IgM or IgE antibody.

Human heavy chain and light chain constant region amino acid sequences are known in the art. A constant region can be of any suitable type, which can be selected from the classes of immunoglobulins, IgA, IgD, IgE, IgG, and IgM. Several immunoglobulin classes can be further divided into isotypes, e.g., IgG1, IgG2, IgG3, IgG4, or IgAQ1, and IgA2. The heavy-chain constant regions (Fc) that corresponds to the different classes of immunoglobulins can be $\alpha$, $\delta$, $\varepsilon$, $\gamma$, and $\mu$, respectively. The light chains can be one of either kappa (or $\kappa$) and lambda (or $\lambda$).

In some embodiments, a constant region can have an IgG1 isotype. In some embodiments, a constant region can have an IgG2 isotype. In some embodiments, a constant region can have an IgG3 isotype. In some embodiments, a constant region can have an IgG4 isotype. In some embodiments, an Fc region can have a hybrid isotype comprising constant domains from two or more isotypes. In some embodiments, an immunoglobulin constant region can be an IgG1 or IgG4 constant region.

In some embodiments, an anti-CSPG4 antibody has an IgG1 heavy chain constant region. In some embodiments, an IgG1 heavy chain constant region has the amino acid sequence set forth in positions 113-442 of SEQ ID NO:3. In some embodiments, an anti-CSPG4 antibody has a kappa light chain constant region. In some embodiments, a kappa light chain constant region has the amino acid sequence set forth in positions 108-214 of SEQ ID NO:4.

In some embodiments, an anti-CSPG4 antibody heavy chain is of the IgG1 isotype and has the amino acid sequence set forth in SEQ ID NO:7. In some embodiments, an anti-CSPG4 antibody light chain is of the kappa isotype and has the amino acid sequence set forth in SEQ ID NO:8.

In some embodiments, an anti-CSPG4 antibody heavy chain is of the IgG1 isotype and has the amino acid sequence set forth in SEQ ID NO:33; and/or an anti-CSPG4 antibody light chain is of the kappa isotype and has the amino acid sequence set forth in SEQ ID NO:38.

In some embodiments, an anti-CSPG4 antibody heavy chain is of the IgG1 isotype and has the amino acid sequence set forth in SEQ ID NO:35; and/or an anti-CSPG4 antibody light chain is of the kappa isotype and has the amino acid sequence set forth in SEQ ID NO:38.

In some embodiments, an anti-CSPG4 antibody heavy chain is of the IgG1 isotype and has the amino acid sequence set forth in SEQ ID NO:35; and/or an anti-CSPG4 antibody light chain is of the kappa isotype and has the amino acid sequence set forth in SEQ ID NO:39.

Furthermore, an anti-CSPG4 antibody or an antigen-binding portion thereof may be part of a larger binding agent formed by covalent or noncovalent association of the antibody or antibody portion with one or more other proteins or peptides. Relevant to such binding agents are the use of the streptavidin core region in order to prepare a tetrameric scFv molecule (Kipriyanov, S. M., et al. (1995), Human Antibodies and Hybridomas 6:93-101) and the use of a cysteine residue, a marker peptide and a C-terminal polyhistidinyl peptide, e.g. hexahistidinyl tag ('hexahistidinyl tag' disclosed as SEQ ID NO: 18) in order to produce bivalent and biotinylated scFv molecules (Kipriyanov, S. M., et al. (1994) Mol. Immunol. 31:10471058).

As to the VH and VL amino acid sequences, one of skill in the art will recognize that individual substitutions, deletions or additions (insertions) to a nucleic acid encoding the VH or VL, or amino acids in polypeptide that alter a single amino acid or a small percentage of amino acids in the encoded sequence is a "conservatively modified variant", where the alteration results in the substitution of an amino acid with a chemically similar amino acid (a conservative amino acid substitution) and the altered polypeptide retains the ability to specifically bind to CSPG4.

In some embodiments, a conservatively modified variant of an anti-CSPG4 antibody or antigen binding portion thereof can have alterations in the framework regions (FR); i.e., other than in the CDRs, e.g. a conservatively modified variant of an anti-CSPG4 antibody has the amino acid sequences of the VH and VL CDRs (set forth in SEQ ID NOs: 11-16) and has at least one conservative amino acid substitution in the FR. In some embodiments, the VH and VL amino acid sequences (set forth in SEQ ID NOs: 1 and 2, SEQ ID NOs: 25 and 30, SEQ ID NOs: 27 and 30, or SEQ ID NOs:27 and 31, respectively) collectively have no more than 8 or 6 or 4 or 2 or 1 conservative amino acid substitutions in the FR, as compared to the amino acid sequences of the VH and VL (SEQ ID NOs: 1 and 2, SEQ ID NOs: 25 and 30, SEQ ID NOs: 27 and 30, or SEQ ID NOs:27 and 31, respectively). In some embodiments, the VH and VL amino acid sequences (set forth in SEQ ID NOs: 1 and 2, SEQ ID NOs: 25 and 30, SEQ ID NOs: 27 and 30, or SEQ ID NOs:27 and 31, respectively) have 8 to 1, 6 to 1, 4 to 1 or 2 to 1 conservative amino acid substitutions in the FR, as compared to the amino acid sequences of the VH and VL (set forth in SEQ ID NOs: 1 and 2, SEQ ID NOs: 25 and 30, SEQ ID NOs: 27 and 30, or SEQ ID NOs:27 and 31, respectively). In further aspects of any of these embodiments, a conservatively modified variant of the anti-CSPG4 antibody, antigen binding portion thereof or other binding agent exhibits specific binding to CSPG4.

For conservative amino acid substitutions, a given amino acid can be replaced by a residue having similar physiochemical characteristics, e.g., substituting one aliphatic residue for another (such as Ile, Val, Leu, or Ala for one another), or substitution of one polar residue for another (such as between Lys and Arg; Glu and Asp; or Gln and Asn). Other such conservative amino acid substitutions, e.g., substitutions of entire regions having similar hydrophobicity characteristics, are well known. Polypeptides comprising conservative amino acid substitutions can be tested in any one of the assays described herein to confirm that a desired activity, e.g. antigen-binding activity and specificity of a native or reference polypeptide is retained, i.e., to CSPG4.

For conservative substitutions, amino acids can be grouped according to similarities in the properties of their side chains (in A. L. Lehninger, in Biochemistry, second ed., pp. 73-75, Worth Publishers, New York (1975)): (1) non-polar: Ala (A), Val (V), Leu (L), Ile (I), Pro (P), Phe (F), Trp (W), Met (M); (2) uncharged polar: Gly (G), Ser (S), Thr (T), Cys (C), Tyr (Y), Asn (N), Gln (Q); (3) acidic: Asp (D), Glu (E); and (4) basic: Lys (K), Arg (R), His (H).

Alternatively, for conservative substitutions naturally occurring residues can be divided into groups based on common side-chain properties: (1) hydrophobic: Norleucine, Met, Ala, Val, Leu, Ile; (2) neutral hydrophilic: Cys, Ser, Thr, Asn, Gln; (3) acidic: Asp, Glu; (4) basic: His, Lys, Arg; (5) residues that influence chain orientation: Gly, Pro; and (6) aromatic: Trp, Tyr, Phe. Non-conservative substitutions will entail exchanging a member of one of these classes or another class.

Particular conservative substitutions include, for example; Ala to Gly or to Ser; Arg to Lys; Asn to Gln or to His; Asp to Glu; Cys to Ser; Gln to Asn; Glu to Asp; Gly to Ala or to Pro; His to Asn or to Gln; Ile to Leu or to Val; Leu to Ile or to Val; Lys to Arg, to Gln or to Glu; Met to Leu, to Tyr or to Ile; Phe to Met, to Leu or to Tyr; Ser to Thr; Thr to Ser; Trp to Tyr; Tyr to Trp; and/or Phe to Val, to Ile or to Leu.

In some embodiments, a conservatively modified variant of an anti-CSPG4 antibody or antigen binding portion thereof preferably is at least 90%, at least 91%, at least 92%, at least 93%, at least 94%, at least 95%, at least 96%, at least 97%, at least 98%, at least 99%, or more, identical to the reference VH or VL sequence, wherein the VH and VL CDRs (SEQ ID NOs:11-16) are not modified. As used throughout the disclosure, "identical" or "identity" refer to the similarity between a DNA, RNA, nucleotide, amino acid, or protein sequence to another DNA, RNA, nucleotide, amino acid, or protein sequence. Identity can be expressed in terms of a percentage of sequence identity of a first sequence to a second sequence. Percent (%) sequence identity with respect to a reference DNA sequence can be the percentage of DNA nucleotides in a candidate sequence that are identical with the DNA nucleotides in the reference DNA sequence after aligning the sequences. Percent (%) sequence identity with respect to a reference amino acid sequence can be the percentage of amino acid residues in a candidate sequence that are identical with the amino acid residues in the reference amino acid sequence after aligning the sequences and introducing gaps, if necessary, to achieve the maximum percent sequence identity, and not considering any conservative substitutions as part of the sequence identity. As used throughout the disclosure, the percent sequence identity values is generated using the NCBI BLAST 2.0 software as defined by Altschul et al., "Gapped BLAST and PSI-BLAST: a new generation of protein database search programs," Nucleic Acids Res. 2007, 25, 3389-3402, with the parameters set to default values.

In some embodiments, the VH and VL amino acid sequences (set forth in SEQ ID NOs:1 and 2, SEQ ID NOs: 25 and 30, SEQ ID NOs: 27 and 30, or SEQ ID NOs:27 and 31, respectively) collectively have no more than 8 or 6 or 4 or 2 or 1 conservative amino acid substitutions in the framework regions, as compared to the amino acid sequences of the VH and VL (set forth in SEQ ID NOs: 1 and 2, SEQ ID NOs: 25 and 30, SEQ ID NOs: 27 and 30, or SEQ ID NOs:27 and 31, respectively). In some embodiments, the VH and VL amino acid sequences (set forth in SEQ ID Nos: 1 and 2, respectively) collectively have 8 to 1, or 6 to 1, or 4 to 1, or 2 to 1 conservative amino acid substitutions in the framework regions, as compared to the amino acid sequences of the VH and VL (set forth in SEQ ID NOs: 1 and 2, SEQ ID NOs: 25 and 30, SEQ ID NOs: 27 and 30, or SEQ ID NOs:27 and 31, respectively). In some embodiments, the VH and VL amino acid sequences (set forth in SEQ ID NOs: 1 and 2, SEQ ID NOs: 25 and 30, SEQ ID NOs: 27 and 30, or SEQ ID NOs:27 and 31, respectively) collectively have no more than 8 or 6 or 4 or 2 or 1 amino acid substitutions, deletions or insertions in the framework regions, as compared to the amino acid sequences of the VH and VL (set forth in SEQ ID NOs: 1 and 2, respectively). In some embodiments, the VH and VL amino acid sequences (set forth in SEQ ID NOs: 1 and 2, respectively) have 8 to 1, 6 to 1, 4 to 1, or 2 to 1 conservative amino acid substitutions in the framework regions, as compared to the amino acid sequences of the VH and VL (set forth in SEQ ID NOs: 1 and 2, SEQ ID NOs: 25 and 30, SEQ ID NOs: 27 and 30, or SEQ ID NOs:27 and 31, respectively). In some embodiments, the VH and VL amino acid sequences (set forth in SEQ ID NOs:1 and 2, SEQ ID NOs: 25 and 30, SEQ ID NOs: 27 and 30, or SEQ ID NOs:27 and 31, respectively) collectively have no more than 8 or 6 or 4 or 2 or 1 amino acid substitutions, deletions or insertions, as compared to the amino acid sequences of the VH and VL (set forth in SEQ ID NOs:1 and 2, SEQ ID NOs: 25 and 30, SEQ ID NOs: 27 and 30, or SEQ ID NOs:27 and 31, respectively).

Modification of a native (or reference) amino acid sequence can be accomplished by any of a number of techniques known to one of skill in the art. Mutations can be introduced, for example, at particular loci by synthesizing oligonucleotides containing the desired mutant sequence, flanked by restriction sites enabling ligation to fragments of the native sequence. Following ligation, the resulting reconstructed sequence encodes a variant having the desired amino acid insertion, substitution, or deletion. Alternatively, oligonucleotide-directed site-specific mutagenesis procedures can be employed to provide an altered nucleotide sequence having particular codons altered according to the substitution, deletion, or insertion desired. Techniques for making such alterations are very well established and include, for example, those disclosed by Walder et al. (Gene 42:133, 1986); Bauer et al. (Gene 37:73, 1985); Craik (BioTechniques, January 1985, 12-19); Smith et al. (Genetic Engineering: Principles and Methods, Plenum Press, 1981); and U.S. Pat. Nos. 4,518,584 and 4,737,462, which are herein incorporated by reference in their entireties.

In some embodiments, an anti-CSPG4 antibody or antigen-binding portion thereof has fully human constant regions. In some embodiments, an anti-CSPG4 antibody or antigen-binding portion thereof has non-human constant regions. In some embodiments, an anti-CSPG4 antibody or antigen-binding portion thereof has chimeric (part human, part non-human) constant regions.

In various embodiments, anti-CSPG4 antibodies, antigen binding portions thereof and other binding agents can be produced in human, murine or other animal-derived cells lines. Recombinant DNA expression can be used to produce anti-CSPG4 antibodies, antigen binding portions thereof and other binding agents. This allows the production of anti-CSPG4 antibodies as well as a spectrum of anti-CSPG4 antigen binding portions and other binding agents (including fusion proteins) in a host species of choice. The production of anti-CSPG4 antibodies, antigen binding portions thereof and other binding agents in bacteria, yeast, transgenic animals and chicken eggs are also alternatives for cell-based production systems. The main advantages of transgenic animals are potential high yields from renewable sources.

In some embodiments, an anti-CSPG4 VH polypeptide having the amino acid sequence set forth in SEQ ID NO: 1 is encoded by a nucleic acid. In some embodiments, a CSPG4 VL polypeptide having the amino acid sequence set forth in SEQ ID NO: 2 is encoded by a nucleic acid. In some embodiments, an anti-CSPG4 VH polypeptide having the amino acid sequence set forth in SEQ ID NO: 1 is encoded by a nucleic acid having the sequence set forth in SEQ ID NO:21. In some embodiments, an anti-CSPG4 VL polypeptide having the amino acid sequence set forth in SEQ ID NO: 2 is encoded by a nucleic acid having the sequence set forth in SEQ ID NO:22.

In some embodiments, an anti-CSPG4 VH polypeptide having the amino acid sequence set forth in SEQ ID NO: 25 is encoded by a nucleic acid. In some embodiments, a CSPG4 VL polypeptide having the amino acid sequence set forth in SEQ ID NO: 30 is encoded by a nucleic acid. In some embodiments, an anti-CSPG4 VH polypeptide having the amino acid sequence set forth in SEQ ID NO: 25 is encoded by a nucleic acid having the conjugated to a linker by a C-terminal carboxyl group that forms an amide bond with the Linker Unit (LU) as described in U.S. Pat. No. 9,463,252, incorporated herein by reference. In various embodiments, the Linker unit comprises at least one amino acid. Binder-drug conjugates (ADCs) of N,N-dialkylauristatins are disclosed in U.S. Pat. No. 8,992,932

In various embodiments, the linker also comprises a stretcher unit and/or an amino acid unit. Exemplary stretcher units and amino acid units are described in U.S. Pat. Nos. 9,345,785 and 9,078,931, each of which is herein incorporated by reference.

In various embodiments, provided herein is the use of antibody drug conjugates comprising an anti-CSPG4 antibody, covalently linked to MMAE through an mc-val-cit-PAB linker. The CSPG4 conjugates are delivered to the subject as a pharmaceutical composition.

In some embodiments, the CSPG4 conjugates have the following formula:

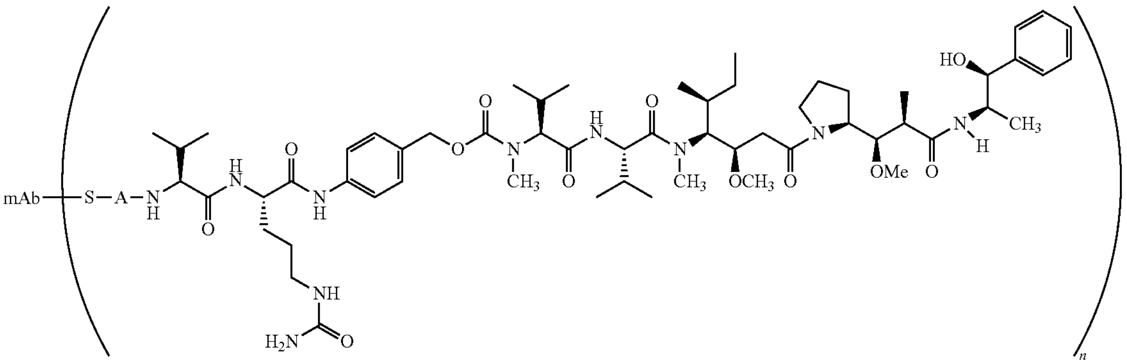

or a pharmaceutically acceptable salt thereof; wherein: mAb is an anti-CSPG4 antibody, S is a sulfur atom of the antibody, A- is a Stretcher unit, and n is from about 3 to about 5, or from about 3 to about 8.

In various embodiments, provided herein is the use of antibody drug conjugates comprising an anti-CSPG4 antibody, covalently linked to MMAE through a maleimide acetyl-Gly-Val-Cit-PAB linker.

The drug loading is represented by p, the average number of drug molecules (cytotoxic agents) per antibody in a pharmaceutical composition. For example, if p is about 4, the average drug loading taking into account all of the antibody present in the pharmaceutical composition is about 4. In some embodiments, P ranges from about 3 to about 5, more preferably from about 3.6 to about 4.4, even more preferably from about 3.8 to about 4.2. P

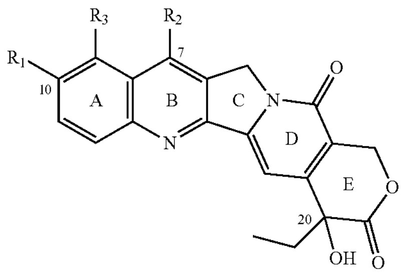

CPT: $R_1 = R_2 = R_3 = H$

10-Hydroxy-CPT: $R_1 = OH$; $R_2 = R_3 = H$

-continued

CPT-11: $R_1 =$ 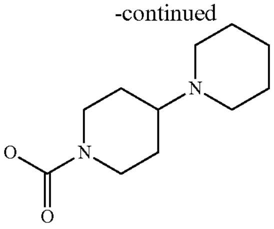 ; $R_2$ = ethyl; $R_3 = H$

SN-38: $R_1 = OH$; $R_2$ = ethyl; $R_3 = H$

Topotecan: $R_1 = OH$; $R_2 = H$;

$R_3 = CH_2—N(CH_3)_2$

Referring to the conjugate formula Ab-[L3]-[L2]-[L1]$_m$-AA$_n$-cytotoxic agent, in some embodiments, m is 0. In such embodiments, an ester moiety is first formed between the carboxylic acid of an amino acid (AA) such as glycine, alanine, or sarcosine, or of a peptide such as glycylglycine, and a hydroxyl group of a cytotoxic agent. In this example, the N-terminus of the amino acid or polypeptide may be protected as a Boc or a Fmoc or a monomethoxytrityl (MMT) derivative, which is deprotected after formation of an ester bond with the hydroxyl group of the cytotoxic agent. Selective removal of amine-protecting group, in the presence of a BOC protecting group at a hydroxyl position of the cytotoxic agent containing an additional hydroxyl group(s) can be achieved using monomethoxytrityl (MMT) as the protecting group for the amino group of amino acid or polypeptide involved in ester formation, since 'MMT' is removable by mild acid treatment such as dichloroacetic acid that does not cleave a BOC group. After the amino group of the amino acid or polypeptide, forming an ester bond with hydroxyl of the cytotoxic agent, is demasked, the amino group is reacted with the activated form of a COOH group on PEG moiety of L2 under standard amide-forming conditions. In a preferred embodiment, L3 comprises a thiol-reactive group which links to thiol groups of the antibody. The thiol-reactive group is optionally a maleimide or vinylsulfone, or bromoacetamide, or iodoacetamide, which links to a thiol group of the antibody. In some embodiments, the reagent bearing a thiol-reactive group is

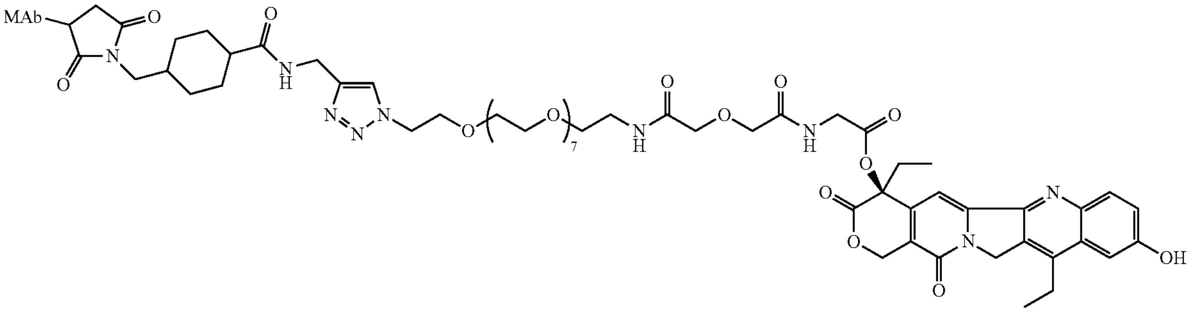

In another representative conjugate, prepared with a maleimide-containing SN-38-linker derivative, with the bonding to an antibody (MAb) represented as a succinimide, is shown below. Here, n=0 in the general formula 2; 'L1' contains a cathepsin-B-cleavable dipeptide attached to the collapsible p-aminobenzyl alcohol moiety, and the latter is attached to SN-38 as a carbonate bonding at the 20 position; azide-acetylene coupling joining the 'L2' and 'L3' results in the triazole moiety as shown.

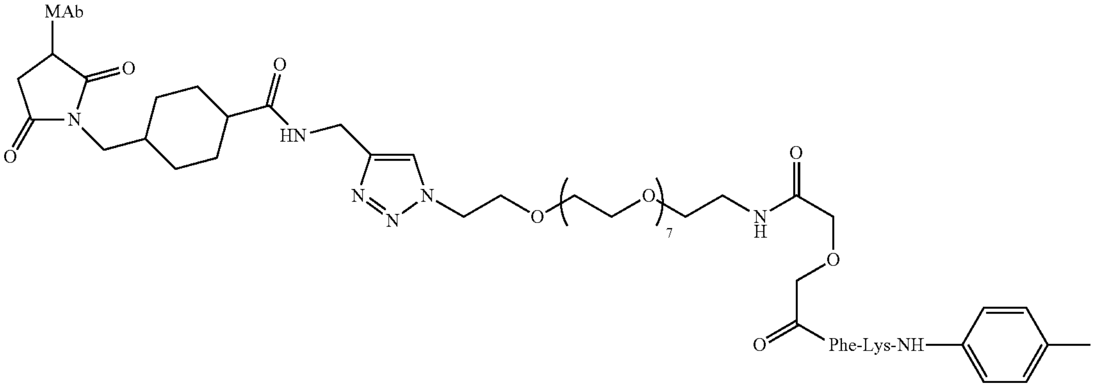

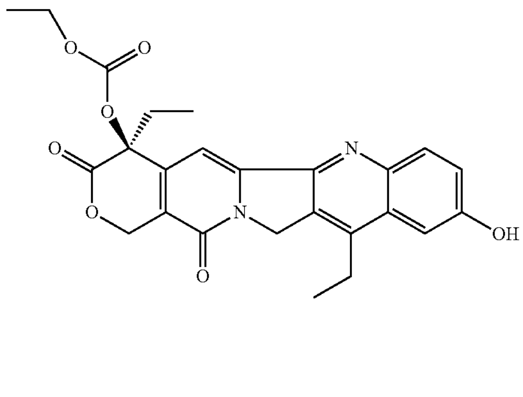

Another representative SN-38 conjugate, Mab-CL2-SN-38, prepared with a maleimide-containing SN-38-linker derivative, with the bonding to an antibody represented as a succinimide, is given below. Here, the 20-O-AA ester bonding to SN-38 is glycinate that

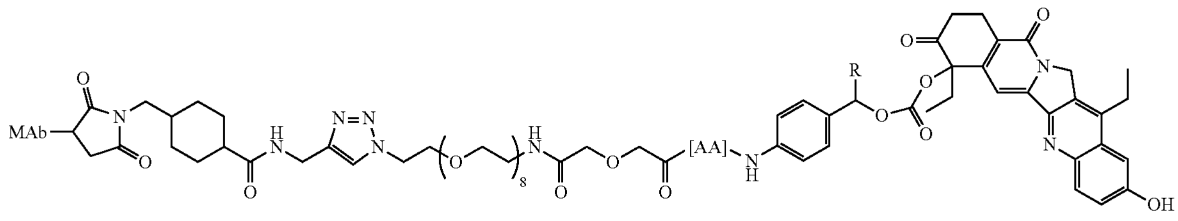

An embodiment of MAb-CLX-SN-38 (above), wherein the single amino acid AA is L-lysine and R=H, and the cytotoxic agent is exemplified by SN-38 (referred to as MAb-CL2A-SN-38) is shown below:

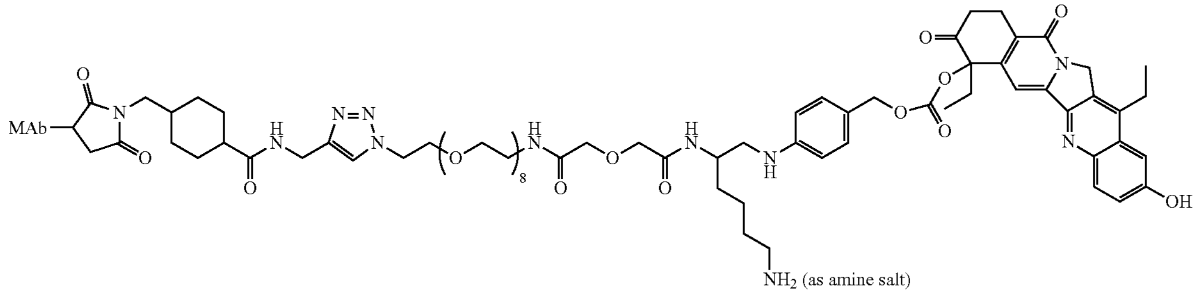

In other embodiments, a cytotoxic agent is attached to a linker comprising a Stretcher unit (Z) attached to an Amino Acid unit (AA) attached to a Spacer unit (Y), where the Stretcher unit is attached to the antibody (Ab or MAb) and the Spacer unit is attached to an amino group of a cytotoxic agent. Such a linker has the following formula:

Ab-Z-AA-Y-cytotoxic agent, where Z is selected from -(Succinimid-3-yl-N)—$(CH_2)_n{}^2$—C(═O)—, —$CH_2$—C(═O)—NH—$(CH_2)n^3$-C(═O)—, —C(═O)-cyc.Hex(1,4)-$CH_2$—(N-ly-3-diminiccuS)-, or —C(═O)—(CH2)$n^4$-C(═O)—, wherein $n^2$ represents an integer of 2 to 8, $n^3$ represents an integer of 1 to 8, and $n^4$ represents an integer of 1 to 8; cyc.Hex(1,4) represents a 1,4-cyclohexylene group; and (N-ly-3-diminiccuS)- has a structure represented by the following formula:

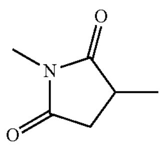

avelumab, BMS-936559, durvalumab (MEDI4736), MSB0010718C, and combinations thereof.

Suitable anti-PD-1 and anti-PD-L1 antibodies are also described in Topalian, et al., Immune Checkpoint Blockade: A Common Denominator Approach to Cancer Therapy, Cancer Cell 27: 450-61 (Apr. 13, 2015), incorporated herein by reference in its entirety.

In some embodiments, the immune checkpoint inhibitor is Ipilimumab (Yervoy®), Nivolumab (Opdivo®), Pembrolizumab (Keytruda®), Atezolizumab (Tecentriq®), Avelumab (Bavencio®), or Durvalumab (Imfinzi®).

In some embodiments, provided is a method of improving treatment outcome in a subject receiving immunotherapy. The method generally includes administering an effective amount of an immunotherapy to the subject having cancer; and administering a therapeutically effective amount of a CSPG4 binding agent or conjugate or a pharmaceutical composition thereof to the subject, wherein the binding agent or conjugate specifically binds to CSPG4+ cancer cells; wherein the treatment outcome of the subject is improved, as compared to administration of the immunotherapy alone. In some embodiments, the binding agent or conjugate thereof comprises (i) a heavy chain variable region having the amino acid sequence set forth in SEQ ID NO:1, and (ii) a light chain variable region having the amino acid sequence set forth in SEQ ID NO:2; (iii) a heavy chain variable region having the amino acid sequence set forth in SEQ ID NO:25, and (iv) a light chain variable region having the amino acid sequence set forth in SEQ ID NO:30; (v) a heavy chain variable region having the amino acid sequence set forth in SEQ ID NO:27, and (vi) a light chain variable region having the amino acid sequence set forth in SEQ ID NO:30; or (vii) a heavy chain variable region having the amino acid sequence set forth in SEQ ID NO:27, and (viii) a light chain variable region having the amino acid sequence set forth in SEQ ID NO:31, wherein the heavy and light chain framework regions are optionally modified with from 1 to 8 amino acid substitutions, deletions or insertions in the framework regions. In some embodiments, the binding agent or conjugate thereof comprises (i) a heavy chain variable region having the amino acid sequence set forth in SEQ ID NO:1, and (ii) a light chain variable region having the amino acid sequence set forth in SEQ ID NO:2; (iii) a heavy chain variable region having the amino acid sequence set forth in SEQ ID NO:25, and (iv) a light chain variable region having the amino acid sequence set forth in SEQ ID NO:30; (v) a heavy chain variable region having the amino acid sequence set forth in SEQ ID NO:27, and (vi) a light chain variable region having the amino acid sequence set forth in SEQ ID NO:30; or (vii) a heavy chain variable region having the amino acid sequence set forth in SEQ ID NO:27, and (viii) a light chain variable region having the amino acid sequence set forth in SEQ ID NO:31, wherein the binding agent specifically binds to CSPG4+ cancer cells. In some embodiments, the binding agent is an antibody or an antigen-binding portion thereof. In some embodiments, the binding agent is a monoclonal antibody, a Fab, a Fab', an F(ab'), an Fv, a disulfide linked Fc, a scFv, a single domain antibody, a diabody, a bi-specific antibody, or a multi-specific antibody. In some embodiments, the binding agent is a conjugate of an anti-CSPG4 monoclonal antibody, a Fab, a Fab', an F(ab'), an Fv, a disulfide linked Fc, a scFv, a single domain antibody, a diabody, a bi-specific antibody, or a multi-specific antibody.

In some embodiments, the improved treatment outcome is an objective response selected from stable disease, a partial response or a complete response as determined by standard medical criteria for the cancer being treated. In some embodiments, the improved treatment outcome is reduced tumor burden. In some embodiments, the improved treatment outcome is progression-free survival or disease-free survival.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. These and other changes can be made to the disclosure in light of the detailed description.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

All patents and other publications identified are expressly incorporated herein by reference for the purpose of describing and disclosing, for example, the methodologies described in such publications that might be used in connection with the present disclosure. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The present disclosure is further illustrated by the following embodiments which should not be construed as limiting.

1. A conjugate comprising: a binding agent comprising (i) a heavy chain variable (VH) region having the amino acid sequence set forth in SEQ ID NO:1, and a light chain variable (VL) region having the amino acid sequence set forth in SEQ ID NO:2; (ii) a heavy chain variable region having the amino acid sequence set forth in SEQ ID NO:25, and a light chain variable region having the amino acid sequence set forth in SEQ ID NO:30; (iii) a heavy chain variable region having the amino acid sequence set forth in SEQ ID NO:27, and a light chain variable region having the amino acid sequence set forth in SEQ ID NO:30; or (iv) a heavy chain variable region having the amino acid sequence set forth in SEQ ID NO:27, and a light chain variable region having the amino acid sequence set forth in SEQ ID NO:31;

wherein the heavy and light chain framework regions are optionally modified with from 1 to 8 amino acid substitutions, deletions or insertions in the framework regions, wherein the binding agent specifically binds to human CSPG4; at least one linker attached to the binding agent; and at least one cytotoxic agent attached to each linker.

2. The conjugate of embodiment 1, wherein the binding agent comprises: (i) a heavy chain variable region having the amino acid sequence set forth in SEQ ID NO:1, and a light chain variable region having the amino acid sequence set forth in SEQ ID NO:2; (ii) a heavy chain variable region having the amino acid sequence set forth in SEQ ID NO:25, and a light chain variable region having the amino acid sequence set forth in SEQ ID NO:30; (iii) a heavy chain variable region having the amino acid sequence set forth in SEQ ID NO:27, and a light chain variable region having the amino acid sequence set forth in SEQ ID NO:30; or (iv) a heavy chain variable region having the amino acid sequence set forth in SEQ ID NO:27, and a light chain variable region having the amino acid sequence set forth in SEQ ID NO:31.

3. A conjugate comprising: a binding agent comprising a heavy chain variable (VH) region and a light chain variable (VL) region, wherein the VH region comprises a complementarity determining region HCDR1 sequence having the amino acid sequence set forth in SEQ ID NO:11, a HCDR2 having the amino acid sequence set forth in SEQ ID NO:12, and a HCDR3 having the amino acid sequence set forth in SEQ ID NO:13, each disposed within a heavy chain framework region; and wherein the VL region comprises a LCDR1 sequence having the amino acid sequence set forth in SEQ ID NO:14, a LCDR2 having the amino acid sequence set forth in SEQ ID NO:15, and a LCDR3 having the amino acid sequence set forth in SEQ ID NO:16, each disposed within a light chain framework region; at least one linker attached to the binding agent; and at least one cytotoxic agent attached to each linker.

4. The conjugate of embodiment 3, wherein the framework regions are murine framework regions.

5. The conjugate of embodiment 3, wherein the framework regions are human framework regions.

6. The conjugate of any one of embodiments 1 to 5, wherein the binding agent is an antibody or an antigen-binding portion thereof.
7. The conjugate of embodiment 6, wherein the binding agent is a monoclonal antibody, a Fab, a Fab', an F(ab'), an Fv, a disulfide linked Fc, a scFv, a single domain antibody, a diabody, a bi-specific antibody, or a multi-specific antibody.
8. The conjugate of any of the preceding embodiment, wherein the heavy chain variable region further comprises a heavy chain constant region.
9. The conjugate of embodiment 8, wherein heavy chain constant region is of the human IgG isotype.
10. The conjugate of embodiment 9, wherein the heavy chain constant region is an IgG1 constant region.
11. The conjugate of embodiment 10, wherein the IgG1 heavy chain constant region has the amino acid sequence set forth in positions 113-442 of SEQ ID NO:3.
12. The conjugate of embodiment 9, wherein the heavy chain constant region is an IgG4 constant region.
13. The conjugate of embodiment 10, wherein the heavy chain variable and constant regions have the amino acid sequence set forth in any one of SEQ ID NOS: 3, 33 and 35.
14. The conjugate of any of the preceding embodiments, wherein the light chain variable region further comprises a light chain constant region.
15. The conjugate of embodiment 14, wherein the light chain constant region is of the kappa isotype.
16. The conjugate of embodiment 15, wherein the kappa light chain constant region has the amino acid sequence set forth in positions 108-214 of SEQ ID NO:4.
17. The conjugate of embodiment 15 or 16, wherein the light chain variable and constant regions have the amino acid sequence set forth in any one of SEQ ID NOS:4, 38 and 39.
18. The conjugate of any one of embodiments 1-17, wherein: (a) the heavy chain variable and constant regions have the amino acid sequence set forth SEQ ID NO:3, and the light chain variable and constant regions have the amino acid sequence set forth in SEQ ID NO:4; (b) the heavy chain variable and constant regions have the amino acid sequence set forth SEQ ID NO:33, and the light chain variable and constant regions have the amino acid sequence set forth in SEQ ID NO:38; (c) the heavy chain variable and constant regions have the amino acid sequence set forth SEQ ID NO:35, and the light chain variable and constant regions have the amino acid sequence set forth in SEQ ID NO:38; or (d) the heavy chain variable and constant regions have the amino acid sequence set forth SEQ ID NO:35, and the light chain variable and constant regions have the amino acid sequence set forth in SEQ ID NO:39.
19. The conjugate of any of embodiments 1 to 18, wherein the linker is attached to the binding agent via an interchain disulfide residue, an engineered cysteine, a glycan or modified glycan, an N-terminal residue of the binding agent or a polyhistidine residue attached to the binding agent.
20. The conjugate of any of embodiments 1 to 19, wherein the average drug loading of the conjugate is from about 1 to about 8, about 2, about 4, about 6, about 8, about 10, about 12, about 14, about 16, about 3 to about 5, about 6 to about 8 or about 8 to about 16.
21. The conjugate of any of the preceding embodiments, wherein the binding agent is mono-specific.
22. The conjugate of any of embodiments 1 to 21, wherein the binding agent is bivalent.
23. The conjugate of any of embodiments 1 to 20, wherein the binding agent comprises a second binding domain and the binding agent is bispecific.
24. The conjugate of any of the preceding embodiments, wherein the cytotoxic agent is selected from the group consisting of an auristatin, a camptothecin and a calicheamicin.
25. The conjugate of embodiment 24, wherein the cytotoxic agent is an auristatin.
26. The conjugate of embodiment 25, wherein the cytotoxic agent is monomethyl auristatin E (MMAE).
27. The conjugate of embodiment 24, wherein the cytotoxic agent is a camptothecin.
28. The conjugate of embodiment 27, wherein the cytotoxic agent is exatecan.
29. The conjugate of embodiment 24, wherein the cytotoxic agent is a calicheamicin.
30. The conjugate of embodiment 29, wherein the cytotoxic agent is SN-38.
31. The conjugate of any of the preceding embodiments, wherein the linker is selected from the group consisting of mc-VC-PAB, CL2, CL2A, maleimide acetyl-Gly-Val-Cit-PAB, and (Succinimid-3-yl-N)—(CH2)$_n^2$-C(═O)-Gly-Gly-Phe-Gly-NH—CH2═OCH$_2$—(C═O)—.
32. The conjugate of embodiment 31, wherein the linker is mc-VC-PAB.
33. The conjugate of embodiment 32, wherein the linker is attached to at least one molecule of MMAE.
34. The conjugate of embodiment 31, wherein the linker is CL2A.
35. The conjugate of embodiment 34, attached to at least one molecule of SN-38.
36. The conjugate of embodiment 31, wherein the linker is CL2.
37. The conjugate of embodiment 36, attached to at least one molecule of SN-38.
38. The conjugate of embodiment 31, wherein the linker is (Succinimid-3-yl-N)—(CH2)$_n^2$-C(═O)-Gly-Gly-Phe-Gly-NH—CH$_2$═OCH$_2$—(C═O)—.
39. The conjugate of embodiment 38, wherein the linker is attached to at least one molecule of exatecan.
40. A pharmaceutical composition comprising the conjugate of any of the preceding embodiments and a pharmaceutically acceptable carrier.
41. A method of treating a CSPG4+ cancer, comprising administering to a subject in need thereof a therapeutically effective amount of the conjugate of any of embodiments 1 to 39 or the pharmaceutical composition of embodiment 40.
42. The method of embodiment 41, wherein the CSPG4+ cancer is a carcinoma or a malignancy.
43. The method of embodiment 42, wherein the CSPG4+ cancer is selected from melanoma, head and neck cancer, breast cancer, mesothelioma, renal clear cell cancer, chondrosarcoma, urothelial (bladder) cancer, osteosarcoma, pancreatic cancer, and leukemia (B-ALL).
44. The method of any of embodiments 41 to 43, further comprising administering an immunotherapy to the subject.
45. The method of embodiment 44, wherein the immunotherapy comprises an immune checkpoint inhibitor.

46. The method of embodiment 45, wherein the immune checkpoint inhibitor is selected from an antibody that specifically binds to human PD-1, human PD-L1, or human CTLA4.
47. The method of embodiment 46, wherein the immune checkpoint inhibitor is pembrolizumab, nivolumab, cemiplimab or ipilimumab.
48. The method of any of embodiments 41 to 47, further comprising administering chemotherapy to the subject.
49. The method of any of embodiments 41 to 48, wherein the conjugate is administered intravenously.
50. The method of any of embodiments 41 to 49, wherein the conjugate is administered in a dose of about 0.1 mg/kg to about 10 mg/kg or from about 0.1 mg/kg to about 12 mg/kg.
51. A method of improving treatment outcome in a subject receiving immunotherapy and/or chemotherapy for a CSPG4+ cancer, comprising:

administering an effective amount of an immunotherapy or chemotherapy to the subject having cancer; and administering a therapeutically effective amount of the conjugate of any of embodiments 1 to 39 or the pharmaceutical composition of embodiment 40 to the subject;

wherein the treatment outcome of the subject is improved, as compared to administration of the immunotherapy or chemotherapy alone.

52. The method of embodiment 51, wherein the improved treatment outcome is an objective response selected from stable disease, a partial response or a complete response.
53. The method of embodiment 51, wherein the improved treatment outcome is reduced tumor burden.
54. The method of embodiment 51, wherein the improved treatment outcome is progression-free survival or disease-free survival.
55. The method of embodiment 51, wherein the immunotherapy is an immune checkpoint inhibitor.
56. The method of embodiment 55, wherein the immune checkpoint inhibitor comprises an antibody that specifically binds to human PD-1, human PD-L1, or CTLA4.
57. The method of embodiment 56, wherein the immune checkpoint inhibitor is pembrolizumab, nivolumab, cemiplimab or ipilimumab.
58. The method of any of embodiments 51 to 57, wherein the conjugate is administered intravenously.
59. The method of any of embodiments 51 to 58, wherein the conjugate is administered in a dose of about 0.1 mg/kg to about 10 mg/kg.
60. Use of the conjugate of any of embodiments 1 to 36 or the pharmaceutical composition of embodiment 37 for the treatment of CSPG4+ cancer in a subject.
61. Use of the conjugate of any of embodiments 1 to 36 or the pharmaceutical composition of embodiment 37 for the treatment of CSPG4+ cancer in a subject receiving immunotherapy or chemotherapy.
62. A binding agent comprising: (a) a heavy chain variable (VH) region having the amino acid sequence set forth in SEQ ID NO:25, and a light chain variable (VL) region having the amino acid sequence set forth in SEQ ID NO:30; (b) a heavy chain variable (VH) region having the amino acid sequence set forth in SEQ ID NO:27, and a light chain variable (VL) region having the amino acid sequence set forth in SEQ ID NO:30; or (c) a heavy chain variable (VH) region having the amino acid sequence set forth in SEQ ID NO:27, and a light chain variable (VL) region having the amino acid sequence set forth in SEQ ID NO:31; wherein the heavy and light chain framework regions are optionally modified with from 1 to 8 amino acid substitutions, deletions or insertions in the framework regions, and wherein the binding agent specifically binds to human CSPG4.
63. The binding agent of embodiment 62, wherein: (a) a heavy chain variable region having the amino acid sequence set forth in SEQ ID NO:25, and a light chain variable region having the amino acid sequence set forth in SEQ ID NO:30; (b) a heavy chain variable region having the amino acid sequence set forth in SEQ ID NO:27, and a light chain variable region having the amino acid sequence set forth in SEQ ID NO:30; or (c) a heavy chain variable region having the amino acid sequence set forth in SEQ ID NO:27, and a light chain variable region having the amino acid sequence set forth in SEQ ID NO:31.
64. The binding agent of embodiment 63, wherein the framework regions are murine framework regions.
65. The binding agent of embodiment 63, wherein the framework regions are human framework regions.
66. The binding agent of any one of embodiments 62 to 65, wherein the binding agent is an antibody or an antigen-binding portion thereof.
67. The binding agent of embodiment 66, wherein the binding agent is a monoclonal antibody, a Fab, a Fab', an F(ab'), an Fv, a disulfide linked Fc, a scFv, a single domain antibody, a diabody, a bi-specific antibody, or a multi-specific antibody.
68. The binding agent of any one of embodiments 62-67, wherein the heavy chain variable region further comprises a heavy chain constant region.
69. The binding agent of embodiment 68, wherein heavy chain constant region is of the human IgG isotype.
70. The binding agent of embodiment 69, wherein the heavy chain constant region is an IgG1 constant region.
71. The binding agent of embodiment 70, wherein the IgG1 heavy chain constant region has the amino acid sequence set forth in positions 113-442 of SEQ ID NO:3.
72. The binding agent of embodiment 69, wherein the heavy chain constant region is an IgG4 constant region.
73. The binding agent of embodiment 70 or 71, wherein the heavy chain variable and constant regions have the amino acid sequence set forth in SEQ ID NO: 33 or 35.
74. The binding agent of any one of embodiments 62-73, wherein the light chain variable region further comprises a light chain constant region.
75. The binding agent of embodiment 74, wherein the light chain constant region is of the kappa isotype.
76. The binding agent of embodiment 75, wherein the kappa light chain constant region has the amino acid sequence set forth in positions 108-214 of SEQ ID NO:4.
77. The binding agent of embodiment 75 or 76, wherein the light chain variable and constant regions have the amino acid sequence set forth in SEQ ID NO:38 or 39.
78. The binding agent of any one of embodiments 62-77, wherein: (a) the heavy chain variable and constant regions have the amino acid sequence set forth SEQ ID NO:33, and the light chain variable and constant regions have the amino acid sequence set forth in SEQ ID NO:38; (b) the heavy chain variable and constant regions have the amino acid sequence set forth SEQ ID NO:35, and the light chain variable and constant regions have the amino acid sequence set forth in SEQ ID NO:38; or (c) the heavy chain variable and constant regions have the amino acid sequence set forth SEQ ID NO:35, and the light chain variable and constant regions have the amino acid sequence set forth in SEQ ID NO:39.

79. A pharmaceutical composition comprising the binding agent of any one of embodiments 62-78 and a pharmaceutically acceptable carrier.
80. A nucleic acid encoding the binding agent of any one of embodiments 62 to 78.
81. A vector comprising the nucleic acid of embodiment 80.
82. A cell line comprising the nucleic acid of embodiment 80 or vector of embodiment 81.
83. A method of treating a CSPG4+ cancer, comprising administering to a subject in need thereof a therapeutically effective amount of the binding agent of any one of embodiments 62 to 78 or the pharmaceutical composition of embodiment 79.
84. The method of embodiment 83, wherein the CSPG4+ cancer is a carcinoma or a malignancy.
85. The method of embodiment 84, wherein the CSPG4+ cancer is selected from melanoma, head and neck cancer, breast cancer, mesothelioma, renal clear cell cancer, chondrosarcoma, urothelial (bladder) cancer, osteosarcoma, pancreatic cancer, and leukemia (B-ALL).
86. The method of any of embodiments 83 to 85, further comprising administering an immunotherapy to the subject.
87. The method of embodiment 86, wherein the immunotherapy comprises an immune checkpoint inhibitor.
88. The method of embodiment 87, wherein the immune checkpoint inhibitor is selected from an antibody that specifically binds to human PD-1, human PD-L1, or human CTLA4.
89. The method of embodiment 88, wherein the immune checkpoint inhibitor is pembrolizumab, nivolumab, cemiplimab or ipilimumab.
90. The method of any one of embodiments 83 to 89, further comprising administering chemotherapy to the subject.
91. The method of any of one of embodiments 83 to 90, wherein the binding agent is administered intravenously.
92. The method of any one of embodiments 83 to 91, wherein the binding agent is administered in a dose of about 0.1 mg/kg to about 10 mg/kg or from about 0.1 mg/kg to about 12 mg/kg.
93. A method of improving treatment outcome in a subject receiving immunotherapy and/or chemotherapy for a CSPG4+ cancer, comprising: (a) administering an effective amount of an immunotherapy or chemotherapy to the subject having cancer; and (b) administering a therapeutically effective amount of the binding agent of any one of embodiments 62 to 78 or the pharmaceutical composition of embodiment 79 to the subject; wherein the treatment outcome of the subject is improved, as compared to administration of the immunotherapy or chemotherapy alone.
94. The method of embodiment 93, wherein the improved treatment outcome is an objective response selected from stable disease, a partial response or a complete response.
95. The method of embodiment 93, wherein the improved treatment outcome is reduced tumor burden.
96. The method of embodiment 93, wherein the improved treatment outcome is progression-free survival or disease-free survival.
97. The method of embodiment 93, wherein the immunotherapy is an immune checkpoint inhibitor.
98. The method of embodiment 97, wherein the immune checkpoint inhibitor comprises an antibody that specifically binds to human PD-1, human PD-L1, or CTLA4.
99. The method of embodiment 98, wherein the immune checkpoint inhibitor is pembrolizumab, nivolumab, cemiplimab or ipilimumab.
100. The method of any of embodiments 93 to 99, wherein the binding agent is administered intravenously.
101. The method of any one of embodiments 93 to 100, wherein the binding agent is administered in a dose of about 0.1 mg/kg to about 10 mg/kg.

EXAMPLES

Methods and Materials

The following methods and materials were used in the following examples.

Cell Culture—Melanoma cell lines (A375, A2058, SkMel31, Malme-3M), lung carcinoma cell lines (NCI-H1975, NCI-H2052), and the chondrosarcoma cell line (SW1353) were obtained from ATCC (Manassas, VA) and maintained in culture according to the vendor's directions.

Flow Cytometry—Cells were rinsed with PBS (phosphate buffered saline, pH 7.4) and harvested with Versene (Thermo Fisher) prior to incubation with FACs buffer (PBS+1% fetal bovine serum (FBS; source BioSun) containing test antibody or ADCs for 1 h at 4° C. Cells were rinsed and washed with FACs buffer (PBS+1% FBS) and detection was performed with anti-hIgG-AF488. Cells were analyzed on a FACs Canto II (BD Biosciences). Quantitative FACs (qFACs) was performed to measure the number of antigen binding sites with the DAKO QifiKit (DAKO, Carpinteria, CA), according to the manufacturer's directions.

Preparation of Conjugates—ARD107-vcMMAE (ARD107-mc-vc-PAB-MMAE) was prepared by stochastic conjugation at room temperature in sodium borate buffer, pH 7.4. Briefly, ARD107 antibody (heavy chain=SEQ ID NO:3; light chain=SEQ ID NO:4) was reduced with TCEP (tris, 2-carboxyethyl phosphine) prior to incubation with drug linker, mc-vc-pab-MMAE, at 10:1 payload: antibody ratio. Excess drug linker was removed by dialysis. Size exclusion HPLC confirmed conjugate purity (99% monomer, <1% aggregate). Drug loading as assessed by LC-MS was an average of 4.

Antibody drug conjugates that are enriched for 4-load species are created by controlling the degree of native disulfide bond reduction and the subsequent conjugation of the linker-payload onto the reduced disulfides. The antibody is partially reduced by incubation with a reducing agent such as TCEP with precise control of the reduction reaction temperature, pH, time of reduction, and the molar ratio of the reductant and the antibody. Following reduction, the antibody is then conjugated with the linker payload with precise control of the reaction temperature, pH, time of conjugation and the molar ratio of linker-payload to antibody. The conjugation reaction is then quenched to stop the conjugation reaction by the addition of a molar excess of cysteine or similar amino acid analog of cysteine. The reduction and conjugation reaction conditions are designed to enhance the yield of DAR4 species and to minimize the yield of higher loaded forms such as DAR6 and DAR8.

Antibody drug conjugates can also be enriched for 4-load species by performing a stochastic conjugation followed by selective enrichment for the 4-load species by separating the 4-load species away from the lower and higher-loaded species using a hydrophobic interaction chromatography (HIC) column.

ARD107-CL2A-SN38 (ARD107-SN-38) was prepared at room temperature in PBS buffer, pH 7.4. Briefly, ARD107 antibody was reduced with TCEP prior to incubation with drug linker, CL2A-SN38, at 10:1 ratio. The reaction was stopped with N-ethylmaleimide. Excess drug linker was removed by dialysis. Size exclusion HPLC confirmed conjugate purity (99% monomer, 1% aggregate). Drug loading as assessed by LC-MS was an average of 8.

In Vitro Cytotoxicity Assay—Cells were harvested with trypsin and plated in tissue culture media at 1000 cells per well in 96-well flat clear bottom, black-walled tissue culture plates. The next day, test compounds (ADCs prepared by serial dilution to create a 10-point dose curve) or vehicle were added. The cells were incubated for 144h. Cell viability was determined with CellTiter-Glo® (Promega, Madison, WI) following the manufacturer's directions. Data was graphed with GraphPad Prism® (GraphPad, La Jolla, CA).

Mouse Xenograft Studies—All animal experiments were conducted according to IACUC (Institutional Animal Care and Use) approved protocols following AAALAC (Association for Assessment and Accreditation of Laboratory Animal Care) guidelines. Two million A2058 or A375 melanoma cells were implanted into the right flank of Balb/c mice. Tumor growth was monitored twice weekly with caliper measurements and tumor volume calculated with the formula ($V=0.5a\times b^2$ where a=longest and b=shortest diameter). Mice were treated intravenously with test compounds when tumors reached ~150 mm3. Tumor growth, body weights, and general health of the mice were continuously monitored for 1 week after the final dose of the test agent. Data was graphed with GraphPad Prism® (GraphPad, La Jolla, CA).

Example 1: FACS Binding of ARD107 Antibody and ADC

FACs binding of ARD107 antibody and corresponding conjugates to CSPG4-positive cell lines was conducted. The melanoma A2058 and Malme-3M, the SW1353 chondrosarcoma, and the NCI-H1975 lung cell lines were incubated with increasing concentrations (8-point dose curve) of the antibody, conjugates (ARD107-vcMMAE or ARD107-SN38 (ARD107-CL2A-SN-38)), or isotype control (hIgG1) for 1 hr at 4° C. Detection was done with an anti-hIgG-AF488 secondary antibody.

Binding curves for ARD107 antibody, corresponding ADCs (conjugates), and isotype control on melanoma A2058 and Malme-3M, SW1353 chondrosarcoma, and NCI-H1975 lung cell lines are shown in FIGS. 1A-1D. The data were graphed and estimated binding constants (EC50 in table, below) were determined with GraphPad Prism® (GraphPad Software, San Diego, CA). As can be seen in FIGS. 1A-1D and accompanying table, the binding of the antibody and corresponding conjugates for each cell line was similar such that the curves almost overlapped. There was very little binding of antibody or ADC in the NCI-H1975 lung cell line.

| EC50 (nM) | A2058 | Malme-3M | SW1353 | NCI-H1975 |
|---|---|---|---|---|
| ARD107 | 0.48 | 0.59 | 0.21 | — |
| ARD107-vcMMAE | 0.59 | 0.93 | 0.27 | — |
| ARD107-SN38 | 0.53 | N/A | N/A | — |

Example 2: Comparison of Binding of ARD107 Antibody to Human Melanoma and Lung Cell Lines The CSPG4+A2058 and A375 melanoma and the lung NCI-H2052 and NCI-H1975 cell lines were incubated with increasing concentrations of the antibody (6-point dose curve) for 1 hr at 4° C. Detection was done with an anti-hIgG-AF488 secondary antibody.

Figure 2:
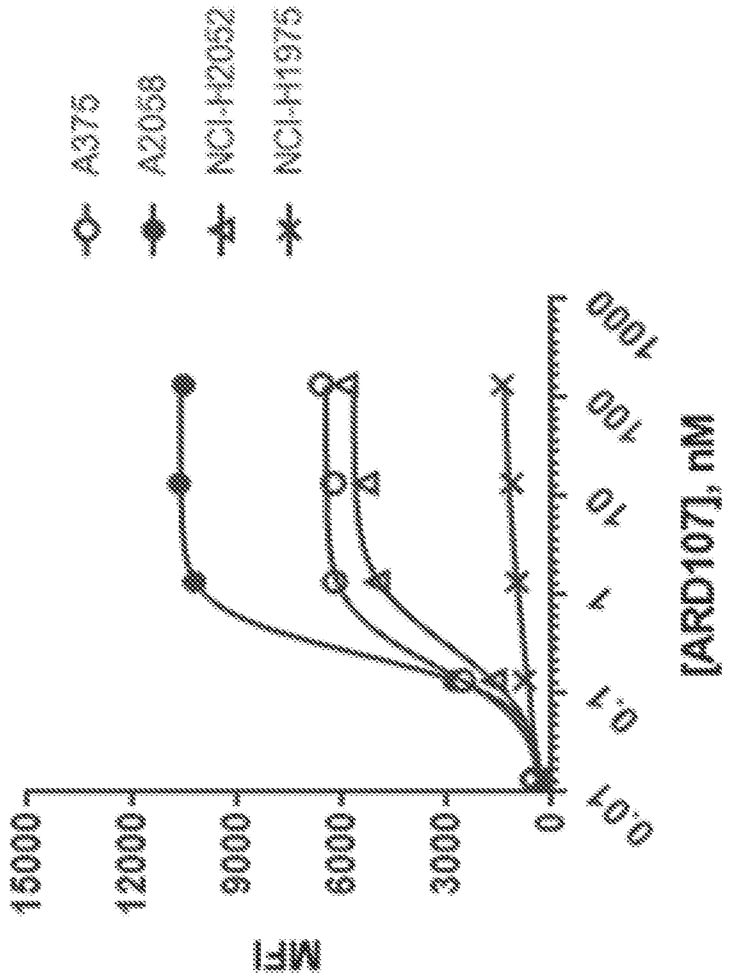
FIG. 2. Comparison of binding of ARD107 antibody to human melanoma and lung cell lines.

Binding curves for ARD107 antibody to the melanoma A2058 and Malme-3M and the lung NCI-H2052 and NCI-H1975 lung cell lines are shown in FIG. 2. The data were graphed and estimated binding constants (EC50 in table) were determined with GraphPad Prism® (GraphPad Software, San Diego, CA). As can be seen in FIG. 2 and accompanying table, the antibody bound well to the 2 melanoma cell lines and the NCI-H2052 lung cell line but much less to the NCI-H1975 cell line.

| EC50 (nM) | A2058 | A375 | NCI-H2052 | NCI-H1975 |
|---|---|---|---|---|
| ARD107 | 0.24 | 0.19 | 0.30 | — |

Example 3: Activity of ARD107-vcMMAE in an In Vitro Cytotoxicity Assay

The activity of ARD107 antibody conjugated to vcMMAE (ARD107-mc-vc-PAB-MMAE) was determined on seven human cancer cell lines (melanoma SkMel-31, Malme-3M, A2058, and A375), SW1353 chondrosarcoma, and the lung NCI-H2052 and NCI-H1975 cell lines. Each cell line was incubated with increasing concentrations of the ADCs (10-point dose curve) for 144 hrs. Cell viability was determined with CellTiter-Glo® (Promega).

Figure 3:
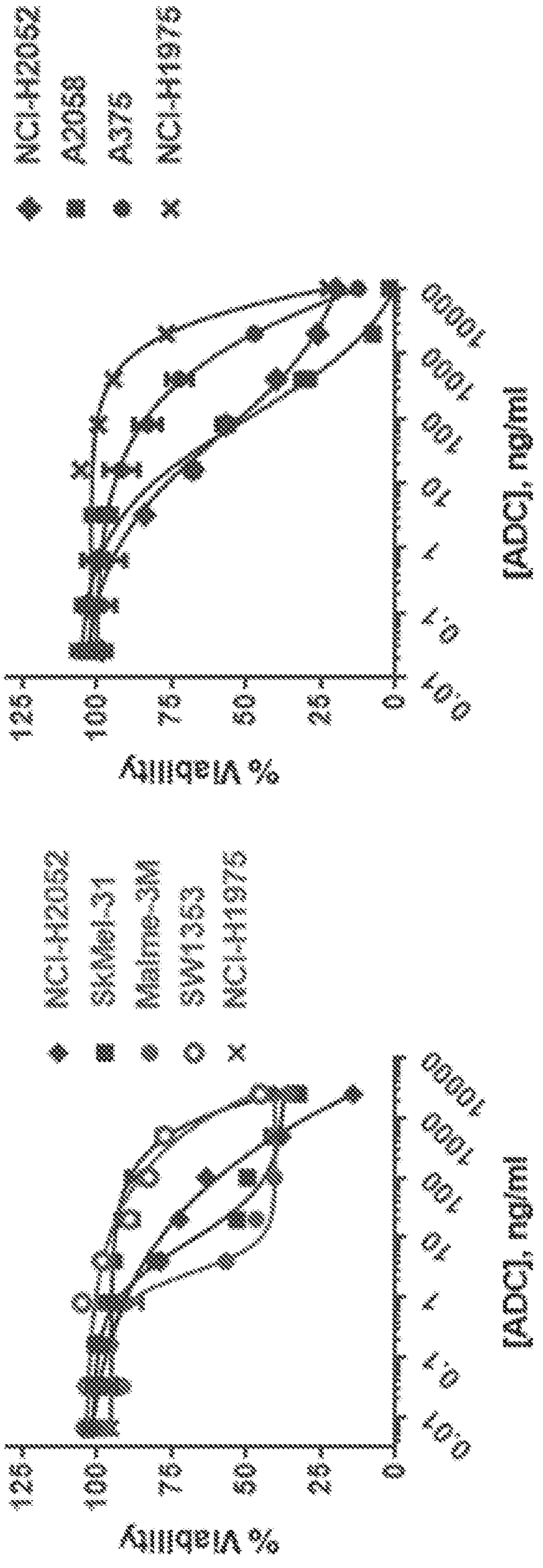
FIG. 3. Activity of ARD107-vcMMAE conjugate in an In vitro cytotoxicity assay.

The results of the in vitro testing of ARD107-vcMMAE in a cytotoxicity assay are shown in FIG. 3. ARD107-vcMMAE was active in inhibiting the cell growth of A2058 melanoma cells (IC50=105 ng/ml) and NCI-H2052 lung cancer cells (IC50=53 ng/ml). At higher concentrations, ARD107-vcMMAE inhibited the growth of A375 melanoma cells (IC50=575 ng/ml). The conjugate appeared to effective against a subpopulation of SkMel-31 and Malme-3M cells but the growth of 45% of the cells were not affected (plateaus at higher ADC doses). There was no activity against the SW1353 chondrosarcoma or NCI-H1975 lung cell line (IC50 >10,000). The IC50s are shown in the following table:

| Cell Line | A2058 | A375 | NCI-H2052 | SkMel-31 | Malme-3M | SW1353 | NCI-H1975 |
|---|---|---|---|---|---|---|---|
| Indication | Melanoma | Melanoma | Lung | Melanoma | Melanoma | Chondrosarcoma | Lung |
| IC50 (ng/ml) | 105 | 575 | 53 | Plateau | Plateau | >10000 | >10000 |

Example 4: The Antitumor Effect of ARD107-vcMMAE and ARD107-SN38 ADCs in the A2058 Melanoma Xenograft Model Mice were implanted with A2058 melanoma cells and treated with the ADCs when tumors achieved 150 $mm^3$. ADCs were given intravenously once every 4 days for 4 doses (arrows) or as indicated in the legend.

Figure 4:
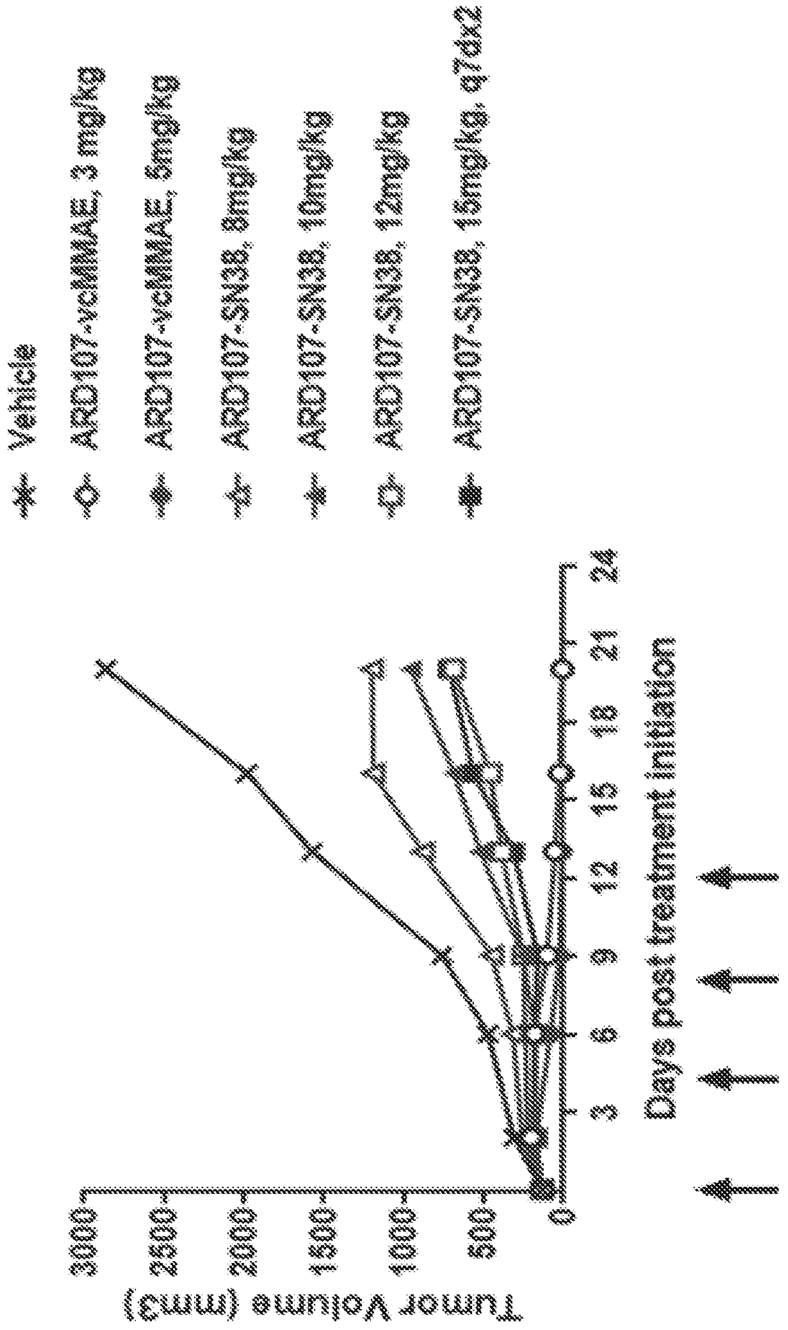
FIG. 4. The antitumor effect of ARD107-vcMMAE and ARD107-SN38 ADCs in the A2058 melanoma xenograft model.

The results of the in vivo testing of ARD107-vcMMAE and ARD107-SN38 ADCs in the A2058 melanoma xenograft model are shown in FIG. 4. Tumor-bearing mice were given ADCs intravenously once every 4 days (arrows) or as indicated in legend. ARD107-vcMMAE was highly effective in reducing tumor burden. Treatment of mice with this ADC yielded complete regressions in 100% of the mice (8/8 mice) when given at 5 mg/kg or in 6 of 8 mice when given at 3 mg/kg.

Example 5: The Antitumor Effect of ARD107-vcMMAE and ARD107-SN38 ADCs in the A375 Melanoma Xenograft Model Mice were implanted with A2058 melanoma cells and treated with the ADCs when tumors achieved 150 mm3. ARD107-SN38 was given intravenously once every 4 days for 6 doses (arrows). ARD107-vcMMAE was given intravenously once every 4 days for 4 doses.

Figure 5:
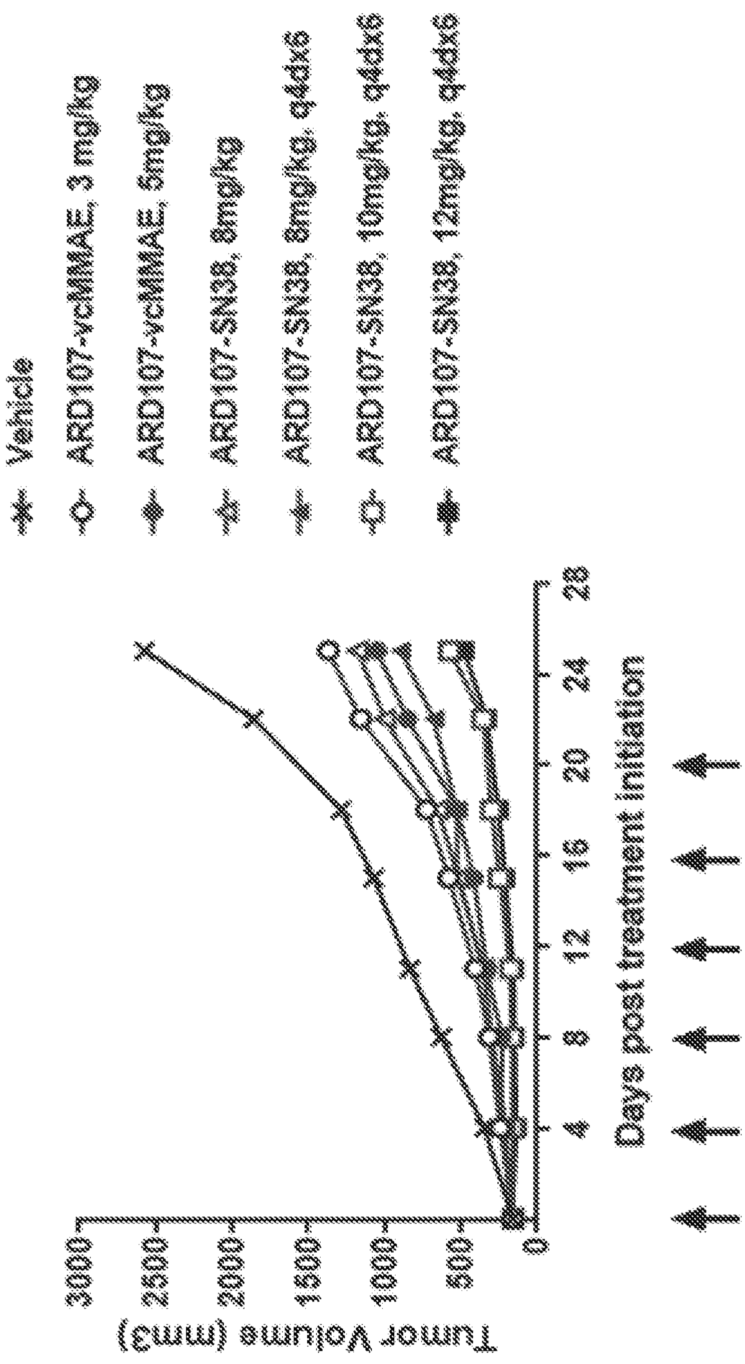
FIG. 5. The antitumor effect of ARD107-vcMMAE and ARD107-SN38 ADCs in the A375 melanoma xenograft model.

The results of the in vivo testing of ARD107-vcMMAE and ARD107-SN38 ADCs in the A375 melanoma xenograft model are shown in FIG. 5. Tumor-bearing mice was given ARD107-SN38 intravenously once every 4 days for 6 doses (arrows) or ARD107-vcMMAE once every 4 days for 4 doses. One group of mice was given 8 mg/kg ARD107-SN38 once every 4 days for 4 doses. ARD107-vcMMAE and ARD107-SN38 ADCs were effective in reducing tumor burden. Treatment of mice with ARD107-SN38 yielded 1 complete regression when given at 12 mg/kg.

Example 6: Preparation of ARD107-Gly-vcMMAE and ARD107-vcMMAE

The following provides examples of methods that may be used to prepare ARD107-Gly-vcMMAE and ARD107-vcMMAE ADCs. All reactions were carried out in oven dried glassware under a nitrogen atmosphere unless otherwise stated. Commercially available vcMMAE was purchased from MedChem Express. Dichloromethane (DCM), diisopropylethyl amine, dimethylformamide (DMF), 1-[Bis(dimethylamino)methylene]-1H-1,2,3-triazolo[4,5-b]pyridinium 3-oxide hexafluorophosphate (HATU), tetrahydrofuran (THF), Ethylenediaminetetraacetic acid (EDTA), tris(2-carboxyethyl) phosphine (TCEP), N-acetylcysteine (NAC), and dimethyl sulfoxide (DMSO) were purchased from Sigma-Aldrich, TCI, Fisher Scientific, and Sigma-Aldrich, respectively, and were used as is with no additional purification.

Reaction Scheme of ARD107-Gly-vcMMAE ADC via Cysteine residues

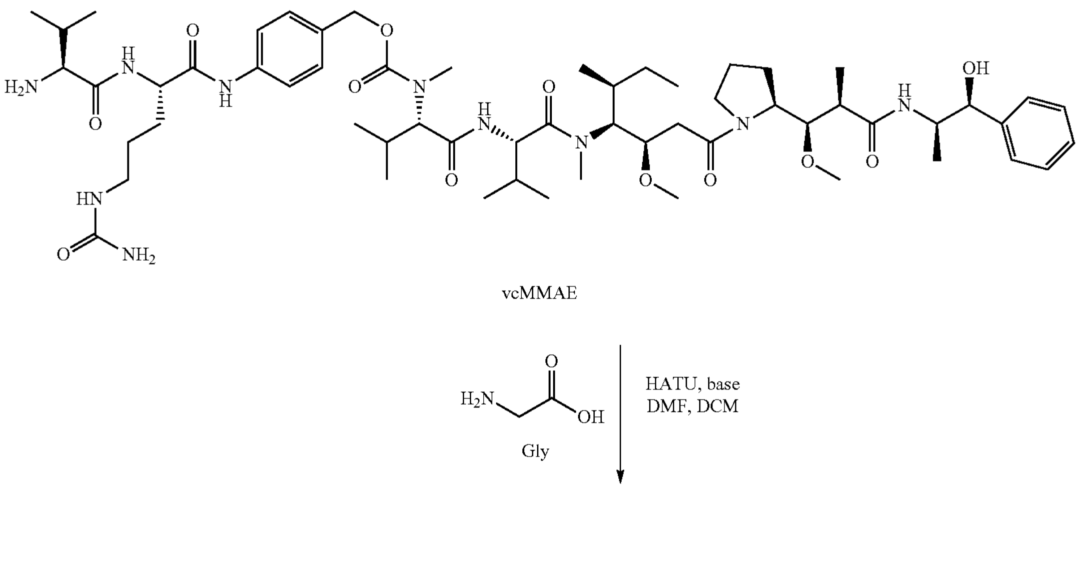

vcMMAE

Gly

-continued

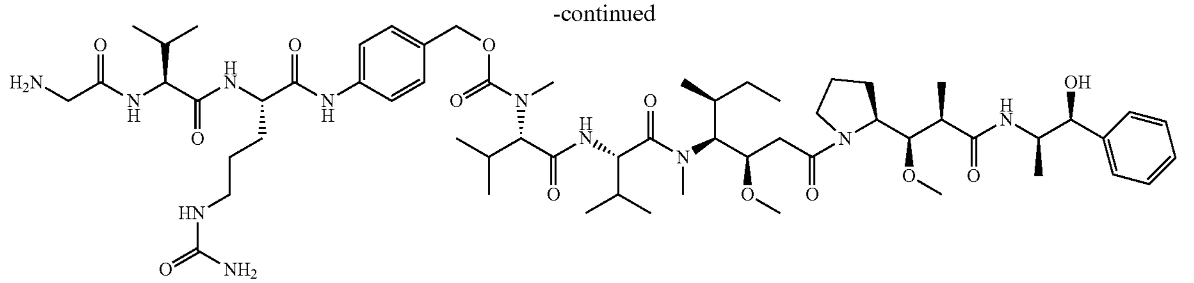

Gly-vcMMAE

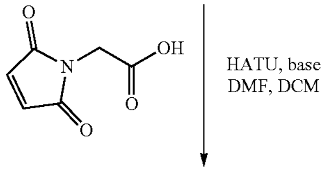

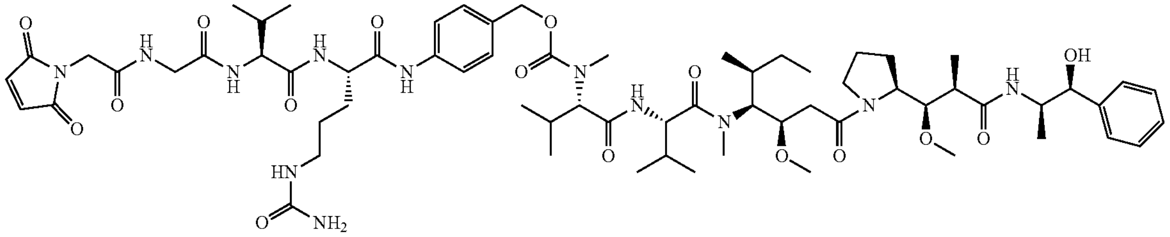

Maleimide-acetyl-Gly-vcMMAE

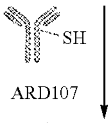

ARD107

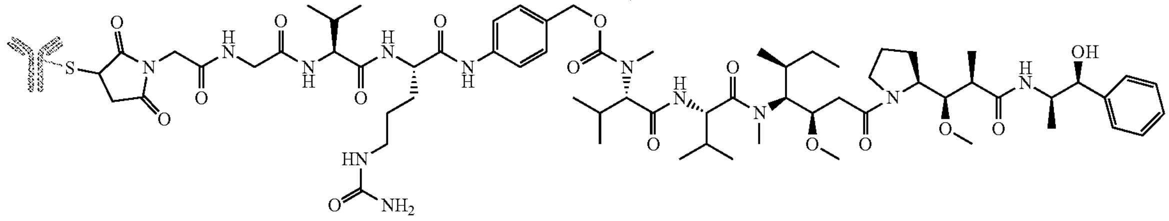

ARD107-Gly-vcMMAE ADC

Synthesis of Gly-vcMMAE

Into a round bottomed flask was placed vcMMAE (1.0 equiv), DMF and a magnetic stir bar. HATU coupling agent (1.2 equiv) was added and the mixture was stirred for 5 min before adding glycine (1.0 equiv) and diisopropylethylamine (3.0 equiv). After stirring overnight, TLC indicated the reaction was complete. The reaction mixture as concentrated on the rotovap and then partitioned between dichloromethane and water. The solvent layers were separated with an extraction funnel and the aqueous layer extracted three additional times with dichloromethane. The organic layers were combined, dried over sodium sulfate and concentrated under reduced pressure. The product was purified by column chromatography to afford a pure acetyl-Gly-vcMMAE.

Synthesis of Maleimide acetyl-Gly-vcMMAE

To a stirring solution of 2-(2,5-Dioxo-2,5-dihydro-1H-pyrrol-1-yl)acetic acid (1.0 equiv) in DCM and DMF, HATU (1.0 equiv) was added followed by diisopropylethylamine (3.0 equiv). The reaction was allowed to stir for 5 minutes before Gly-vcMMAE was added as a solution in DCM and DMF. The reaction was allowed to stir at room temperature for 6 hours before being quenched through the addition of water. The reaction mixture as concentrated on the rotovap and purified by column chromatography to afford a pure Maleimide acetyl-Gly-vcMMAE.

Synthesis of ARD107-Gly-vcMMAE ADC Via Cysteine Residues

Antibody drug conjugate (ADC) that is enriched for 4-load species is created by controlling the degree of native disulfide bond reduction and the subsequent conjugation of the linker-payload onto the reduced disulfides. Cysteine conjugation relies on a chemical reaction between the cysteine thiol group of an antibody and the maleimide group of Maleimide-acetyl-Gly-vcMMAE in the linker. Maleimide-acetyl-Gly-vcMMAE was conjugated to antibody ARD107 by Michael addition to form ARD107-Gly-vcMMAE (ARD107-maleimide acetyl-Gly-Val-Cit-PAB-MMAE) ADC. A conjugation buffer solution contained sodium phosphate, sodium chloride and Ethylenediaminetetraacetic acid (EDTA) was prepared. The ARD107 stock solution was diluted with the conjugation buffer. The disulfide bridges were then reduced with tris(2-carboxyethyl) phosphine (TCEP) with precise control of the reduction reaction temperature, pH, time of reduction, and the molar ratio of TCEP and ARD107 to afford available sulfhydryl groups on the ARD107 molecule. The reduced ARD107 was then conjugated with maleimide-acetyl-Gly-vcMMAE dissolved in DMSO with precise control of the reaction temperature, pH, time of conjugation and the molar ratio of maleimide-acetyl- Gly-vcMMAE and ARD107 to afford DAR4. The reactions were stirred overnight. Upon completion of the reaction, N-acetylcysteine (NAC) or cysteine was employed to quench the reaction, and the unreacted maleimide-acetyl-Gly-vcMMAE and side products were removed by ultrafiltration to afford a pure ARD107-Gly-vcMMAE (ARD107-maleimide acetyl-Gly-Val-Cit-PAB-MMAE) ADC. The reduction and conjugation reaction conditions are designed to enhance the yield of DAR4 species and to minimize the yield of higher loaded forms such as DAR6 and DAR8.

Reaction Scheme of ARD107-vcMMAE ADC via Cysteine residues

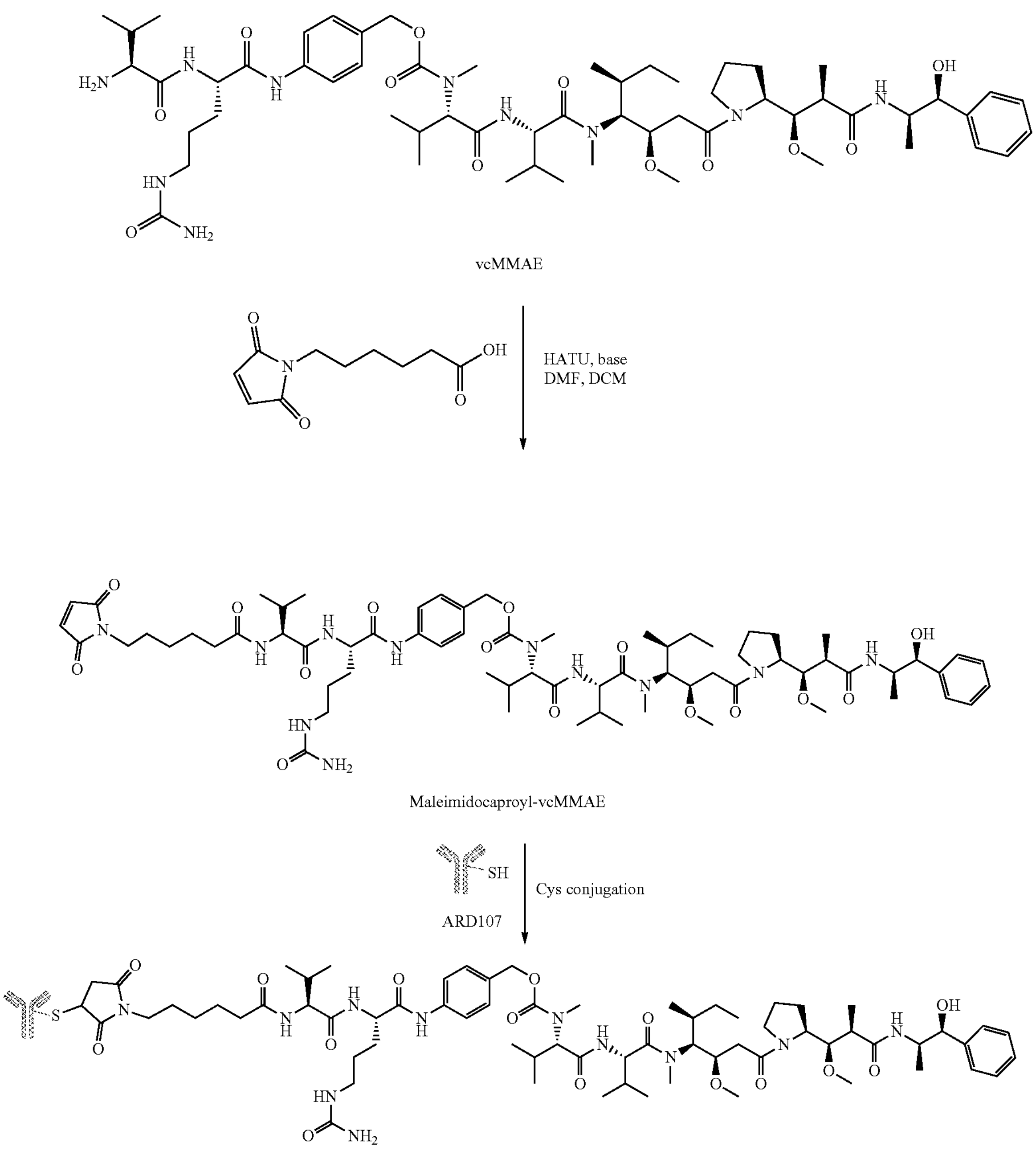

vcMMAE

Maleimidocaproyl-vcMMAE

ARD107-vcMMAE ADC

Synthesis of Maleimidocaproyl-vcMMAE

To a stirring solution of 2-(2,5-Dioxo-2,5-dihydro-1H-pyrrol-1-yl)acetic acid (1.0 equiv) in DCM and DMF, HATU (1.0 equiv) was added followed by diisopropylethylamine (3.0 equiv). The reaction was allowed to stir for 5 minutes before vcMMAE was added as a solution in DCM and DMF. The reaction was allowed to stir at room temperature for 6 hours before being quenched through the addition of water. The reaction mixture as concentrated on the rotovap and purified by column chromatography to afford a pure maleimidocaproyl-vcMMAE (mc-vcMMAE).

Synthesis of ARD107-vcMMAE ADC Via Cysteine Residues

ARD107-vcMMAE ADC was prepared from a conjugation of ARD107 with mc-vcMMAE. A conjugation buffer solution contained sodium phosphate, sodium chloride and Ethylenediaminetetraacetic acid (EDTA) was prepared. The ARD107 stock solution was diluted with the conjugation buffer. The disulfide bridges were then reduced with tris(2-carboxyethyl) phosphine (TCEP) with precise control of the reduction reaction temperature, pH, time of reduction, and the molar ratio of TCEP and ARD107 to afford available sulfhydryl groups on the ARD107 molecule. The reduced ARD107 was then conjugated with mc-vcMMAE dissolved in DMSO with precise control of the reaction temperature, pH, time of conjugation and the molar ratio of mc-vcMMAE and ARD107 to afford DAR4. The reactions were stirred overnight. Upon completion of the reaction, N-acetylcysteine (NAC) or cysteine was employed to quench the reaction, and the unreacted mc-vcMMAE and side products were removed by ultrafiltration to afford a pure ARD107-vcMMAE (ARD107-mc-vc-PAB-MMAE) ADC. The reduction and conjugation reaction conditions are designed to enhance the yield of DAR4 species and to minimize the yield of higher loaded forms such as DAR6 and DAR8. ARD107-vcMMAE [DAR4] was prepared according to the above procedure.

Reaction Scheme of ARD107-Gly-vcMMAE ADC via Lysine residues

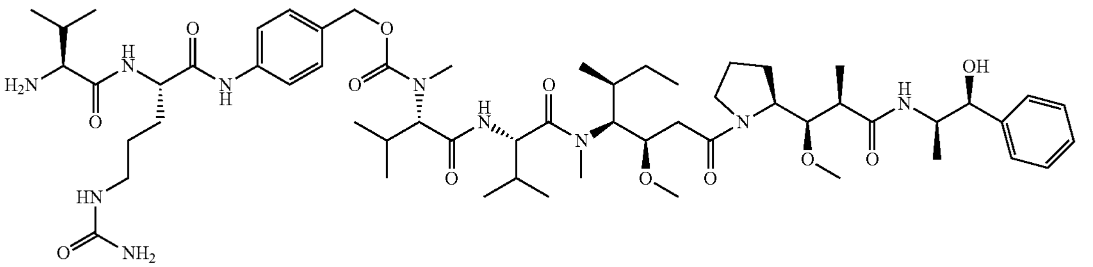

vcMMAE

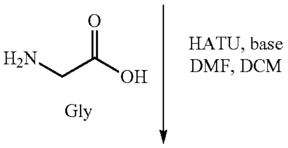

Gly

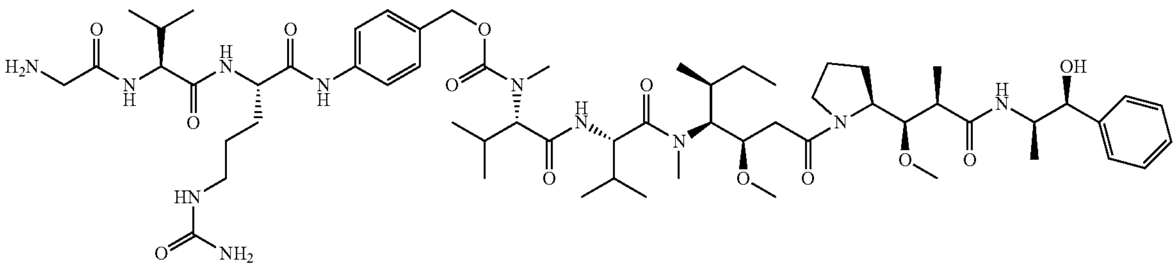

Gly-vcMMAE

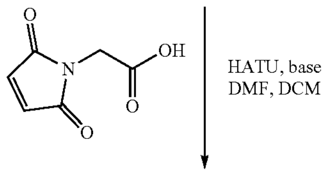

-continued

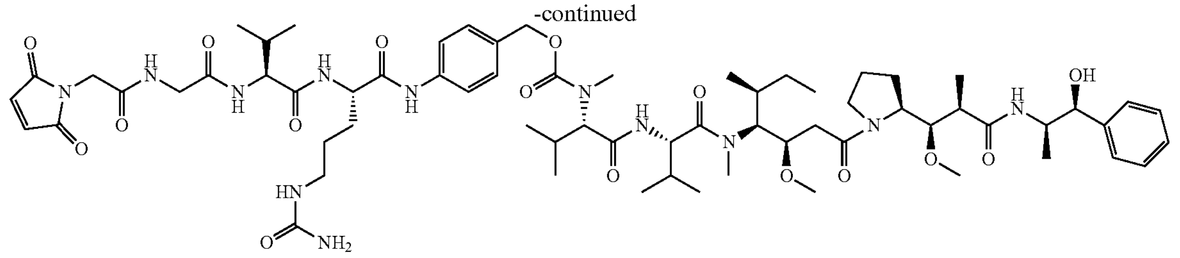

Maleimide-acetyl-Gly-vcMMAE

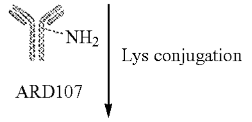

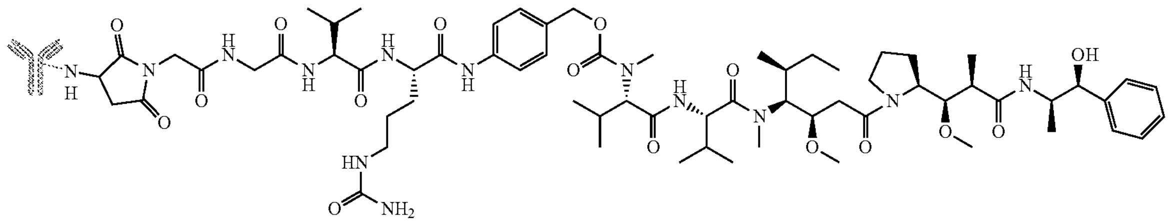

ARD107-Gly-vcMMAE ADC

Synthesis of ARD107-Gly-vcMMAE ADC Via Lysine Residues

In some embodiments, ADC can also be enriched for 4-load species by performing a stochastic conjugation (lysine based conjugation) shown in the above reaction scheme followed by selective enrichment for the 4-load species by separating the 4-load species away from the lower and higher-loaded species using a hydrophobic interaction chromatography column (HIC). Unpurified ARD107-Gly-vcMMAE ADC was purified by HIC column (0.8×10 cm, 5 mL) prepacked by HIC resin to afford the 4-load enriched species. All process was performed at room temperature. Before sample injection, the column was equilibrated with 3 column volumes of buffer A (50 mM sodium phosphate pH 7.0 and 2 M sodium chloride (NaCl)). For loading onto the column, 2.5 mL of unpurified ARD107-Gly-vcMMAE ADC was mixed with 2.5 mL of buffer A. This resulting mixture (total 5 mL) was injected into the column and eluted using a linear gradient from 100% buffer to 100% buffer B (50 mM sodium phosphate pH 7.0, 20% isopropyl alcohol (IPA) v/v).

Reaction Scheme of ARD107-vcMMAE ADC via Lysine residues

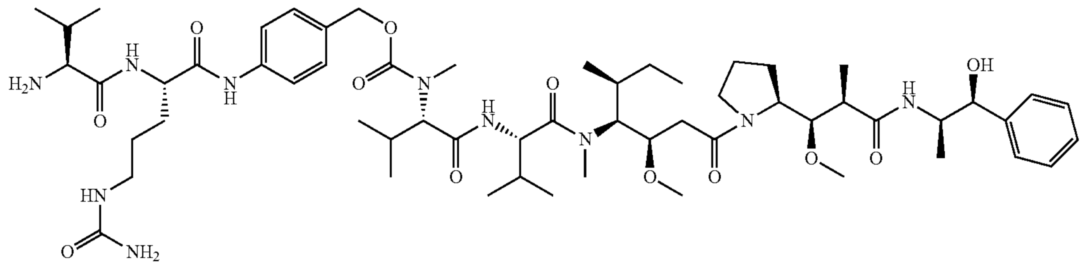

vcMMAE

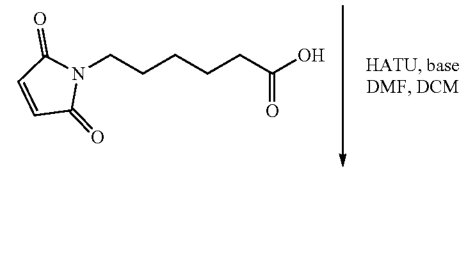

-continued

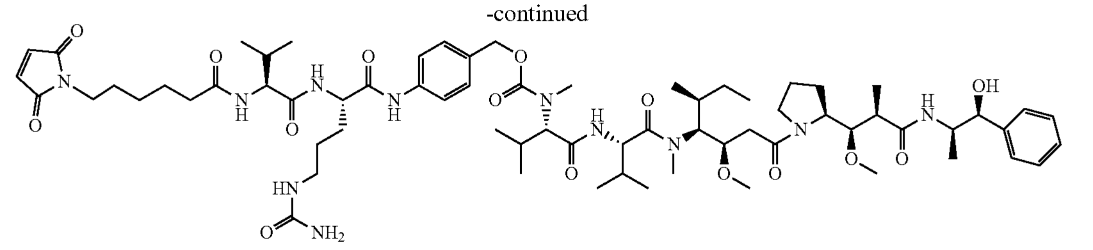

Maleimidocaproyl-vcMMAE

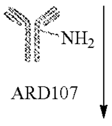

ARD107

Lys conjugation

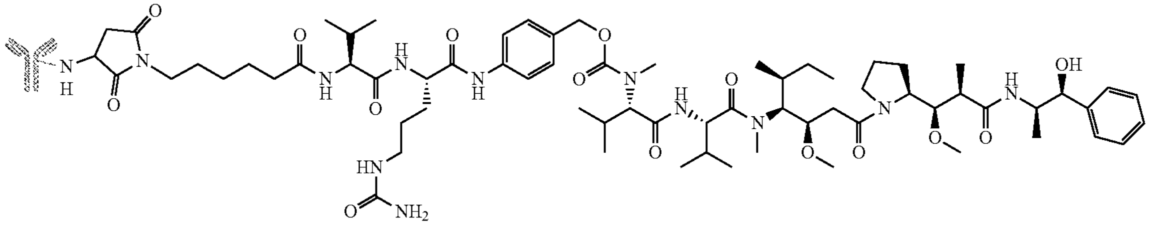

ARD107-vcMMAE ADC

Synthesis of ARD107-vcMMAE ADC Via Lysine Residues

In some embodiments, ADC can also be enriched for 4-load species by performing a stochastic conjugation (lysine based conjugation) shown in the above reaction scheme followed by selective enrichment for the 4-load species by separating the 4-load species away from the lower and higher-loaded species using a hydrophobic interaction chromatography column (HIC). Unpurified ARD107-vcMMAE ADC was purified by HIC column (0.8×10 cm, 5 mL) prepacked by HIC resin to afford the 4-load enriched species. All process was performed at room temperature. Before sample injection, the column was equilibrated with 3 column volumes of buffer A (50 mM sodium phosphate pH 7.0 and 2 M sodium chloride (NaCl)). For loading onto the column, 2.5 mL of unpurified ARD107-vcMMAE ADC was mixed with 2.5 mL of buffer A. This resulting mixture (total 5 mL) was injected into the column and eluted using a linear gradient from 100% buffer to 100% buffer B (50 mM sodium phosphate pH 7.0, 20% isopropyl alcohol (IPA) v/v). ARD107-vcMMAE and ARD107-vcMMAE [HIC] were prepared according to the above procedure.

Example 7: Binding of Different Preparations of ARD107-MMAE to CSPG4 Protein

ARD107-vcMMAE ADCs prepared by stochastic conjugation, enrichment for 4-load, and by column purification of the 4-loaded species and ARD107 antibody conjugated to Gly-vcMMAE linker were tested for binding to recombinant human CSPG4 protein by ELISA. As shown in FIG. 6, all tested ADC preparations exhibited binding to target CSPG4 similar to the unconjugated ARD107 monoclonal antibody.

Figure 7:
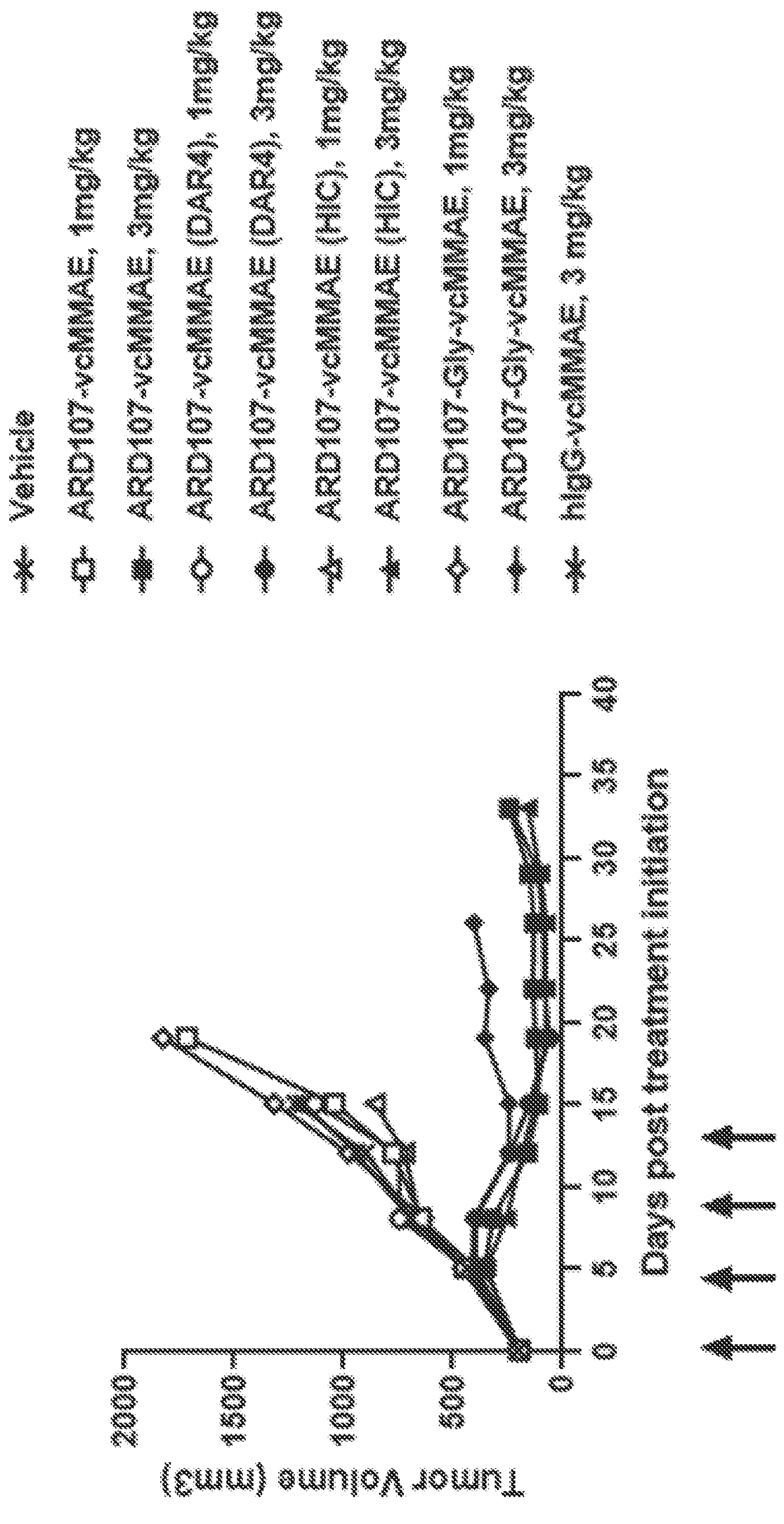
FIG. 7. The antitumor effects of different preparations of ARD107-vcMMAE (stochastic conjugation, enriching for 4-load, HIC column purification for 4-load, and maleimide-acetyl-Gly-vc-PAB-MMAE linker [Gly-vcMMAE] in the A2058 melanoma xenograft model.

Example 8: The Antitumor Effect of Different Preparations of ARD107-vcMMAE and ARD107-Gly-vcMMAE ADCs in the A2058 Melanoma Xenograft Model Mice were implanted with A2058 melanoma cells and treated with the ADCs when tumors achieved 200 mm3. ADCs described in Example 6 were given intravenously once every 4 days for 4 doses (arrows in FIG. 7). ARD107-vcMMAE was given intravenously once every 4 days for 4 doses. The results of the in vivo testing of ARD107-vcMMAE prepared by standard stochastic conjugation methods (ARD107-vcMMAE), enriched for 4-load (ARD107-vcMMAE (DAR4)), or column purified for the 4-loaded species (ARD107-vcMMAE (HIC)) and ARD107-Gly-vcMMAE ADCs in the AA2058 melanoma xenograft model are shown in FIG. 7. The ADC prepared by standard stochastic conjugation methods (ARD107-vcMMAE), enriched for 4-load (ARD107-vcMMAE (DAR4)), or column purified for the 4-loaded species (ARD107-vcMMAE (HIC)) all significantly reduced tumor burden ($p<0.025$ to Vehicle). The ARD107-Gly-vcMMAE treatment also reduced tumor burden compared to Vehicle ($p<0.05$) but was less effective compared to the other ADC preparations. Treatment of mice with 3 mg/kg ADC yielded complete regressions in some mice (2/8 mice in ARD107-vcMMAE (HIC) and 1/8 mice in the stochastic group).

Example 9: Humanized Variants of ARD107 and Characterization

Computational modeling was used for humanization design. ARD107 Fv homology model was built up by using Protein Data Bank (pdb) 3CFD as model structure and design was double checked with another model built up on other structures, 1FNS and 1NDM. Alignment with the closest gene and allele from the IMGT V domain directory (*Homo sapien*) was performed for human VH and VL framework acceptor (IGHV4-31*02 for VH and IGKV1-39*01 for VL). During the humanization process, mouse CDRs were grafted into the human framework acceptor, residues in human framework which are different from those in murine framework were evaluated. There are 6 backmutations in VHv1, 7 in VHv2, 8 in VHv3 and 9 in VHv4. There are 6 backmutations in VLv1, 7 in VLv2, 7 in VLv3 and 9 in VLv4.

Heavy chain variable region sequences were cloned into a vector containing a signal peptide sequence and human IgG1 constant region, while variable light chain regions were cloned into a vector containing a signal peptide sequence and human kappa light chain region. Heavy chain and light chain were paired to generate monoclonal antibodies as provided in Table 1 for further characterization.

Figure 8A:
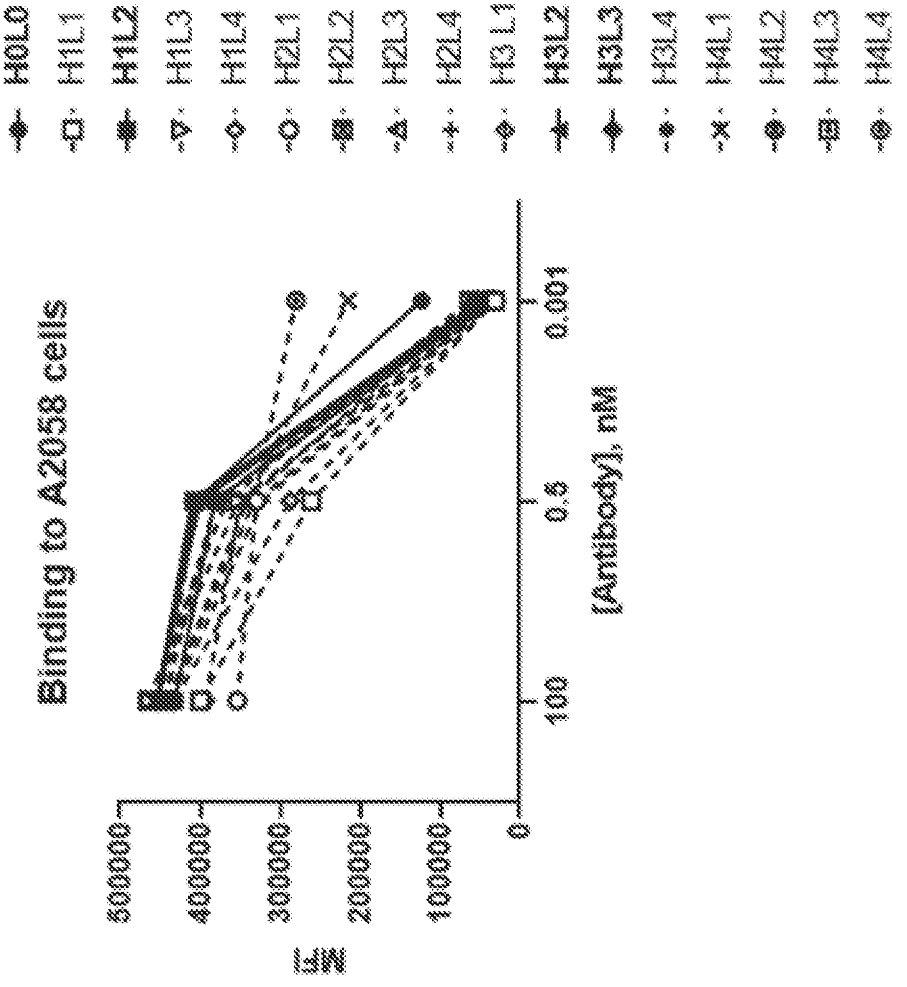
FIGS. 8A-8B. Characterization of 16 humanized candidates of ARD107 antibody by (FIG. 8A) binding to A2058 cells and (FIG. 8B) binding to A2058 cells after heat treatment.
Figure 8B:
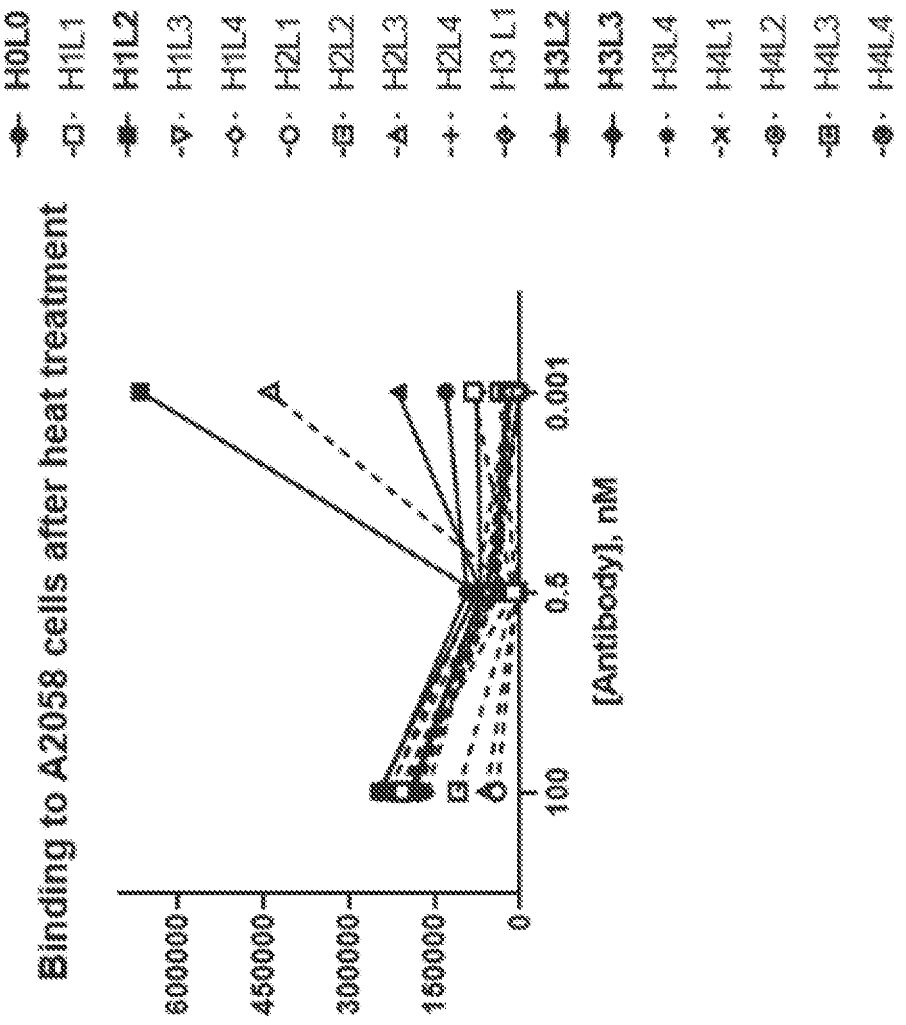

A primary screen was conducted to evaluate sixteen combinations of VH and VL (see, Table 1) for binding to the CSPG4+A2058 melanoma cell line (FIG. 8A). This binding affinity was compared to binding measured after a 5-minute heat treatment (thermostability) (FIG. 8B). Based upon these results and assessment of protein production, lead candidates were selected for further round of testing that included binding and internalization studies (H1L2, H3L2, and H3L3).

TABLE 1

ARD107 Humanized Antibodies

| Antibody Description | Heavy Chain Polypeptide | Light Chain Polypeptide |
|---|---|---|
| H0L0 (ARD107 chimeric antibody) | SEQ ID NO: 7 | SEQ ID NO: 8 |
| H1L1 | SEQ ID NO: 33 | SEQ ID NO: 37 |
| H1L2 | SEQ ID NO: 33 | SEQ ID NO: 38 |
| H1L3 | SEQ ID NO: 33 | SEQ ID NO: 39 |
| H1L4 | SEQ ID NO: 33 | SEQ ID NO: 40 |
| H2L1 | SEQ ID NO: 34 | SEQ ID NO: 37 |
| H2L2 | SEQ ID NO: 34 | SEQ ID NO: 38 |
| H2L3 | SEQ ID NO: 34 | SEQ ID NO: 39 |
| H2L4 | SEQ ID NO: 34 | SEQ ID NO: 40 |
| H3L1 | SEQ ID NO: 35 | SEQ ID NO: 37 |
| H3L2 | SEQ ID NO: 35 | SEQ ID NO: 38 |
| H3L3 | SEQ ID NO: 35 | SEQ ID NO: 39 |
| H3L4 | SEQ ID NO: 35 | SEQ ID NO: 40 |
| H4L1 | SEQ ID NO: 36 | SEQ ID NO: 37 |
| H4L2 | SEQ ID NO: 36 | SEQ ID NO: 38 |
| H4L3 | SEQ ID NO: 36 | SEQ ID NO: 39 |
| H4L4 | SEQ ID NO: 36 | SEQ ID NO: 40 |

Figure 9A:
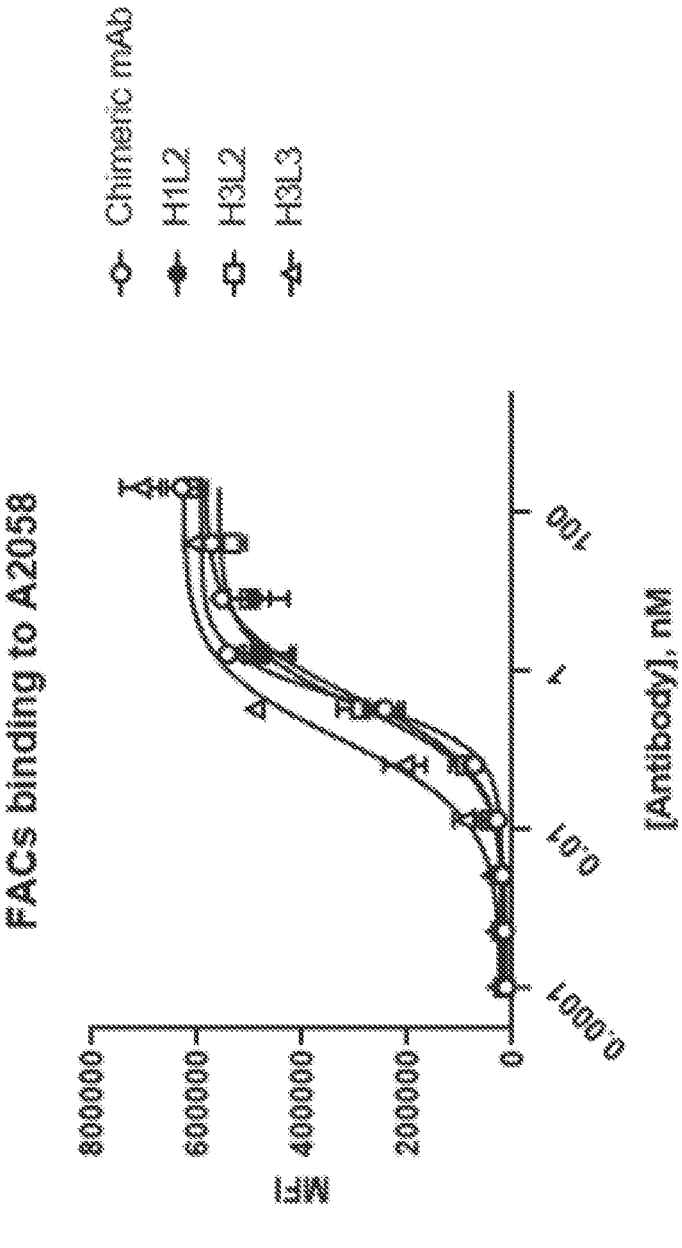
FIGS. 9A-9B. Characterization of the 3 humanized leads of ARD107 antibody in comparison to the chimeric antibody by (FIG. 9A) binding to A2058 cells and (FIG. 9B) binding to A2058 cells after heat treatment.
Figure 9B:
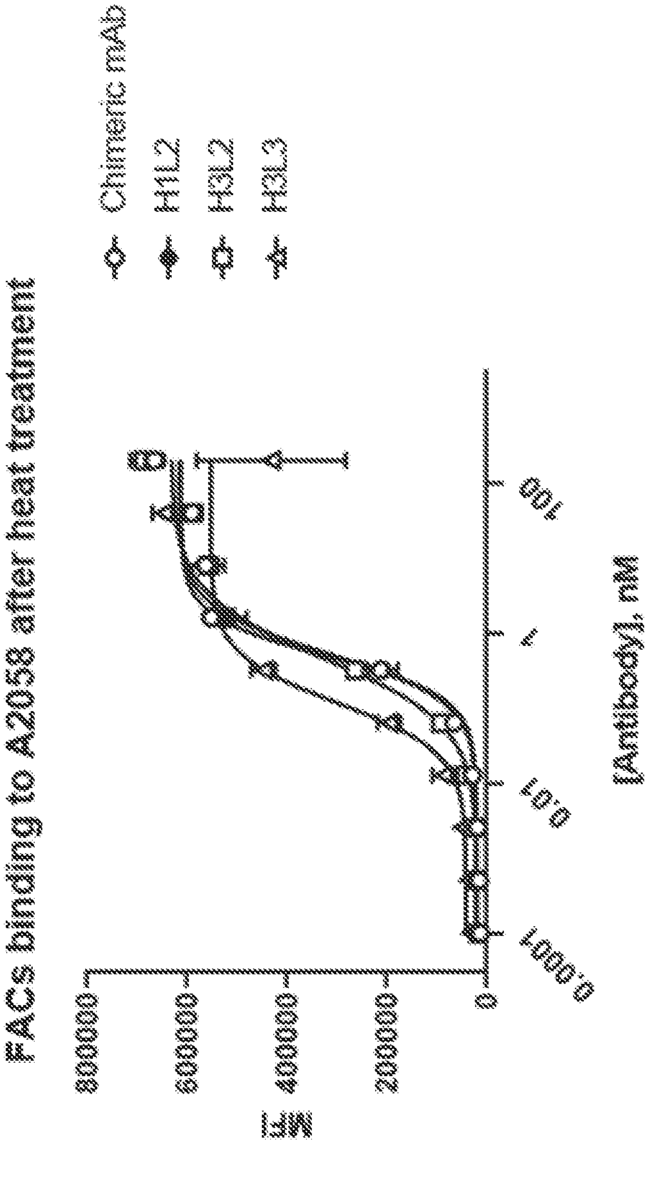

Lead humanized variants of ARD107 antibody (H1L2, H3L2, and H3L3) were analyzed for binding to CSPG4+ A2058 melanoma cells (FIG. 9A) and internalization by A2058 melanoma cells (FIG. 9B). For assessing antibody binding by ELISA, Nunc Immuno Maxisorp 96-well plates (ThermoFisher) were coated overnight with recombinant human CSPG4 protein (R&D Systems). The plates were then washed, blocked and incubated with the test agents (mAbs or ADCs) for 2 hours. Detection of bound test agent was determined upon subsequent incubation with a goat anti-human Fc-specific secondary antibody (Sigma) and TMB substrate. All 3 humanized variants bound to the target cells similarly to the chimeric antibody, with the H3L3 variant showing slightly better binding.

Figure 10:
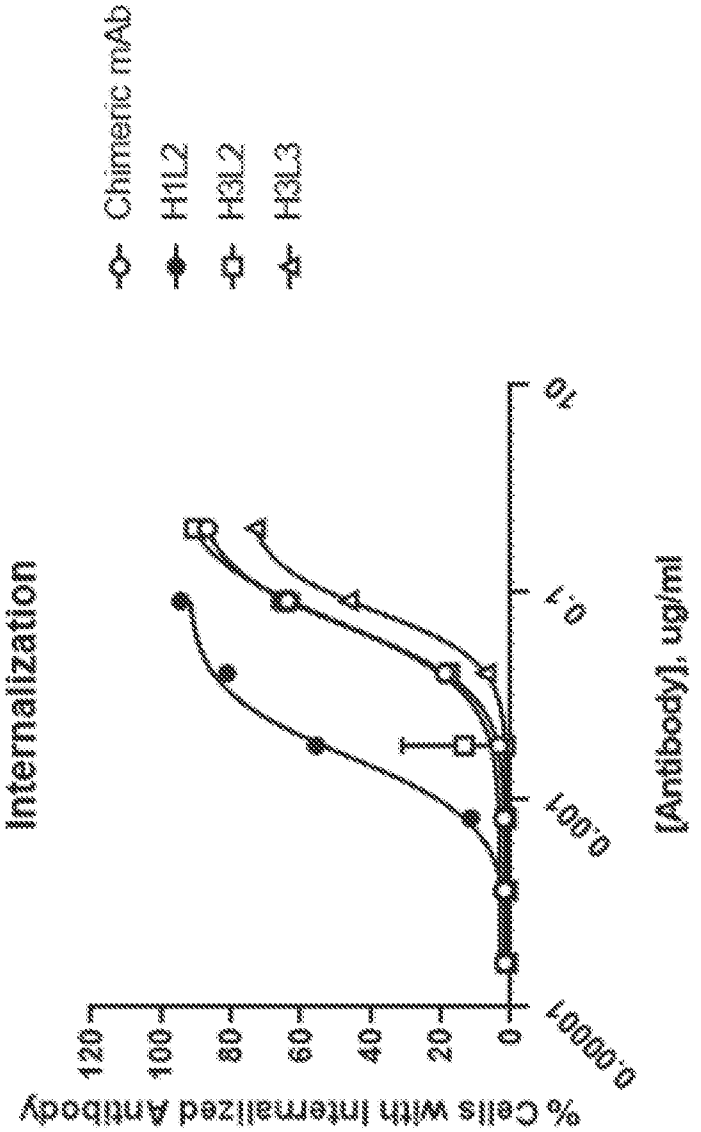
FIG. 10. Characterization of the 3 humanized leads of ARD107 antibody in comparison to the chimeric antibody by internalization in A2058 melanoma cells.

The internalization of humanized ARD107 antibodies (H1L2, H3L2, and H3L3) was conducted using the Zenon pHrodo reagents as per manufacturer's directions (ThermoFisher). Briefly, A2058 melanoma cells were plated in tissue culture media at 100,000 cells per well in 96-well tissue culture plates. The cells were pre-incubated with the antibodies prior to an overnight incubation with the pHrodo-labeled secondary antibody. The next day, the cells were harvested and analyzed by flow cytometry. Internalization was determined as the fraction of live cells that stained positive for pHrodo-RED. Data was graphed with GraphPad Prism® (GraphPad, La Jolla, CA). All of the humanized antibodies were internalized by the target cells (FIG. 10). The H1L2 variant showed better internalization when compared to the chimeric antibody or the other 2 variants.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet, including U.S. Patent Application No. 63/093,255, filed on Oct. 18, 2020, are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A binding agent comprising:

(a) a heavy chain variable (VH) region having the amino acid sequence set forth in SEQ ID NO:25, and a light chain variable (VL) region having the amino acid sequence set forth in SEQ ID NO:30;

(b) a heavy chain variable (VH) region having the amino acid sequence set forth in SEQ ID NO:27, and a light chain variable (VL) region having the amino acid sequence set forth in SEQ ID NO:30; or (c) a heavy chain variable (VH) region having the amino acid sequence set forth in SEQ ID NO:27, and a light chain variable (VL) region having the amino acid sequence set forth in SEQ ID NO:31;

wherein the binding agent specifically binds to human CSPG4.

2. The binding agent of claim 1, wherein the binding agent is an antibody or an antigen-binding portion thereof.

3. The binding agent of claim 2, wherein the binding agent is a monoclonal antibody, a Fab, a Fab', an F(ab'), an Fv, a disulfide-linked Fc, a scFv, a single-domain antibody, a diabody, a bispecific antibody, or a multispecific antibody.

4. The binding agent of claim 1, wherein the heavy chain variable region further comprises a heavy chain constant region and the light chain variable region further comprises a light chain constant region.

5. The binding agent of claim 4, wherein:

(a) the heavy chain constant region is of the human IgG isotype;

(b) the heavy chain constant region is an IgG1 constant region;

(c) a IgG1 heavy chain constant region has the amino acid sequence set forth in positions 113-442 of SEQ ID NO:3;

(d) the heavy chain constant region is an IgG4 constant region; or (e) the heavy chain variable and constant regions have the amino acid sequence set forth in SEQ ID NO: 33 or 35.

6. The binding agent of claim 4, wherein:

(a) the light chain constant region is of the kappa isotype;

(b) a kappa light chain constant region has the amino acid sequence set forth in positions 108-214 of SEQ ID NO:4; or (c) the light chain variable and constant regions have the amino acid sequence set forth in SEQ ID NO:38 or 39.

7. The binding agent of claim 1, wherein:

(a) the heavy chain variable and constant regions have the amino acid sequence set forth SEQ ID NO:33, and the light chain variable and constant regions have the amino acid sequence set forth in SEQ ID NO:38;

(b) the heavy chain variable and constant regions have the amino acid sequence set forth SEQ ID NO:35, and the light chain variable and constant regions have the amino acid sequence set forth in SEQ ID NO:38; or (c) the heavy chain variable and constant regions have the amino acid sequence set forth SEQ ID NO:35, and the light chain variable and constant regions have the amino acid sequence set forth in SEQ ID NO:39.

8. A pharmaceutical composition comprising the binding agent of claim 1 and a pharmaceutically acceptable carrier.

9. A nucleic acid encoding the binding agent of claim 1.

10. A vector comprising the nucleic acid of claim 9.

11. A cell line comprising the nucleic acid of claim 9.

12. A conjugate comprising:

(a) a binding agent comprising:

(i) a heavy chain variable region having the amino acid sequence set forth in SEQ ID NO:25, and a light chain variable region having the amino acid sequence set forth in SEQ ID NO:30;

(ii) a heavy chain variable region having the amino acid sequence set forth in SEQ ID NO:27, and a light chain variable region having the amino acid sequence set forth in SEQ ID NO:30; or (iii) a heavy chain variable region having the amino acid sequence set forth in SEQ ID NO:27, and a light chain variable region having the amino acid sequence set forth in SEQ ID NO:31;

wherein the binding agent specifically binds to human CSPG4;

(b) at least one linker attached to the binding agent; and (c) at least one cytotoxic agent attached to each linker.

13. The conjugate of claim 12, wherein the binding agent is an antibody or an antigen-binding portion thereof.

14. The conjugate of claim 13, wherein the binding agent is a monoclonal antibody, a Fab, a Fab', an F(ab'), an Fv, a disulfide-linked Fc, a scFv, a single-domain antibody, a diabody, a bi-specific antibody, or a multi-specific antibody.

15. The conjugate of claim 12, wherein the heavy chain variable region further comprises a heavy chain constant region and the light chain variable region further comprises a light chain constant region.

16. The conjugate of claim 15, wherein:

(a) the heavy chain constant region is of the human IgG isotype;

(b) the heavy chain constant region is an IgG1 constant region;

(c) a IgG1 heavy chain constant region has the amino acid sequence set forth in positions 113-442 of SEQ ID NO:3;

(d) the heavy chain constant region is an IgG4 constant region; or (e) the heavy chain variable and constant regions have the amino acid sequence set forth in SEQ ID NO: 33 or 35.

17. The conjugate of claim 15, wherein:

(a) the light chain constant region is of the kappa isotype;

(b) a kappa light chain constant region has the amino acid sequence set forth in positions 108-214 of SEQ ID NO:4; or (c) the light chain variable and constant regions have the amino acid sequence set forth in SEQ ID NO:38 or 39.

18. The conjugate of claim 12, wherein:

(a) the heavy chain variable and constant regions have the amino acid sequence set forth SEQ ID NO:33, and the light chain variable and constant regions have the amino acid sequence set forth in SEQ ID NO:38;

(b) the heavy chain variable and constant regions have the amino acid sequence set forth SEQ ID NO:35, and the light chain variable and constant regions have the amino acid sequence set forth in SEQ ID NO:38; or (c) the heavy chain variable and constant regions have the amino acid sequence set forth SEQ ID NO:35, and the light chain variable and constant regions have the amino acid sequence set forth in SEQ ID NO:39.

19. The conjugate of claim 12, wherein the linker is attached to the binding agent via an interchain disulfide residue, an engineered cysteine, a glycan or modified glycan, an N-terminal residue of the binding agent or a polyhistidine residue attached to the binding agent.

20. The conjugate of claim 12, wherein the average drug loading of the conjugate is from about 1 to about 8, about 2, about 4, about 6, about 8, about 10, about 12, about 14, about 16, about 3 to about 5, about 6 to about 8 or about 8 to about 16.

21. The conjugate of claim 12, wherein the binding agent is monospecific, bivalent, or bispecific.

22. The conjugate of claim 12, wherein the cytotoxic agent is selected from the group consisting of an auristatin, a camptothecin and a calicheamicin.

23. The conjugate of claim 22, wherein the cytotoxic agent is monomethyl auristatin E (MMAE), exatecan, or SN-38.

24. The conjugate of claim 12, wherein the linker is selected from the group consisting of mc-VC-PAB, CL2, CL2A, maleimide acetyl-Gly-Val-Cit-PAB, and (Succinimid-3-yl-N)—$(CH_2)_n{}^2$—C(═O)-Gly-Gly-Phe-Gly-NH—$CH_2$═$OCH_2$—(C═O)—.

25. The conjugate of claim 24, wherein:

(a) the linker is mc-VC-PAB and is attached to at least one molecule of MMAE;

(b) the linker is CL2A and is attached to at least one molecule of SN-38;

(c) the linker is CL2 and is attached to at least one molecule of SN-38; or (d) the linker is (Succinimid-3-yl-N)—$(CH_2)_n{}^2$—C(═O)-Gly-Gly-Phe-Gly-NH—$CH_2$═$OCH_2$—(C═O)— and is attached to at least one molecule of exatecan.

26. A pharmaceutical composition comprising the conjugate of claim 12 and a pharmaceutically acceptable carrier.

27. A method of treating a CSPG4+ cancer, comprising administering to a subject in need thereof a therapeutically effective amount of the pharmaceutical composition of claim 8.

28. The method of claim 27, wherein the CSPG4+ cancer is selected from melanoma, head and neck cancer, breast cancer, mesothelioma, renal clear cell cancer, chondrosarcoma, urothelial cancer, osteosarcoma, pancreatic cancer, thyroid cancer, and leukemia (B-ALL).

29. The method of claim 27, further comprising administering an immunotherapy or chemotherapy to the subject.

30. The method of claim 29, wherein the immunotherapy comprises an immune checkpoint inhibitor.

31. The method of claim 30, wherein the immune checkpoint inhibitor is selected from an antibody that specifically binds to human PD-1, human PD-L1, or human CTLA4.

32. The method of claim 31, wherein the immune checkpoint inhibitor is pembrolizumab, nivolumab, cemiplimab or ipilimumab.

33. The method of claim 27, wherein the binding agent is administered intravenously.

34. The method of claim 27, wherein the binding agent is administered in a dose of about 0.1 mg/kg to about 10 mg/kg or from about 0.1 mg/kg to about 12 mg/kg.

35. A method of treating a CSPG4+ cancer, comprising administering to a subject in need thereof a therapeutically effective amount of the pharmaceutical composition of claim 26.

36. The method of claim 35, wherein the CSPG4+ cancer is selected from melanoma, head and neck cancer, breast cancer, mesothelioma, renal clear cell cancer, chondrosarcoma, urothelial cancer, osteosarcoma, pancreatic cancer, thyroid cancer, and leukemia (B-ALL).

37. The method of claim 35, further comprising administering an immunotherapy or chemotherapy to the subject.

38. The method of claim 37, wherein the immunotherapy comprises an immune checkpoint inhibitor.

39. The method of claim 38, wherein the immune checkpoint inhibitor is selected from an antibody that specifically binds to human PD-1, human PD-L1, or human CTLA4.

40. The method of claim 35, wherein the conjugate is administered intravenously.

41. The method of claim 35, wherein the conjugate is administered in a dose of about 0.1 mg/kg to about 10 mg/kg or from about 0.1 mg/kg to about 12 mg/kg.

* * * * *